US007902422B2

(12) United States Patent
Guo et al.

(10) Patent No.: US 7,902,422 B2
(45) Date of Patent: Mar. 8, 2011

(54) REGULATING THE ETHYLENE RESPONSE OF A PLANT BY MODULATION OF F-BOX PROTEINS

(75) Inventors: Hongwei Guo, Beijing (CN); Joseph R. Ecker, Carlsbad, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

(21) Appl. No.: 12/643,033

(22) Filed: Dec. 21, 2009

(65) Prior Publication Data
US 2010/0175153 A1 Jul. 8, 2010

Related U.S. Application Data

(62) Division of application No. 11/298,286, filed on Dec. 9, 2005, now Pat. No. 7,655,835.

(60) Provisional application No. 60/635,121, filed on Dec. 10, 2004.

(51) Int. Cl.
*A01H 1/00* (2006.01)
*A01H 5/00* (2006.01)
*C12N 15/09* (2006.01)
*C12N 15/82* (2006.01)

(52) U.S. Cl. ......... 800/283; 800/278; 800/298; 800/320; 800/317; 800/306; 435/468

(58) Field of Classification Search .................. None
See application file for complete search history.

(56) References Cited

U.S. PATENT DOCUMENTS
2001/0034059 A1  10/2001  Allen et al.
2006/0200875 A1   9/2006  Guo et al.

OTHER PUBLICATIONS

Woo et al. The Plant Cell (2001), vol. 13, pp. 1779-1790.*
Xiao et al. Trends in Plant Science, 5(11):454-457, 2000.*
Alonso et al., "Genome-Wide Insertional Mutagenesis of *Arabidopsis thaliana*," *Science* 301:653-657, 2003.
Alonso et al., "EIN2, a Bifunctional Transducer of Ethylene and Stress Responses in *Arabidopsis*," *Science* 284:2148-2152, 1999.
Atanassova et al., "A 126 bp Fragment of a Plant Histone Gene Promoter Confers Preferential Expression in Meristems of Transgenic *Arabidopsis*," *Plant J.* 2:291-300, 1992.
Bechtold et al., "In Planta *Agrobacterium* Mediated Gene Transfer by Infiltration of Adult *Arabidopsis thaliana* Plants," *Life Sci.* 316:1194-1199, 1993.
Bitter et al., "Expression and Secretion Vectors for Yeast," *Meth. Enzymol.* 153:516-544, 1987.
Bleecker et al., "Insensitivity to Ethylene Conferred by a Dominant Mutation in *Arabidopsis thaliana*," *Science* 241:1086-1089, 1988.
Bleecker and Kende, "Ethylene: A Gaseous Signal Molecule in Plants," *Ann. Rev. Cell. Biol.* 16:1-18, 2000.
Brisson et al., "Expression of a Bacterial Gene in Plants by Using a Viral Vector," *Nature* 310:511-514, 1984.

Broglie et al. "Light-Regulated Expression of a Pea Ribulose-1,5-Bisphosphate Carboxylase Small Subunit Gene in Transformed Plant Cells," *Science* 224:838-843, 1984.
Chang et al., "*Arabidopsis* Ethylene-Response Gene ETR1: Similarity of Product to Two-Compound Regulators," *Science* 262:539-544, 1993.
Chao et al., "Activation of the Ethylene Gas Response Pathway in *Arabidopsis* by the Nuclear Protein Ethylene-Insenstive3 and Related Proteins," *Cell* 89:1133-1144, 1997.
Chen et al., "Localization of the Ethylene Receptor ETR1 to the Endoplasmic Reticulum of *Arabidopsis*," *J. Biol. Chem.* 277:19861-19866, 2002.
Coruzzi et al., "Tissue-Specific and Light-Regulated Expression of a Pea Nuclear Gene Encoding the Small Subunit of Ribulose-1,5-Bisphosphate Carboxylase," *EMBO J.* 3:1671-1679, 1984.
Deshaies, "SCF and Cullin-RING H2-Based Ubiquitin Ligases,"*Annu. Rev. Cell Dev. Biol.* 15:435-467, 1999.
Ecker, "The Ethylene Signal Transduction Pathway in Plants," *Science* 268:667-675, 1995.
Espelund et al., "Late Embryogenesis-Abundant Genes Encoding Proteins with Different Numbers of Hydrophilic Repeats are Regulated Differentially by Abscisic Acid and Osmotic Stress," *Plant J.* 2:241-252, 1992.
Fromm et al., "Expression of Genes Transferred Into Monocot and Dicot Plant Cells by Electroporation," *Proc. Natl. Acad. Sci. USA* 82:5824-5828, 1985.
Frugis et al., "Ubiquitin-Mediated Proteolysis in Plant Hormone Signal Transduction," *Trends Cell Biol.* 12:308-311, 2002.
Gagne et al., "The F-Box Subunit of the SCF E3 Complex is Encoded by a Diverse Superfamily of Genes in *Arabidopsis*," *Proc. Natl. Acad. Sci. USA* 99:11519-11524, 2002.
Gamble et al., "Histidine Kinase Activity of the ETR1 Ethylene Receptor from *Arabidopsis*," *Proc. Natl. Acad. Sci. USA* 95:7825-7829, 1998.
Gowda et al., "Identification of Promoter Sequences for the Major RNA Transcripts of Figwort Mosaic and Peanut Chlorotic Streak Viruses (Caulimovirus Group)," Abstract M318, p. 301, *Plant Gene Transfer*.
Gray et al., "Identification of an SCF Ubiquitin-Ligase Complex Required for Auxin Response in *Arabidopsis thaliana*," *Genes Dev.* 13:1678-1691, 1999.
Gray et al., "Auxin Regulates $SCF^{TIR1}$-Dependent Degradation of AUX/IAA Proteins," *Nature* 414:271-276, 2001.
Guo et al., "SUB1, and *Arabidopsis* $Ca^{2+}$-Binding Protein Involved in Cryptochrome and Phytochrome Coaction," *Science* 291:487-490, 2001.

(Continued)

*Primary Examiner* — Medina A Ibrahim
(74) *Attorney, Agent, or Firm* — Klarquist Sparkman, LLP

(57) ABSTRACT

The invention relates to transgenic plants having reduced sensitivity to ethylene as a result of having a recombinant nucleic acid encoding an F-box protein that interacts with a EIN3 involved in an ethylene response of plants, and a method of producing a transgenic plant with reduced ethylene sensitivity by transforming the plant with a nucleic acid sequence encoding an F-box protein. The inventions also relates to methods of altering the ethylene response in a plant by modulating the activity or expression of an F-box protein.

19 Claims, 9 Drawing Sheets

OTHER PUBLICATIONS

Guo and Ecker, "Plant Responses to Ethylene Gas Are Mediated by SCF$^{EBF1/EBF2}$-Dependent Proteolysis of EIN3 Transcription Factor," *Cell* 115:667-677, 2003.

Guo et al., "Protein Tolerance to Random Amino Acid Change," *Proc. Natl. Acad. Sci. USA* 101:9205-9210, 2004.

Gurley et al., "Upstream Sequences Required for Efficient Expression of a Soybean Heat Shock Gene," *Mol. Cell. Biol.* 6:559-565, 1986.

Guzmán and Ecker, "Exploiting the Triple Response of *Arabidopsis* to Identify Ethylene-Related Mutants," *Plant Cell* 2:513-523, 1990.

He et al., "The GSK3-Like Kinase BIN2 Phosphorylates and Destabilizes BZR1, a Positive Regulator of the Brassinosteroid Signaling Pathway in *Arabidopsis*," *Proc. Natl. Acad. Sci. USA* 99:10185-10190, 2002.

Hellmann and Estelle, "Plant Development: Regulation by Protein Degradation," *Science* 297:793-797, 2002.

Hochstrasser, "Ubiquitin-Dependent Protein Degradation," *Annu. Rev. Genet.* 30:405-439, 1996.

Hsiao et al., "Scrapie Prion: Teaching an Old Dogma New Tricks," *J. NIH Res.* 3:49-54, 1991.

Horsch et al., "A Simple and General Method for Transferring Genes into Plants," *Science* 227:1229-1231, 1985.

Hua et al., "*EIN4* and *ERS2* are Members of the Putative Ethylene Receptor Gene Family in *Arabidopsis*," *Plant Cell* 10:1321-1332, 1998.

Hua et al., "Ethylene Responses are Negatively Regulated by a Receptor Gene Family in *Arabidopsis thaliana*," *Cell* 94:261-271, 1998.

Huang et al., "Biochemical and Functional Analysis of CTR1, a Protein Kinase that Negatively Regulates Ethylene Signaling in *Arabidopsis*," *Plant J.* 33:221-233, 2003.

Ito et al., "Meristem-Specific Gene Expression Directed by the Promoter of the S-Phase-Specific Gene, *cyc07*, in Transgenic *Arabidopsis*," *Plant Mol. Biol.* 24:863-878, 1994.

Johnson and Ecker, "The Ethylene Gas Signal Transduction Pathway: A Molecular Perspective," *Annu. Rev. Genet.* 32:227-254, 1998.

Keskin et al., "A New, Structurally Nonredundant, Diverse Data Set of Protein-Protein Interfaces and Its Implications," *Prot. Sci.* 13:1043-1055, 2004.

Kieber et al., "*CTR1*, a Negative Regulator of the Ethylene Response Pathway in *Arabidopsis*, Encodes a member of the Raf Family of Protein Kinases," *Cell* 72:427-441, 1993.

Klee et al., "*Agrobacterium*-Mediated Plant Transformation and its Further Applications to Plant biology," *Ann. Rev. Plant Physiol.* 38:467-486, 1987.

Klein et al., "High-Velocity Microprojectiles for Delivering Nucleic Acids Into Living Cells," *Nature* 327:70-73, 1987.

Klein et al., "Transformation of Microbes, Plants and Animals by Particle Bombardment," *Bio/Tech.* 10:286-291, 1992.

Larsen and Chang, "The Arabidopsis *eer1* Mutant Has Enhanced Ethylene Responses in the Hypocotyl and Stem," *Plant Physiol.* 125:1061-1073, 2001.

Lee and Goldberg, "Proteasome Inhibitors: Valuable New Tools for Cell Biologists," *Trends Cell Biol.* 8:397-403, 1998.

Lin et al., "Expression of an *Arabidopsis* Cryptochrome Gene in Transgenic Tobacco Results in Hypersensitivity to Blue, UV-A, and Green Light," *Proc. Natl. Acad. Sci. USA* 92:8423-8427, 1995.

Lin et al., Accession No. Q9SKKO, deposited May 1, 2000.

Lopez-Molina et al., "A Postgermination Developmental Arrest Checkpoint is Mediated by Abscisic Acid and Requires the ABI5 Transcription Factors in *Arabidopsis*," *Proc. Natl. Acad. Sci. USA* 98:4782-4787, 2001.

Marcus-Sekura, "Techniques for Using Antisense Oligodeoxyribonucleotides to Study Gene Expression," *Anal. Biochem.* 172:289-295, 1988.

Martinez et al., "Spatial Pattern of *cdc2* Expression in Relation to Meristem Activity and Cell Proliferation During Plant Development," *Proc. Natl. Acad. Sci. USA* 89:7360-7364, 1992.

McGinnis et al., "The Arabidopsis *SLEEPY1* Gene Encodes a Putative F-Box Subunit of an SCF E3 Ubiquitin Ligase," *Plant Cell* 15:1120-1130, 2003.

Medford et al., "Molecular Cloning and Characterization of Genes Expressed in Shoot Apical Meristems," *Plant Cell* 3:359-370, 1991.

Mett et al., "Copper-Controllable Gene Expression System for Whole Plants," *Proc. Natl. Acad. Sci. USA* 90:4567-4571, 1993.

Ngo et al., in *The Protein Folding Problem and Tertiary Structure Prediction*, Merz Jr. and Le Grand (eds.), pp. 491-495, Birkhäuser Boston, 1994.

Odell et al., "Identification of DNA Sequences Required for Activity of the Cauliflower Mosaic Virus 35S Promoter," *Nature* 313:810-812, 1985.

Ouaked et al., "A MAPK Pathway Mediates Ethylene Signaling in Plants," *EMBO J.* 22:1282-1288, 2003.

Potuschak et al., "EIN3-Dependent Regulation of Plant Ethylene Hormone Signaling by Two-*Arabidopsis* F Box Proteins: EBF1 and EBF2," *Cell* 115:679-689, 2003.

Roman et al., "Genetic Analysis of Ethylene Signal Transduction in *Arabidopsis thaliana*: Five Novel Mutant Loci Integrated into a Stress Response Pathway," *Genetics* 139:1393-1409, 1995.

Ruijter et al., "F-Box Proteins in *Arabidopsis*," *Trends Plant Sci.* 5:1360-1365, 2000.

Sakai et al., "*ETR2* is an *ETR1*-Like Gene Involved in Ethylene Signaling in *Arabidopsis*," *Proc. Natl. Acad. Sci. USA* 95:5812-5817, 1998.

Sanford et al., "An Improved, Helium-Driven Biolistic Device," *Technique-A Journal of Methods in Cell and Molecular Biology* 3:3-16, 1991.

Sasaki et al., "Accumulation of Phosphorylated Repressor for Gibberellin Signaling in an F-box Mutant," *Science* 299:1896-1898, 2003.

Schena et al., "A Steroid-Inducible Gene Expression System for Plant Cells," *Proc. Natl. Acad. Sci. USA* 88:10421-10425, 1991.

Severin and Schöffl, "Heat-Inducible Hygromycin Resistance in Transgenic Tobacco," *Plant Mol. Biol.* 15:827-833, 1990.

Solano et al., "Nuclear Events in Ethylene Signaling: A Transcriptional Cascade Mediated by Ethylene-Insensitive3 and Ethylene-Response-Factor1," *Genes Dev.* 12:3703-3714, 1998.

Stepanova and Ecker, "Ethylene Signaling: From Mutants to Molecules," *Curr. Opin. Plant Biol.* 3:353-360, 2000.

Takamatsu et al., "Expression of Bacterial Chloramphenicol Acetyltransferase Gene in Tobacco Plants Mediated by TMV-RNA," *EMBO J.* 6:307-311, 1987.

Thornton et al., "From Structure to Function: Approaches and Limitations," *Nature Structural Biology, Structural Genomics Supplement*, pp. 991-994, 2000.

Velten et al., "Isolation of a Dual Plant Promoter Fragment from the Ti Plasmid of *Agrobacterium tumefaciens*," *EMBO J.* 3:2723-2730, 1984.

Vierstra, "The Ubiquitin/26S Proteasome Pathway, the Complex Last Chapter in the Life of Many Plant Proteins," *TRENDS Plant Sci.* 8:135-142, 2003.

Wallace et al., "The Use of Synthetic Oligonucleotides as Hybridization Probes. II. Hybridization of Oligonucleotides of Mixed Sequence to Rabbit β-Globin DNA," *Nucleic Acids Res.* 9:879-894, 1981.

Wang et al., "Ethylene Biosynthesis and Signaling Networks," *Plant Cell* S131-S151, 2002.

Wells, "Additivity of Mutational Effects in Proteins," *Biochem.* 29:8509-8517, 1990.

Xie et al., "*COI1*: An *Arabidopsis* Gene Required for Jasmonate-Regulated Defense and Fertility," *Science* 280:1091-1094, 1998.

Xiao and Jang, "F-Box Proteins in *Arabidopsis*," *Trends Plant Sci.* 5:454-457, 2000.

Yin et al., "BES1 Accumulates in the Nucleus in Response to Brassinosteroids to Regulate Gene Expression and Promote Stem Elongation," *Cell* 109:181-191, 2002.

\* cited by examiner

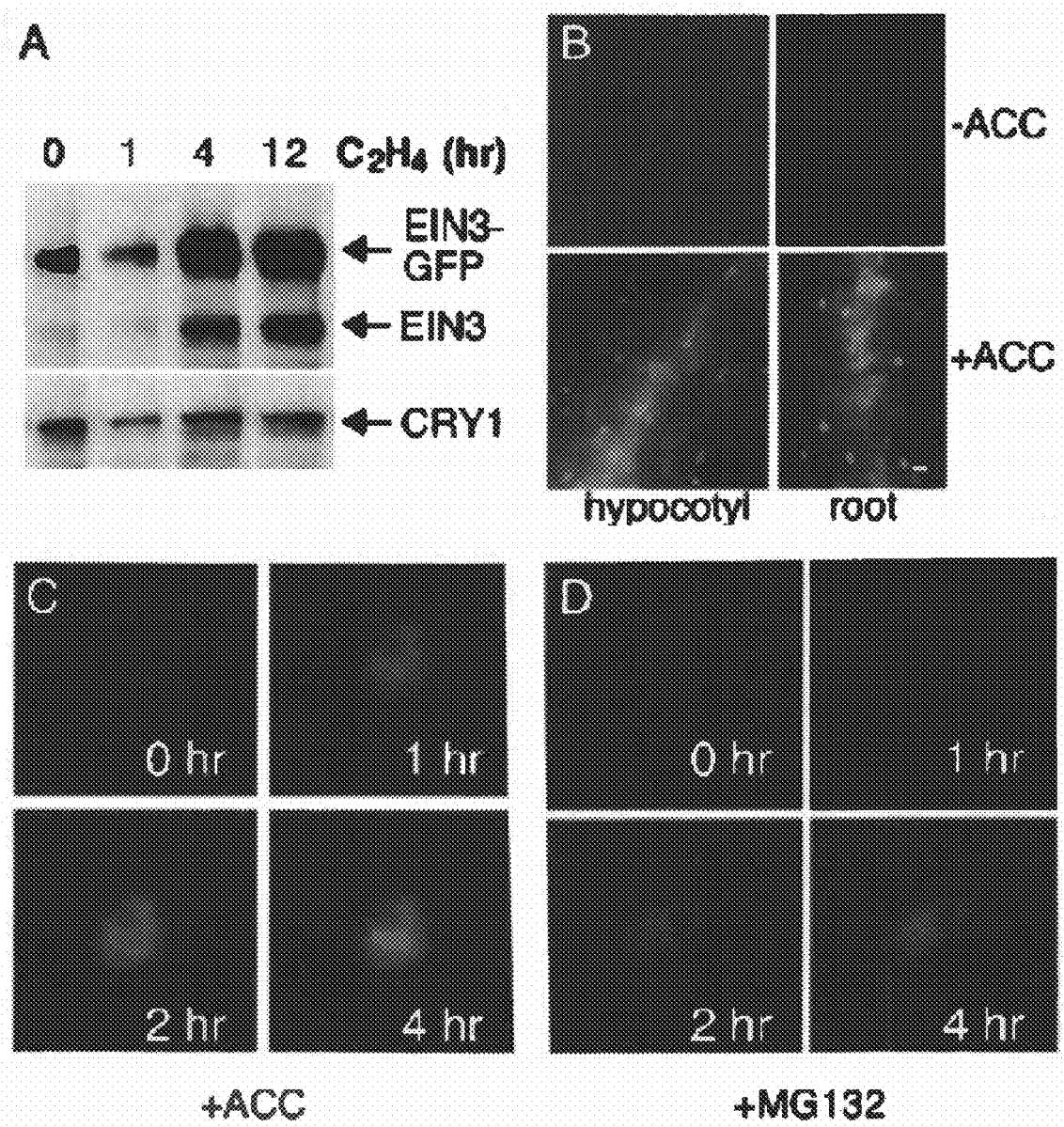

FIG. 4A

| | | |
|---|---|---|
| EBF1 | MSQIFSFAGENDFYRRGAIYPNPKDASLLLSIGSFADVYFPPSKKRSRVVAPTIFSAFEKK | 60 |
| EBF2 | MSGIFRFSGDEDCLLGGSMYLSP------GSCPGVYYPARKRLRVAATSFYSGFEEK | 51 |
| EBF1 | PVSIDVLPDECLFEIFRRLSGPQERSACAFVSKQMLTIVSSIRQKEIDVPSKITEDGDDC | 120 |
| EBF2 | QISIDVLPEECLFEILRRLPSGQERSACACVSKHMINLSSISRSEVNESS---VQDVEEG | 109 |
| EBF1 | EGCLSRSLDGKKATDVRLAAIAVGTAGRGGLGKISIRGS-NSAKVSDLGRSIGRSCPSL | 179 |
| EBF2 | EGFLSRSLEGKKATDLRLAAIAVGTSSRGGLGKIQIRGSGFESKVTDVGLGAVAHGCPSL | 169 |
| EBF1 | GSLSLMNVSTITDNGLLEIAEGCAQLEKLEINRCSTITDKGLVAIAKSCPNITELTLEAC | 239 |
| EBF2 | RIVSLMNLPAVSDLGLSEIARSCPMIEKLDISRCPGITDSGIVAIAENCVNISDFIDSC | 229 |
| EBF1 | SRIGDEGLLATARSCSKIKSVSIKNCPLVRDQGIASEISNTTCSEAKLKLQMLNVTDVSL | 299 |
| EBF2 | SGVGNEGIRAIARRCVNLRSISIRSCPRIGDQGVAFLIAQAGSYLTKVKLQMLNVSGLSL | 289 |
| EBF1 | AVVGHYGLSITDLVIAGISHVSEKGFWVNGNGVGLQKINSLTITACQGVIDMGLESVCKG | 359 |
| EBF2 | AVIGHYGAAVTDLVLHGIQGVNEKGFWVMGNAKGLKKIKSLSVMSCRGMDVGLEAVGNG | 349 |
| EBF1 | CPNMKKAIISKSPILSDNGLVSFAKASLSLESIQLEECHRVTQFGFFGSLINCGEKLKAF | 419 |
| EBF2 | CPDLKHVSLNKCLIVSGKGLVALAKSALSLESILKLEECHRINQFGLMGFIMNCGSKLKAT | 409 |
| EBF1 | SLVNCLSIRDLTT---GLPASSHCSALRSLSIRNCPGFGDANLAAIGKLCPQIEDIDLCGL | 477 |
| EBF2 | SLANCLGLSDFNSESSLPSPS--CSSLRSLSIRCCPGFGDASLAFLGKFCHQLQDVELCGL | 468 |
| EBF1 | KGITESGFLHLIQSS---IVKIINFSGCSNLTDRVISAITARNGWTLEVINIDGCSNITDF | 534 |
| EBF2 | NGVIDAGVRELLQSNNVGLVKVNLSECINVSDNTVSAISVCHGRTLESINLDGCKNINA | 528 |
| EBF1 | SLVSIAANCQILSDLDISKCAISDSGIQALASS-DKIKLQILSVAGCSMVTDKSLPATVG | 593 |
| EBF2 | SLVAVAKNCYSVNDLDISNTLVSBHGIKALASSPNHINLQVLSIGGCSSIPDKSKACIQK | 588 |
| EBF1 | LGSTLLGLNLQQCRSISNSTVDFIVERLYKCDILS 628 | |
| EBF2 | LGRTLLGLNIQRCGRISSSTVDTILENIWRCDILY 623 | |

FIG. 4B

```
EBF1       VSIDVLPDECLFE.IFRRLSGPQERSACAFVSKQWLTLVSSIRQK
EBF2       TSIDVLPECLFE.ILRRLPSCQERSACACVSKHWLMLSSISRS
TIR1       RIALSFPEEVLEH.VFSFIQLDKDRNSVSLVCKSWYEIERWCRRK
COI1       LSCVATVDDVIEQ.VMTYITDPKDRDSASLVCRRWFKIDSETREH
SLY1       .IGFSNLDENLVYEVLKHVD.AKTLAMSCVSKIIWHKTAQDERLW
ORE9       TTLSDLPDVILST.ISSLVSDSRARNSLSLVSHKPLAERSTRSH
UFO        RIWSKLPPPLLDR.VIAFLP.PPAFFRTRCVCKRFYSLLFSNTFL
FKP1       CGILQLSDEVLAHNILSRLT.PRDVASIGSACRRLRQLTKNESVR
ZTL        CGLFQLSDEVVSHKILSRLT.PRDVASVSSVCRRLYVLTKNEDLW
SOM1       ....MALPWELEED.ILSRLP.PISLVRFRTVSKHWNSLFNDKIFI
EID1       SVFSCIPEDVVFHIFFKLQDDPRNWARLACVCTKFSSIVRNVCCK
CyclinF    LTILSLPEDVLFH.ILKWLS.VEDILAVRAVHSQLKDLVDNHASV
SKP2       VSWDSLPDELLLG.IFSCLP.ELLKVSGVCKRWYRLASDESLW
CDC4       DLITSLPFEISLK.IFNYLQ.FEDIINSLGVSQMNKIIRKSTSL
consensus          ******  *      *         *    *     ***
```

REGULATING THE ETHYLENE RESPONSE OF A PLANT BY MODULATION OF F-BOX PROTEINS

CROSS REFERENCE TO RELATED APPLICATIONS

This application is a divisional of U.S. application Ser. No. 11/298,286, filed Dec. 9, 2005, now U.S. Pat. No. 7,655,835 issued Feb. 2, 2010, which claims the benefit of U.S. Provisional Application No. 60/635,121, filed Dec. 10, 2004, which is hereby incorporated by reference in its entirety.

GOVERNMENT SUPPORT

This invention was made with United States Government Support under Grant No. 1F32GM66639 from the National Institute of Health, Grant No. MCB-0213154 from the National Science Foundation, and Grant No. DE-FG03-00 ER15113 from the Department of Energy. The United States Government has certain rights in this invention.

BACKGROUND OF THE INVENTION

1. Field of the Invention

The field of the invention relates to methods of modulating at least one trait in a plant. In particular, this invention relates to the modulation of traits involved in the ethylene response in a plant, including germination, flower and leaf senescence, fruit ripening, leaf abscission, root nodulation, programmed cell death, and responsiveness to stress and pathogen attack. Also encompassed are transgenic plants produced by the disclosed methods.

2. Background

Ethylene ($C_2H_4$) is a gaseous plant hormone that affects myriad developmental processes and fitness responses in plants, such as germination, flower and leaf senescence, fruit ripening, leaf abscission, root nodulation, programmed cell death, and responsiveness to stress and pathogen attack (Johnson, P. R. and Ecker J. R., *Annu Rev Genet.* 32,227-254, 1998). Another effect of ethylene on plant growth is the so-called triple response of etiolated dicotyledoneous seedlings. This response is characterized by the inhibition of hypocotyl and root cell elongation, radial swelling of the hypocotyl, and exaggerated curvature of the apical hook. Over the past decade, genetic screens based on the triple response phenotype have identified more than a dozen genes involved in the ethylene response in plants. These genes can be divided into three distinct categories: constitutive triple response mutants (eto1, eto2 and eto3, ctr1 and ran1/ctr2); ethylene insensitive mutants (etr1, etr2, ein2, ein3, ein4, ein5, and ein6); and tissue-specific ethylene insensitive mutants (hls1, eir1, and several auxin resistant mutants).

Genetic and molecular analysis of these mutants has defined a largely linear ethylene response pathway ranging from the hormone perception at the membrane to transcriptional regulation in the nucleus. Ethylene is perceived by a family of membrane-associated receptors, including ETR1/ETR2, ERS1/ERS2 and EIN4 in *Arabidopsis*. Ethylene binds to its receptors via a copper cofactor, and plays a negative role, whereby ethylene binding represses activity of the receptor. In the absence of ethylene, the receptors are hypothesized to be in a functionally active form that constitutively activates a Raf-like serine/threonine kinase, CTR1, also a negative regulator of the pathway. EIN2, EIN3, EIN5, and EIN6 are positive regulators of ethylene responses, acting downstream of CTR1. EIN2 is an integral membrane protein. Loss-of-function mutations in EIN2 cause complete ethylene insensitivity, indicating that EIN2 is a positive component essential for the ethylene responses. Ethylene signaling downstream of EIN2 is mediated by EIN3, a nuclear protein. The nuclear protein EIN3 is a transcription factor that regulates the expression of its immediate target genes such as ERF1. ERF1 belongs to a large family of AP2 domain-containing transcriptional factors that have been shown to bind to a GCC-box present in the promoters of many ethylene-inducible, defense-related genes. Thus a transcriptional cascade mediated by EIN3/EIL and ERF proteins leads to the regulation of ethylene-controlled gene expression (Wang, K. L., et al. *Plant Cell* 14 Suppl, S131-151, 2002). The ein3 mutants show a loss of ethylene-mediated effects including gene expression, triple response, cell growth inhibition, and reduced senescence. Conversely, overexpression of EIN3 results in constitutive ethylene responses in both wild-type and ein2 mutant backgrounds. These results demonstrate that EIN3 is both necessary and sufficient for the activation of the ethylene pathway. Biochemical studies revealed that EIN3 protein can bind to a specific sequence in the promoter of a target gene, ERF1 (Solano et al., 1998).

Although EIN3 has been shown to be an essential transcription factor mediating a diverse array of plant responses to ethylene, the mechanism of its activation by ethylene has eluded characterization. Indeed, the mechanism by which genes involved in the ethylene response of plants are regulated is poorly understood. Thus, there is a need for identification of the mechanisms whereby the ethylene response in plants is regulated. Further, there is a need for methods of modulating of the mechanisms regulating the ethylene response to control aspects of the ethylene such as senescence, fruit ripening, the stress response, germination, pathogen resistance, and leaf abscission.

BRIEF SUMMARY OF THE INVENTION

Using a variety of genetic and molecular techniques, the regulation of the EIN3 transcription factor was examined, and a post-transcriptional mechanism for regulating a plant cell's response to ethylene using F-box proteins was elucidated. In particular, the F-box proteins EBF1 and EBF2 were identified as F-box proteins that bind to EIN3 and target the EIN3 protein for degradation through the ubiquitin/proteasome pathway.

Transgenic plants having an altered sensitivity to ethylene are described herein. The plant may include a recombinant nucleic acid sequence that alters the expression of an F-box gene, wherein the F-box gene encodes a first protein that interacts with a second protein wherein said second protein is involved in the ethylene response of the plant. These transgenic plants may have an enhanced sensitivity to ethylene. In some versions of the transgenic plant having an enhanced sensitivity to ethylene, the recombinant nucleic acid sequence disrupts the expression of the F-box gene.

In some versions, the transgenic plant has a reduced sensitivity to ethylene. In versions of the transgenic plant having a reduced sensitivity to ethylene, the recombinant nucleic acid sequence increases the expression of the F-box gene.

The recombinant nucleic acid sequence may include a sequence that hybridizes to the F-box gene under high stringency. The recombinant nucleic acid sequence may encode an F-box protein that encodes a first protein that interacts with a second protein wherein the second protein is involved in the ethylene response of the plant.

The F-box gene may include a polynucleotide sequence that hybridizes to the sequence of SEQ ID NO: 1 under high stringency. The F-box gene may include a polynucleotide sequence that hybridizes to the sequence of SEQ ID NO: 3 under high stringency. The second protein involved in the ethylene response may include a protein having at least 80% identity to SEQ ID NO: 6. In some versions, the second protein includes the EIN3 protein.

In one version, a transgenic plant has an increased sensitivity to ethylene. In this version, the plant may include a recombinant nucleic acid sequence that disrupts the expression of an EBF gene, wherein the EBF gene encodes a protein (e.g., EBF1 and/or EBF2) that interacts with a member of the EIN3/EIL family of transcription factor proteins.

Also described herein are seeds produced from transgenic plants having an altered sensitivity to ethylene. The plants may include a recombinant nucleic acid sequence that alters the expression of an F-box gene, wherein the F-box gene encodes a first protein that interacts with a second protein wherein the second protein is involved in the ethylene response of the plant.

In some versions, the recombinant nucleic acid sequence is operably linked to a promoter. The promoter may be a constitutive promoter or an inducible promoter. The promoter may be a tissue-specific promoter.

In some versions, the plant is chosen from dicotyledons and monocotyledons including but not limited to rice, maize, wheat, barley, sorghum, millet, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussel sprout, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, plums, cranberries, grapefruit, lemons, limes, nectarines, oranges, peaches, pears, tangelos, tangerines, carnation, chrysanthemum, petunia, rose, geranium, violet, gladioli, orchid, lilac, crabapple, sweetgum tree, maple tree, poinsettia, locust tree, oak tree, ash tree and linden tree. The plant may be *Arabidopsis thaliana*.

Also described herein are plant tissues derived from transgenic plants having an altered sensitivity to ethylene, said plants including a recombinant nucleic acid sequence that alters the expression of an F-box gene, wherein the F-box gene encodes a first protein that interacts with a second protein wherein the second protein is involved in the ethylene response of the plant.

Also described herein are methods of regulating at least one aspect of the ethylene response of a plant including modulating the activity or expression of an F-box protein. In some versions, the ethylene response may be modulated by treating the plant with a compound that modulates the activity or expression of an F-box protein. Treating may include immersing, spraying, powdering, drenching, dripping, or irrigating the plant with the compound.

In some versions, modulating the activity or expression of an F-box protein includes enhancing or inhibiting the binding of an F-box protein to a protein encoded by a gene involved in the ethylene response of the plant. Enhancing or inhibiting the binding of an F-box protein to a protein encoded by a gene involved in the ethylene response may include enhancing or inhibiting the binding of an F-box protein to a transcription factor involved in the ethylene response. Enhancing or inhibiting the binding of an F-box protein to a transcription factor involved in the ethylene response may include enhancing or inhibiting the binding of an F-box protein to a protein having at least 80% identity to SEQ ID NO: 6. Enhancing or inhibiting the binding of an F-box protein to a transcription factor involved in the ethylene response may include enhancing or inhibiting the binding of an F-box protein to an EIN3 protein. Modulating the activity or expression of an F-box protein may include modulating the activity or expression of an F-box protein having at least 80% identity to SEQ ID NO: 2. Modulating the activity or expression of an F-box protein may include modulating the activity or expression of an F-box protein including the sequence shown in SEQ ID NO: 2. Modulating the activity or expression of an F-box protein may include modulating the activity or expression of an F-box protein including at least 80% identity to SEQ ID NO: 4. Modulating the activity or expression of an F-box protein may includes modulating the activity or expression of an F-box protein including the sequence shown in SEQ ID NO: 4.

In some versions, the aspect of the ethylene response that is regulated may be any of: senescence, fruit ripening, fruit drop, the stress response, germination, pathogen resistance, leaf abscission, the triple response in an etiolated seedling, or stability of an EIN3 protein. In one version, the aspect of the ethylene response that is regulated is the stability of a protein having at least 80% identity to SEQ ID NO: 6.

Also described herein are methods of regulating at least one aspect of the ethylene response of a plant including modulating the activity or expression of an EBF protein, such as EBF1 and/or EBF2.

Also described herein is a method of identifying a compound that modulates the ethylene response of a plant including: contacting a plant, part of a plant, or a plant cell with a compound, wherein the plant, part of a plant, or a plant cell expresses a recombinant nucleic acid encoding an F-box protein wherein the F-box protein interacts with a protein involved in the response of the plant to ethylene; detecting the activity or expression of the F-box protein; and comparing the activity or expression of the F-box protein after contacting the plant, part of a plant, or a plant cell with the compound to the activity or expression of the F-box protein in the absence of the compound to identify a compound that modulates the ethylene response of said plant.

In some versions of the method of identifying a compound that modulates the ethylene response of a plant, the F-box protein includes an F-box protein whose expression is influenced by ethylene. The F-box protein may have at least 80% identity to SEQ ID NO: 2. The F-box protein may include the sequence shown in SEQ ID NO: 2. The F-box protein may include proteins having at least 80% identity to SEQ ID NO: 4. The F-box protein may include the sequence shown in SEQ ID NO: 4. The F-box protein may interact with a protein having at least 80% identity to SEQ ID NO: 6. The F-box protein may interact with a protein having the sequence shown in SEQ ID NO: 6.

In some versions, the activity or expression of the F-box protein that is detected and compared includes binding of the F-box protein to a target. The target may include a protein encoded by a gene involved in the ethylene response of the plant. The gene involved in the ethylene response of the plant may include a protein having at least 80% identity to SEQ ID NO: 6.

In one version, the method of identifying a compound that modulates the ethylene response of a plant includes: contacting a plant, part of a plant, or a plant cell with a compound, wherein the plant, part of a plant, or a plant cell expresses a recombinant nucleic acid encoding an EBF protein (e.g., EBF1 and/or EBF2) wherein the EBF protein interacts with a member of the EIN3/EIL family of transcription factors involved in the response of the plant to ethylene; detecting the activity or expression of the EBF protein; and comparing the activity or expression of the EBF protein after contacting the plant, part of a plant, or a plant cell with the compound to the activity or expression of the EBF protein in the absence of the compound to identify a compound that modulates the ethylene response of the plant.

Also described herein are methods of making a transgenic plant having an altered sensitivity to ethylene including: contacting a plant cell with a recombinant nucleic acid that alters the expression of an F-box gene, wherein the F-box gene encodes a first protein that interacts with a second protein involved in the response of the plant to ethylene; and producing a plant from the plant cell.

The plant may be a dicotyledonous plant. The plant may be a monocotyledonous plant. The F-box gene may include a polynucleotide sequence that hybridizes to the sequence of SEQ ID NO: 1 under high stringency. The F-box gene may include a polynucleotide sequence that hybridizes to the sequence of SEQ ID NO: 3 under high stringency. The gene involved in the ethylene response may includes a polynucleotide sequence that hybridizes to the sequence of SEQ ID NO: 5 under high stringency.

In some versions, the recombinant nucleic acid disrupts more than one F-box gene encoding an F-box protein that interacts with a protein encoded by a gene involved in the ethylene response. During the making of a transgenic plant having an altered sensitivity to ethylene, the step of contacting the plant cell with a recombinant nucleic acid may be by physical means. The step of contacting may be by chemical means. The plant cell may be chosen from protoplasts, gamete producing cells, and cells that regenerate into a whole plant.

In one version, the methods of making a transgenic plant having an altered sensitivity to ethylene includes contacting a plant cell with a recombinant nucleic acid that alters the expression of an EBF gene (e.g., EBF1 or EBF2), wherein the EBF gene encodes a first protein that interacts with a member of the EIN3/EIL family of transcription factors involved in the response of the plant to ethylene; and producing a plant from the plant cell. In another format, the methods include detecting the activity or expression of proteins involved in the ethylene response pathway, such as EIN3.

Also described herein is a recombinant nucleic acid sequence including SEQ ID NO: 3. A recombinant nucleic acid sequence hybridizing to SEQ ID NO: 3 under high stringency is also described.

BRIEF DESCRIPTION OF THE DRAWINGS

FIGS. 3A-3D show that EIN3-GFP fusion protein is accumulated in the nucleus upon ethylene or MG132 treatment. (A) The levels of EIN3-GFP fusion protein are induced by ethylene. (B) EIN3-GFP is present in the nucleus (visualized by DAPI staining, data not shown) of both hycopotyl and root cells at low levels in the absence of ACC (−ACC). ACC treatment (+ACC) increases EIN3-GFP nuclear accumulation. Scale bar=20 µm. (C) A time course study showing that the induction of EIN3-GFP nuclear accumulation by 50 µM of ACC. (D) MG132 (50 µM) also induces EIN3-GFP nuclear accumulation.

FIGS. 4A-4E show that the F-box Proteins EBF1 and EBF2 Interact with EIN3. (A) Alignment of EBF1 (SEQ ID NO: 2) and EBF2 (SEQ ID NO: 4) amino acid sequences generated with ClustalW program. Identical amino acid residues in the two proteins are highlighted with black boxes. The putative F-box motif sequences are boxed, and the 18 deduced leucine-rich repeats (LRRs) are indicated by arrows above the sequences. (B) Alignment of F-box motif sequences. Cyclin F (SEQ ID NO: 18) and SKP2 (SEQ ID NO: 19) are from human, CDC4 (SEQ ID NO: 20) from yeast, and all others (SEQ ID NOS: 7-17) from Arabidopsis. Identities and similarities among the different proteins are highlighted by black and gray, respectively. Consensus residues are denoted by asterisks. (C) The two F-box proteins and their corresponding LRR domains interact with EIN3 in yeast two-hybrid assays. (D) Both F-box proteins interact with the ASK1 protein in yeast two-hybrid assays. (E) The EBF1 and EBF2 genes are induced by ethylene. Etiolated wild-type seedlings were treated with air (air) or ethylene ($C_2H_4$) for 4 hr before RNA was extracted for analysis. Each treatment was performed in replicate. The means of normalized intensity were used to indicate relative expression levels.

DETAILED DESCRIPTION OF THE INVENTION

Figure 1:
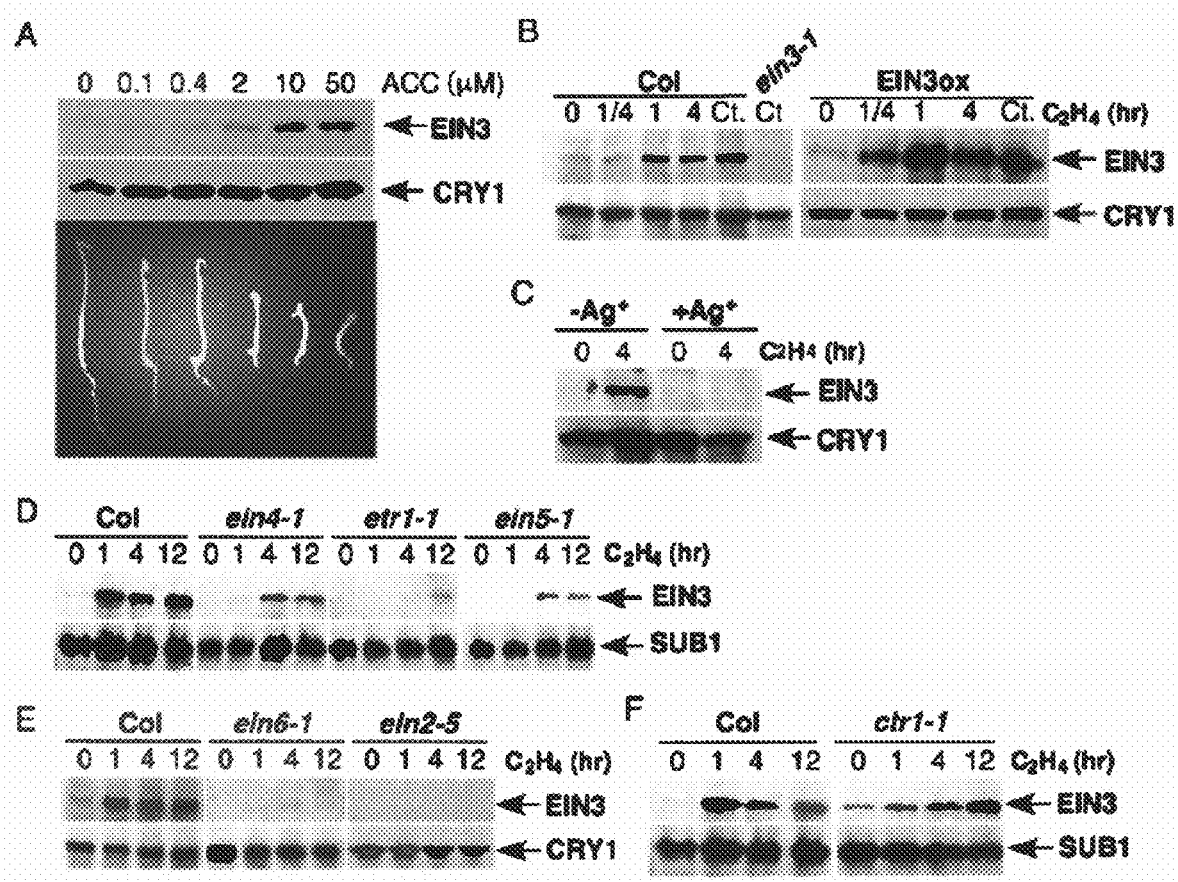
FIGS. 1A-1F show the induction of EIN3 protein by ethylene. (A) The abundance of EIN3 protein correlates with the strength of triple response. Etiolated wild-type seedlings (Col) were grown on medium supplemented with various concentrations of ACC (aminocyclopropane-1-carboxylic acid, an ethylene precursor) for 3 days. Total protein extracts were subjected to immunoblot with anti-EIN3 antibody. After stripping, the same membrane was re-probed with anti-CRY 1 (Arabidopsis cryptochrome 1) or anti-SUB 1 (Arabidopsis SHORT UNDER BLUE 1) antibody (in FIG. 1D, 1F) as a loading control (middle panel). Seedlings were photographed for triple response phenotype (bottom panel). (B) The levels of both endogenous and transgenically expressed EIN3 protein are induced by ethylene. Etiolated seedlings of Col and EIN3ox were grown in the air (indicated by time point 0) and subsequently treated with ethylene gas (10 ppm, all the same below) for the indicated amounts of time. Total protein extracts were subjected to immunoblot assays. Ct. indicates seedlings continuously grown in ethylene gas. (C) EIN3 accumulation is abolished by Ag+ treatment. Etiolated wild-type seedlings were grown on MS medium without or with 100 µM of $AgNO_3$ for 3 days and treated with air or ethylene for 4 hr. (D) & (E) EIN3 accumulation is impaired in various ethylene insensitive mutants. (F) EIN3 is constitutively accumulated in ctr1 mutant.

Described herein are transgenic plants having a modified ethylene response, methods of making these transgenic plants, methods of regulating at least one aspect of the ethylene response of a plant, methods of identifying compounds that modulate the ethylene response of a plant, and a recombinant nucleic acid sequence encoding an F-box protein that modulates the ethylene response of a plant by binding to the EIN3 protein.

Embodiments of the invention are based, in part, on the recognition that proteins involved in the ethylene response pathway in plants may be regulated by F-box proteins that may target them for degradation by the ubiquitination/proteosome pathway. In particular, the EIN3 family of transcription factors may be targeted for degradation by F-box proteins such as EBF1 and EBF2 (for EIN3 Binding F-box protein 1 and 2). Experimental and theoretical support for this interaction is provided below. As used herein, unless the context makes it clear otherwise, the term "F-box gene" refers to an F-box gene encoding an F-box protein that interacts with a protein involved in the ethylene response of a plant. EBF proteins include EIN3 binding F-box proteins, such as EBF1 and EBF2 as described herein.

Embodiments of the invention are also based partly upon the identification of an F-box protein gene, EBF2, that is involved in regulating a plant's response to ethylene. Thus, one embodiment of the invention provides isolated nucleic acids including nucleotide sequences including or related to the EBF2 genes and/or encoding polypeptides including or related to the EBF2 proteins. Further, other F-box proteins may also be modulated to regulate a response to ethylene by a plant, including known F-box proteins such as EBF 1. Thus, one embodiment of the invention provides isolated nucleic acids including nucleotide sequences including or related to the EBF1 genes and/or encoding polypeptides including or related to the EBF1 proteins. Although this disclosure specifically describes the EBF1 and EBF2 F-box proteins, other F-box proteins having the characteristics described below may also be used in the methods of the invention.

EBF1 and EBF2 sequences include the specifically disclosed sequences, and splice variants, allelic variants, synonymous sequences, and homologous or orthologous variants thereof. Thus, for example, embodiments of the invention include genomic and cDNA sequences from the EBF1 and EBF2 genes.

Embodiments of the invention also include allelic variants and homologous or orthologous sequences. For example, these variants are useful in allele specific hybridization screening or PCR amplification techniques. Moreover, subsets of the EBF1 and/or EBF2 sequences, including both sense and antisense sequences, and both normal and mutant sequences, as well as intronic, exonic and untranslated sequences, may be employed for these techniques. Such sequences may include a small number of consecutive nucleotides from the sequence disclosed or otherwise enabled herein but preferably include at least 8-10, and more preferably 9-25, consecutive nucleotides from EBF1 and/or EBF2 sequences. Various nucleic acid constructs in which EBF1 and/or EBF2 sequences, either complete or subsets, are operably joined to exogenous sequences to form cloning vectors, expression vectors, fusion vectors, transgenic constructs, and the like are also contemplated.

EBF1 and EBF2 were shown to modulate the ethylene response in *Arabidopsis*, as described below. Further, EBF2, and mutants of EBF 1 and EBF2 were identified in *Arabidopsis* lines. Accordingly, embodiments of the invention include the EBF1 and EBF2 genes and mutations thereof, as well as a characterization of the EBF1 and EBF2 mutants discovered in *Arabidopsis*. However, the disclosed methods are not limited to any particular plant type. It is expected that similar mutations in other plants will result in similar phenotypes.

Embodiments of the invention also include functional EBF1 and/or EBF2 polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The terms "functional fragments of EBF1 polypeptide", and "functional fragments of EBF2" refer to all fragments of EBF1 and EBF2 that retain the activity described herein, e.g., ability to modulate the ethylene response of a plant, portion or a plant, or plant cell. Biologically functional fragments, for example, can vary in size from a polypeptide fragment as small as an epitope capable of binding an antibody molecule to a large polypeptide capable of participating in the characteristic induction or programming of phenotypic changes within a cell. The "ethylene response" refers to a plant trait that is mediated by ethylene gas, including but not limited to germination, flower and leaf senescence, fruit ripening, fruit drop, leaf abscission, root nodulation, programmed cell death, responsiveness to stress, responsiveness to pathogen attack, and the "triple response" of etiolated dicotyledoneous seedlings (e.g., inhibition of hypocotyl and root cell elongation, radial swelling of the hypocotyl, and exaggerated curvature of the apical hook).

Ethylene causes developmental changes that result in fruit ripening. New enzymes are made because of the ethylene signal. These include hydrolases to facilitate break down of fruit components, amylases to accelerate hydrolysis of starch into sugar, pectinases to catalyze degradation of pectin, and so on. Ethylene increases the transcription of genes that are then transcribed and translated to make these enzymes. The enzymes then catalyze reactions to alter the characteristics of the fruit.

Enzymes produced as a result of exposure to ethylene facilitate the ripening responses. Chlorophyll is broken down and sometimes new pigments are made so that the fruit skin changes color from green to red, yellow, or blue. Acids are broken down so that the fruit changes from sour to neutral. The degradation of starch by amylase produces sugar. This reduces the mealy (floury) quality and increases juiciness of the fruit. The breakdown of pectin by pectinase results in a softer fruit. Enzymes also break down large organic molecules into volatile smaller molecules which are detected as an aroma.

Fruit drop is related to fruit ripening. The fruit-ripening process described above, also occurs in a layer of cells in the pedicel near the point of attachment to the stem of the plant. This layer of cells in the pedicel is often called the abscission zone because this layer will eventually separate and the fruit will drop from the plant.

The cells in this cross sectional layer in the pedicel receive the ethylene signal from the ripening fruit. Reception of the signal results in the production of new enzymes. The cells "ripen" and pectinases attack the cells of the abscission zone. When the cell connection have been sufficiently weakened, the weight of the fruit will cause it to fall from the plant.

Plant senescence is a genetically programmed process; it is the last phase of plant development and ultimately leads to death. Plant hormones such as ethylene and cytokinins play vital roles in the regulation of senescence.

Many modifications of the EBF1 and/or EBF2 primary amino acid sequence may result in plants having an enhanced sensitivity to ethylene (e.g., ethylene hypersensitivity). In some versions, the modification of the EBF1 and/or EBF2 primary amino acid sequence results in a reduced or eliminated expression of EBF1 and/or EBF2. In some variations, the modification of the EBF1 and/or EBF2 primary amino acid sequence results in a reduced or eliminated binding of EBF1 and/or EBF2 to binding partners (e.g., EIN3, or members of the SCF complex). Such modifications may be deliberate, as by site-directed mutagenesis, or may be spontaneous. All of the polypeptides produced by these modifications are included herein. Further, deletion of one or more amino acids can also result in a modification of the structure of the resultant molecule without significantly altering its activity to affect the ethylene response. Deletions may include 1, 2, 3, 4 or 5 deleted amino acids. Deletions may include 6, 7, 8, 9 or 10 deleted amino acids. Deletions may also include 11, 12, 13, 14 or 15 deleted amino acids. Deletions may also include 16, 17, 18, 19 or 20 deleted amino acids. Deletions may also include 20-25 amino acid deletions, 25-30 amino acid deletions or 35 to 40 amino acid deletions. This can lead to the development of a smaller active molecule which could have broad utility in exhibiting enhanced sensitivity to ethylene (e.g., ethylene hypersensitivity).

Furthermore, some modifications of the EBF1 and/or EBF2 primary amino acid sequence may result in plants having a reduced sensitivity to ethylene (e.g., ethylene insensitivity). In some versions, the modification of the EBF1 and/or EBF2 primary amino acid sequence results in an increased or enhanced expression of EBF1 and/or EBF2. In some variations, the modification of the EBF1 and/or EBF2 primary amino acid sequence results in a increased or enhanced binding of EBF1 and/or EBF2 to binding partners (e.g., EIN3, or members of the SCF complex). Further, deletion of one or more amino acids can also result in a modification of the structure of the resultant molecule without significantly altering its activity to affect the ethylene response. Deletions may include 6, 7, 8, 9 or 10 deleted amino acids. Deletions may also include 11, 12, 13, 14 or 15 deleted amino acids. Deletions may also include 16, 17, 18, 19 or 20 deleted amino acids. Deletions may also include 20-25 amino acid deletions, 25-30 amino acid deletions or 35 to 40 amino acid deletions Such modifications may be deliberate, as by site-directed mutagenesis, or may be spontaneous. All of the polypeptides produced by these modifications are included herein.

EBF1 and EBF2 polypeptides include amino acid sequences substantially the same as the sequence set forth in SEQ ID NO: 2 and SEQ ID NO: 4, respectively, including mutants that result in plants having modified ethylene responses. The term "substantially the same" refers to amino acid sequences that provide nearly the same amino acid sequence and retain the activity of EBF 1 and/or EBF2 as described herein. The EBF 1 and/or EBF2 polypeptides of the invention include conservative variations of the polypeptide sequence.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided the protein retains its ability to alter the ethylene response.

FIGS. 4A-4E show that the F-box Proteins EBF1 and EBF2 Interact with EIN3. While a number of the amino acid sequences are only partial sequences from various databases, the sequence alignment shows regions of the protein that are more conserved that the others. In addition, one of skill in the art may perform additional sequence alignments using other known methods.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Such sequence alignments provide a good indication of the degree of variation of amino acid residues at any given position that may be tolerated. One of skill in the art would understand that highly conserved regions are less likely to tolerate significant variation while less conserved regions are more likely to tolerate variation. Also, one of skill in the art will appreciate that where corresponding residues vary between the sequences, such variation gives an indication of the nature of changes that are likely to be tolerated without disturbing the function of the protein.

EBF1 and/or EBF2 proteins can be analyzed by standard SDS-PAGE and/or immunoprecipitation analysis and/or Western blot analysis, for example. Embodiments of the invention also provide an isolated polynucleotide sequence encoding a polypeptide having the amino acid sequence of SEQ ID NO: 2 or SEQ ID NO: 4. The term "isolated" as used herein includes polynucleotides substantially free of other nucleic acids, proteins, lipids, carbohydrates or other materials with which it is naturally associated. Polynucleotide sequences of the invention include DNA, cDNA and RNA sequences which encode EBF1, EBF2 and EIN3. It is understood that polynucleotides encoding all or varying portions of EBF1 and/or EBF2 are included herein, as long as they encode a polypeptide with some EBF1 and/or EBF2 activity. Such polynucleotides include naturally occurring, synthetic, and intentionally manipulated polynucleotides as well as splice variants. For example, portions of the mRNA sequence may be altered due to alternate RNA splicing patterns or the use of alternate promoters for RNA transcription.

Moreover, EBF1 and/or EBF2 polynucleotides include polynucleotides having alterations in the nucleic acid sequence. For example, EBF1 and/or EBF2 may be altered so that it encodes a polypeptide having the ability to modulate an aspect of the ethylene response, such as germination, flower and leaf senescence, fruit ripening, leaf abscission, root nodulation, programmed cell death, responsiveness to stress, responsiveness to pathogen attack, and the "triple response" of etiolated dicotyledoneous seedlings. Alterations in EBF 1 and/or EBF2 nucleic acids include but are not limited to intragenic mutations (e.g., point mutation, nonsense (stop), antisense, splice site and frameshift) and heterozygous or homozygous deletions. Detection of such alterations can be done by standard methods known to those of skill in the art including sequence analysis, Southern blot analysis, PCR based analyses (e.g., multiplex PCR, sequence tagged sites (STSs)) and in situ hybridization. Embodiments of the invention also include anti-sense polynucleotide sequences.

The polynucleotides described herein include sequences that are degenerate as a result of the genetic code. There are 20 natural amino acids, most of which are specified by more than one codon. Therefore, all degenerate nucleotide sequences are included in the invention, particularly degenerate nucleotide sequences that encode EBF1 and/or EBF2 polypeptides that retain the activity of the EBF1 and/or EBF2 protein. A "functional polynucleotide" denotes a polynucleotide which encodes a functional polypeptide as described herein. In addition, embodiments of the invention also include a polynucleotide encoding a polypeptide having the biological activity of an amino acid sequence of SEQ ID NO: 2 or SEQ ID NO: 4 and retaining the ability to alter the plant's response to ethylene.

As used herein, the terms "polynucleotides" and "nucleic acid sequences" refer to DNA, RNA and cDNA sequences.

The polynucleotides encoding EBF1 and EBF2 include the nucleotide sequences of SEQ ID NO: 1 and SEQ ID NO: 3, respectively. Nucleic acid sequences complementary to SEQ ID NOs: 1 and 3 are also encompassed within the present invention. A complementary sequence may include an antisense nucleotide. When the sequence is RNA, the deoxyribonucleotides A, G, C, and T of SEQ ID NOS: 1 and 3 are replaced by ribonucleotides A, G, C, and U, respectively. Also included in the invention are fragments ("probes") of the above-described nucleic acid sequences that are at least 15 bases in length, which is sufficient to permit the probe to selectively hybridize to DNA that encodes the protein of SEQ ID NO: 2 or SEQ ID NO: 4.

Nucleic acid sequences complementary to SEQ ID NOs: 1 and 3 are also encompassed within the present invention. A complementary sequence may include an antisense nucleotide. When the sequence is RNA, the deoxyribonucleotides A, G, C, and T of SEQ ID NOS: 1 and 3 are replaced by ribonucleotides A, G, C, and U, respectively. Also included in the invention are fragments ("probes") of the above-described nucleic acid sequences that are at least 15 bases in length, which is sufficient to permit the probe to selectively hybridize to DNA that encodes the protein of SEQ ID NO: 2 or SEQ ID NO: 4.

"Antisense" nucleic acids are DNA or RNA molecules that are complementary to at least a portion of a specific mRNA molecule (Weintraub, *Scientific American* 262 40, 1990). In the cell, the antisense nucleic acids hybridize to the corresponding mRNA, forming a double-stranded molecule. This interferes with the translation of the mRNA since the cell will not translate an mRNA that is double-stranded. Antisense oligomers of about 15 nucleotides are preferred, since they are easily synthesized and are less likely to cause non-specific interference with translation than larger molecules. The use of antisense methods to inhibit the in vitro translation of genes is well known in the art (Marcus-Sakura *Anal. Biochem.* 172: 289, 1998). In the present case, plants transformed with constructs containing antisense fragments of the EBF1 and/or EBF2 genes may display a modulated ethylene response.

Long double-stranded RNAs (dsRNAs; typically >200 nt) can be used to silence the expression of target genes in plants and plant cells. Upon introduction, the long dsRNAs enter the RNA interference (RNAi) pathway which involves the production of short (20-25 nucleotide) small interfering RNAs (siRNAs) and assembly of the siRNAs into RNA-induced silencing complexes (RISCs). The siRNA strands are then unwound to form activated RISCs. which cleave the target RNA. Double stranded RNA has been shown to be extremely effective in silencing a target RNA. Introduction of double stranded RNA corresponding to the EBF1 and/or EBF2 genes would be expected to modify the ethylene response of a plant, part of a plant, or a plant cell, as discussed herein, including, but not limited to, germination, flower and leaf senescence, fruit ripening, leaf abscission, root nodulation, programmed cell death, responsiveness to stress, responsiveness to pathogen attack, and the "triple response" of etiolated dicotyledoneous seedlings.

"Hybridization" refers to the process by which a nucleic acid strand joins with a complementary strand through base pairing. Hybridization reactions can be sensitive and selective so that a particular sequence of interest can be identified even in samples in which it is present at low concentrations. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 ng/ml sheared and denatured salmon sperm DNA. Hybridization could occur under medium stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art. "Selective hybridization" as used herein refers to hybridization under moderately stringent or highly stringent physiological conditions (See, for example, the techniques described in Maniatis et al., 1989 Molecular Cloning A Laboratory Manual, Cold Spring Harbor Laboratory, N.Y., incorporated herein by reference), which distinguishes EBF1 nucleotide sequences, or EBF2 nucleotide sequences.

In another aspect of the invention, very high stringency hybridization conditions can include at least one wash at 0.1×SSC, 0.1% SDS, at 60° C. for 15 minutes. High stringency hybridization conditions can include at least one wash at 0.2×SSC, 0.1% SDS, at 60° C. for 15 minutes. Moderate stringency hybridization conditions can include at least one wash at 0.5×SSC, 0.1% SDS, at 60° C. for 15 minutes. Low stringency hybridization conditions can include at least one wash at 1.0×SSC, 0.1% SDS, at 60° C. for 15 minutes.

Another aspect of the invention is polypeptides or fragments thereof which have at least about 70%, at least about 80%, at least about 85%, at least about 90%, at least about 95%, or more than about 95% homology to SEQ ID NO: 2 or SEQ ID NO: 4, and sequences substantially identical thereto, or a fragment including at least 5, 10, 15, 20, 25, 30, 35, 40, 50, 75, 100, or 150 consecutive amino acids thereof. Homology may be determined using any of the methods described herein which align the polypeptides or fragments being compared and determines the extent of amino acid identity or similarity between them. It will be appreciated that amino acid "homology" includes conservative amino acid substitutions such as those described above.

The polypeptides or fragments having homology to SEQ ID NO: 2, SEQ ID NO: 4, and sequences substantially identical thereto, or a fragment including at least about 5, 10, 15, 20, 25, 30, 35, 40, 50, 75, 100, or 150 consecutive amino acids thereof may be obtained by isolating the nucleic acids encoding them using the techniques described herein.

The homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to the polypeptide of SEQ ID NO: 2, SEQ ID NO: 4, and sequences substantially identical thereto, or a fragment including at least about 5, 10, 15, 20, 25, 30, 35, 40, 50, 75, 100, or 150 consecutive amino acids thereof using any of the programs described above.

Also included in embodiments of the invention are nucleotide sequences that are greater than 70% homologous with SEQ ID NO: 1 or SEQ ID NO: 3, but still retain the ability to modulate an aspect of the ethylene response such as germination, flower and leaf senescence, fruit ripening, fruit drop, leaf abscission, root nodulation, programmed cell death, responsiveness to stress, responsiveness to pathogen attack, and the "triple response" of etiolated dicotyledoneous seedlings. Other embodiments of the invention include nucleotide sequences that are greater than 75%, 80%, 85%, 90% or 95% homologous with SEQ ID NO: 1 or SEQ ID NO: 3, but still retain the ability to confer a modulated ethylene response.

SEQ ID NO: 5 includes a polynucleotide encoding EIN3, and SEQ ID NO: 6 includes the corresponding EIN3 protein sequence. This EIN3 protein is a representative member of the EIN3/EIL (EIN3-like) family of transcription factors that is involved in the ethylene response of plants, as described further herein. The EIN3 polynucleotide and protein sequences of SEQ ID NO: 5 and SEQ ID NO: 6 are *Arabidopsis* sequences. A protein involved in the ethylene response of a plant may be any transcription factor involved in the ethylene response of any plant. In particular, a protein involved in the ethylene response of a plant may be a transcription factor similar to the EIN3/EIL family of transcription factors. In some versions, a transcription factor similar to the EIN3/EIL family of proteins includes a polypeptide or fragment thereof which has at least about 70%, at least about 80%, at least about 85%, at least about 90%, at least about 95%, or more than about 95% homology to SEQ ID NO: 6 and sequences substantially identical thereto, or a fragment including at least 5, 10, 15, 20, 25, 30, 35, 40, 50, 75, 100, or 150 consecutive amino acids thereof. Homology may be determined using any of the alignment methods described herein which align the polypeptides or fragments being compared and determines the extent of amino acid identity or similarity between them. It will be appreciated that amino acid "homology" includes conservative amino acid substitutions such as those described herein.

Examples of orthologs of EIN3 (or other members of the EIN3/EIL family) that are involved in the ethylene response of plants have been found in many plants, including tobacco (e.g., NtEIL1), tomato (e.g., the LeEIL genes), mung bean (e.g., VR-EIL1 and VR-EIL2), and carnation (e.g., DC-EIL). Othologs of EIN3 may be present in other plant types. For example, plants having an ethylene response include, but are not limited to: dicotyledons and monocotyledons including but not limited to rice, maize, wheat, barley, sorghum, millet, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussel sprout, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, plums, cranberries, grapefruit, lemons, limes, nectarines, oranges, peaches, pears, tangelos, tangerines, carnation, chrysanthemum, petunia, rose, geranium, violet, gladioli, orchid, lilac, crabapple, sweetgum tree, maple tree, poinsettia, locust tree, oak tree, ash tree and linden tree. Any of these plants may include a protein involved in the ethylene response of the plant that interacts with protein encoded by an F-box gene. For example, any of these plants may include an EIN3 ortholog.

Specifically disclosed herein are cDNA sequences for EBF1 and EBF2. DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of the amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., *Nucl. Acid Res.* 9, 879, 1981). Alternatively, a subtractive library is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay, et al. *Nucl. Acid Res.*, 11, 2325, 1983).

A cDNA expression library, such as lamda gt11, can be screened indirectly for EBF peptides (e.g., EBF1 or EBF2) using antibodies specific for EBF1 and/or EBF2. Such antibodies can be either polyclonally or monoclonally derived and used to detect expression product indicative of the presence of EBF1 or EBF2 cDNA.

Another embodiment of the invention relates to plants that have at least one aspect of the ethylene response modulated. Such modifications might include effects on germination, flower and leaf senescence, fruit ripening, leaf abscission, root nodulation, programmed cell death, responsiveness to stress, responsiveness to pathogen attack, and other growth effects. Many of these aspects of the ethylene response have been well characterized. For example, see: U.S. Pat. No. 6,355,778 to Ecker et al.; U.S. Patent Application No. 20040128719 to Klee et al.; Bleecker, A. B. and Kende, H *Annu Rev Cell Dev Biol* 16, 1-18, 2000; and Johnson, P. R., and Ecker, J. R. *Annu Rev Genet,* 32, 227-254, 1998. Each of these references is herein incorporated by references in its entirety.

Specific modifications include transgenic plants with an altered ethylene response due to transformation with constructs using antisense or siRNA technology that affect transcription or expression from an F-box gene (or genes) such as EBF1 and/or EBF2. Such plants may have a reduced level of an F-box protein that interacts with a protein involved in the ethylene response of the plant, such as EIN3. Thus, the level of a protein involved in the ethylene response will increase since there may be less of the F-box protein to bind to the protein involved in the ethylene response (and thereby target this protein for degradation). For example, reducing the transcription or expression of EBF1 and/or EBF2 may result in an increase in the level of EIN3 in a plant. Increasing the level of EIN3 may enhance the plant's sensitivity to ethylene.

In addition, specific modifications include transgenic plants with an altered ethylene response due to transformation with constructs using over-expression of one or more F-Box genes that affect transcription or expression from an F-box gene (or genes) such as EBF1 and/or EBF2. Such plants may have a increased level of an F-box protein that interacts with a protein involved in the ethylene response of the plant, such as EIN3. Thus, the level of a protein involved in the ethylene response will decrease since there may be more of the F-box protein to bind to the protein involved in the ethylene response (and thereby target this protein for degradation). For example, increasing the transcription or expression of EBF1 and/or EBF2 may result in a decrease in the level of EIN3 in a plant. Decreasing the level of EIN3 may reduce the plant's sensitivity to ethylene.

Accordingly, in another series of embodiments, the present invention provides methods of screening or identifying proteins, small molecules or other compounds which are capable of inducing or inhibiting the expression of the F-box genes and proteins that interact with a protein involved in the ethylene response of a plant, portion of a plant, or plant cell. The assays may be performed in vitro using transformed or non-transformed cells, immortalized cell lines, or in vivo using transformed plant models enabled herein. In particular, the assays may detect the presence of increased or decreased expression of EBF (e.g., EBF1 and/or EBF2 from *Arabidopsis* or other plants) genes or proteins on the basis of increased or decreased mRNA expression, increased or decreased levels of EBF protein products, or increased or decreased levels of expression of a marker gene (e.g., beta-galactosidase, green fluorescent protein, alkaline phosphatase or luciferase) operably joined to an EBF 1 or EBF2 5' regulatory region in a recombinant construct. A plant, portions of a plant, or plant cells known to express a particular EBF, or transformed to express a particular EBF, may be incubated with one or more test compounds (e.g., added to the medium). After allowing a sufficient period of time (e.g., 0-72 hours) for the compound to induce or inhibit the expression of the F-box protein (e.g., EBF1 and/or EBF2), any change in levels of expression from an established baseline may be detected using any of the techniques described above.

In another series of embodiments, the present invention provides methods for identifying proteins and other compounds which bind to, or otherwise directly interact with, F-box proteins that interact with proteins involved in the ethylene response, such as EBF1 and/or EBF2. The proteins and compounds include endogenous cellular components which interact with these F-box proteins in vivo and which, therefore, provide new targets for agricultural products, as well as recombinant, synthetic and otherwise exogenous compounds which may bind an F-box protein (e.g. EBF1 or EBF2) and, therefore, are candidates for modulating the ethylene response (or some aspect of the ethylene response) in a plant. Thus, in one series of embodiments, High Throughput Screening-derived proteins, DNA chip arrays, cell lysates or tissue homogenates may be screened for proteins or other compounds which bind to one of the normal or mutant EBF genes. Alternatively, any of a variety of exogenous compounds, both naturally occurring and/or synthetic (e.g., libraries of small molecules or peptides), may be screened for EBF binding capacity.

Compound sources libraries may be used to screen for compounds that modulate or interact with EBF1, EBF2, and other F-box proteins that interact with proteins involved in the ethylene response. For example, screening with libraries of chemical compounds may be done using commercially available libraries or specially constructed libraries. Such libraries may contain known structures and de novo designs (including enumerated combinatorial libraries). Libraries may be combinatorial libraries, or historical collections of compounds, or may be a combination thereof. Historical collections are typically "targeted" libraries that are derived from classical medicinal chemicals or other known compounds, most of which have very well-defined chemical characteristics. Sources of commercially available compound libraries include: ChemBridge (San Diego, Calif., U.S.A.); Timtec (Wilmington, Del., U.S.A.); Maybridge Ltd. (Cornwall, U.K.); Ryan Scientific (Isle of Palms, S.C., U.S.A.); and CEREP, (Redmond, Wash., U.S.A.).

Virtual screening (also referred to as in silico screening) may be used to identify compounds that modulate EBF1, EBF2, and other F-box proteins of interest. In virtual screening, databases of known structures and new structures (including enumerated combinatorial libraries) are screened against characteristic properties of the target (e.g., EBF1 or EBF2). Commercially available databases that may be employed for virtual screening may be available from: Molecular Design Limited (San Leandro, Calif., U.S.A.); Beilstein Informationssysteme GmbH (Frankfurt, Germany); CSD Systems (Cambridge, UK); Daylight Chemical Information Systems Inc. (Claremont, Calif., U.S.A.); and Derwent Information (London, U.K.).

In many embodiments, an assay is conducted to detect binding between the F-box protein and another moiety. The F-box protein in these assays may be, for example, EBF1 or EBF2, and may include or derived from a normal or mutant EBF1 or EBF2 protein, including functional domains or antigenic determinants of EBF1 or EBF2. Binding may be detected by non-specific measures (e.g., transcription modulation, altered chromatin structure, peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. Some appropriate methods involve variations on the following techniques: (1) direct extraction by affinity chromatography; (2) co-isolation of F-box (e.g., EBF1 or EBF2) components and bound proteins or other compounds by immunoprecipitation; (3) BIAcore analysis; and (4) the yeast two-hybrid systems.

Embodiments of the invention also include methods of identifying proteins, small molecules and other compounds capable of modulating the activity of normal or mutant F-box proteins such as EBF1 and EBF2. The present invention may use normal cells or plants (or portions of plants), the transformed cells and plant models of the present invention, or cells obtained from plants bearing normal or mutant F-box genes. The present invention provides methods of identifying compounds capable of modulating the expression or activity of an F-box gene (e.g., EBF1 or EBF2), and therefore modulating the ethylene response. A compounds may be identified based on the compound's ability to affect the expression of the F-box gene whose product interacts with a protein involved in the ethylene response of a plant; the ability of the F-box gene to interact with a protein involved in the ethylene response of a plant; the activity of other genes regulated by these F-box proteins; the activity of proteins that interact with normal or mutant F-box proteins that interact with a protein involved in the ethylene response of a plant; the intracellular localization of these F-box proteins; changes in transcription activity; changes in ubiquitination; changes in the activity of the ubiquitin/proteosome pathway; or other biochemical, histological, or physiological markers which distinguish cells bearing normal and modulated activity of F-box proteins that interact with proteins involved in the ethylene response in plants.

In accordance with another aspect of the invention, the proteins of the invention can be used as starting points for rational chemical design to provide ligands or other types of small chemical molecules. Alternatively, small molecules or other compounds identified by the above-described screening assays may serve as "lead compounds" in design of modulators of the ethylene response (or aspects of the ethylene response) in plants.

DNA sequences encoding F-box proteins such as EBF1 and EBF2 can be expressed in vitro by DNA transfer into a suitable host cell. "Host cells" are cells in which a vector can be propagated and its DNA expressed. The term also includes any progeny or graft material, for example, of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

As part of the present invention, the F-box (e.g., EBF1 and/or EBF2) polynucleotide sequences may be inserted into a recombinant expression vector. The terms "recombinant expression vector" or "expression vector" refer to a plasmid, virus or other vehicle known in the art that has been manipulated by insertion or incorporation of the F-box genetic sequence. Such expression vectors contain a promoter sequence which facilitates the efficient transcription of the inserted F-box gene sequence. The expression vector typically contains an origin of replication, a promoter, as well as specific genes which allow phenotypic selection of the transformed cells.

Methods which are well known to those skilled in the art can be used to construct expression vectors containing the EBF1 and/or EBF2 coding sequences and appropriate transcriptional/translational control signals. These methods include in vitro recombinant DNA techniques, synthetic techniques, and in vivo recombination/genetic techniques.

A variety of host-expression vector systems may be utilized to express the EBF1 and/or EBF2 coding sequence. These include but are not limited to microorganisms such as bacteria transformed with recombinant bacteriophage DNA, plasmid DNA or cosmid DNA expression vectors containing the EBF1 and/or EBF2 coding sequence; yeast transformed with recombinant yeast expression vectors containing the EBF1 and/or EBF2 coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the EBF1 and/or EBF2 coding sequence; insect cell systems infected with recombinant virus expression vectors (e.g., baculovirus) containing the EBF1 and/or EBF2 coding sequence; or animal cell systems infected with recombinant virus expression vectors (e.g., retroviruses, adenovirus, vaccinia virus) containing the EBF1 and/or EBF2 coding sequence, or transformed animal cell systems engineered for stable expression.

Depending on the host/vector system utilized, any of a number of suitable transcription and translation elements, including constitutive and inducible promoters, transcription enhancer elements, transcription terminators, etc. may be used in the expression vector (see e.g., Bitter et al. *Methods in Enzymology* 153, 516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the inserted EBF1 or EBF2 coding sequence.

Isolation and purification of recombinantly expressed polypeptide, or fragments thereof, may be carried out by conventional means including preparative chromatography and immunological separations involving monoclonal or polyclonal antibodies.

In another embodiment, the invention provides a method for producing a genetically modified plant having at least one modulated aspect of the ethylene response compared to a plant which has not been genetically modified (e.g., a wild-type plant). The method includes the steps of contacting a plant cell with at least one recombinant nucleic acid that alters the expression of an F-box gene. The F-box gene may include, for example, the EBF1 or EBF2 gene, or a mutant, homolog or fragment of EBF1 and/or EBF2. The nucleic acid sequence may be operably associated with a promoter, to obtain a transformed plant cell. A plant may be produced from the transformed plant cell; and thereafter a plant exhibiting a modulated response to ethylene may be selected.

Transgenic plants that result in at least one modulated aspect of the ethylene response may be obtained by reduced expression of the F-box gene. Thus, one embodiment of the invention includes plants transformed with antisense polynucleotides complementary to the EBF1 and/or EBF2 gene or fragments thereof wherein production of the antisense polynucleotides results in reduced expression of the EBF1 and/or EBF2 gene. In an alternate embodiment, reduced expression of EBF1 and/or EBF2 may also be achieved by methods such as cosuppression (Hooper, C. *J. NIH Res.* 3, 49-54, 1991) by operatively linking a truncated form of an F-box gene that interacts with a protein involved in the ethylene response to a promoter.

Transgenic plants that result in at least one modulated aspect of the ethylene response may be obtained by increased expression of the F-box gene. Thus, one embodiment of the invention includes plants transformed with polynucleotides encoding the EBF1 and/or EBF2 gene or fragments thereof wherein production of the polynucleotides results in increased expression of the EBF1 and/or EBF2 gene. Such plants might be expected to display a modulated ethylene response such as ethylene insensitivity.

The term "genetic modification" as used herein refers to the introduction of one or more heterologous nucleic acid sequences, e.g., an EBF1, EBF2, EBF1 mutant, or an EBF2 mutant encoding sequence, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed including multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, potato, rapeseed, field beans, soybeans, peppers, lettuce, peas, alfalfa, clover, cole crops or *Brassica oleracea* (e.g., cabbage, broccoli, cauliflower, brussels sprouts), radish, carrot, beets, eggplant, spinach, cucumber, squash, melons, cantaloupe, sunflowers and various ornamentals. Woody species include poplar, pine, *sequoia*, cedar, oak, etc.

The term "exogenous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In one embodiment, at least one nucleic acid sequence encoding the F-box protein (e.g., EBF1 or EBF2) or a variant thereof is operably linked with a promoter. It may be desirable to introduce more than one copy of a polynucleotide into a plant for enhanced expression. For example, introduction of multiple copies of the gene (e.g., the gene encoding an F-box protein that interacts with a protein involved in the ethylene response) would have the increase production of the gene product in the plant. Such a plant would have a reduced sensitivity to ethylene.

Genetically modified plants of the present invention are produced by contacting a plant cell with a recombinant nucleic acid including at least one nucleic acid sequence encoding an F-box protein that interacts with a protein involved in the ethylene response (e.g., EBF1 and/or EBF2) or a variant thereof. To be effective, once introduced into plant cells the nucleic acid sequence may be operably associated with a promoter which is effective in the plant cell to cause transcription of the F-box gene. Additionally, a polyadenylation sequence or transcription control sequence, also recognized in plant cells, may also be employed. It is preferred that the vector harboring the nucleic acid sequence to be inserted also contain one or more selectable marker genes so that the transformed cells can be selected from non-transformed cells in culture, as described herein.

The term "operably linked" refers to a functional linkage between a promoter sequence and a nucleic acid sequence regulated by the promoter. The operably linked promoter controls the expression of the nucleic acid sequence.

The expression of structural genes may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al. *Nature,* 310, 511, 1984; and Odell, et al. *Nature,* 313, 810, 1985); the full-length transcript promoter from Figwort Mosaic Virus (FMV) (Gowda, et al. *J. Cell Biochem.* 13D, 301, 1989) and the coat protein promoter to TMV (Takamatsu, et al. *EMBO J.* 6, 307, 1987). Alternatively, plant promoters such as the light-inducible promoter from the small subunit of ribulose bis-phosphate carboxylase (ssRUBISCO) (Coruzzi, et al. *EMBO J.* 3, 1671, 1984; and Broglie, et al., Science 224, 838, 1984); mannopine synthase promoter (Velten, et al. *EMBO J.* 3, 2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al. *Mol. Cell. Biol.* 6, 559, 1986; and Severin, et al. *Plant Mol. Biol.* 15, 827, 1990) may be used.

Promoters useful in the invention include both natural constitutive and inducible promoters as well as engineered promoters. Such inducible promoters can be turned on and off. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al. *Proc. Natl. Acad. Sci., U.S.A.* 90, 4567, 1993); In2-1 and In2-2 regulator sequences which are activated by substituted benzenesulfonamides, e.g., herbicide safeners (Hershey, et al. *Plant Mol. Biol.* 17, 679, 1991); and the GRE regulatory sequences which are induced by glucocorticoids (Schena, et al. *Proc. Natl. Acad. Sci., U.S.A.* 88, 10421, 1991). Other promoters, both constitutive and inducible will be known to those of skill in the art.

The particular promoter selected should be capable of causing sufficient expression to result in the production of an effective amount of gene product to modulate the ethylene response of a plant. The promoters used in the vector constructs of the present invention may be modified, if desired, to affect their control characteristics.

Tissue specific promoters may also be utilized in the present invention. An example of a tissue specific promoter is the promoter active in shoot meristems (Atanassova, et al. *Plant J.* 2, 291, 1992). Other tissue specific promoters useful in transgenic plants, including the cdc2a promoter and cyc07 promoter, will be known to those of skill in the art. (See for example, Ito, et al. *Plant Mol. Biol.* 24, 863, 1994; Martinez, et al. *Proc. Natl. Acad. Sci. USA* 89, 7360, 1992; Medford, et al. *Plant Cell* 3, 359, 1991; Terada, et al. *Plant Journal* 3, 241, 1993; Wissenbach, et al. Plant Journal 4, 411, 1993).

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthine-guanine phospho-ribosyltransferase and aminoglycoside 3'-O-phospho-transferase II (kanamycin, neomycin and G418 resistance). Other suitable markers will be known to those of skill in the art.

Vector(s) employed in the present invention for transformation of a plant cell include a nucleic acid sequence encoding an F-box gene (e.g., EBF1 and/or EBF2), operably linked to a promoter. To commence a transformation process in accordance with the present invention, it is first necessary to construct a suitable vector and properly introduce it into the plant cell. Details of the construction of vectors utilized herein are known to those skilled in the art of plant genetic engineering.

The nucleic acid sequences utilized in the present invention can be introduced into plant cells using Ti plasmids of *Agrobacterium tumefaciens*, root-inducing (Ri) plasmids, and plant virus vectors. (For reviews of such techniques see, for example, Weissbach & Weissbach, *Methods for Plant Molecular Biology*, Academic Press, NY, Section VIII, pp. 421-463, 1988; and Grierson & Corey, *Plant Molecular Biology*, 2d Ed., Blackie, London, Ch. 7-9, 1998; and Horsch, et al. *Science,* 227, 1229, 1985, both incorporated herein by reference). In addition to plant transformation vectors derived from the Ti or root-inducing (Ri) plasmids of *Agrobacterium*, alternative methods may involve, for example, the use of liposomes, electroporation, chemicals that increase free DNA uptake, transformation using viruses or pollen and the use of microprojection.

One of skill in the art will be able to select an appropriate vector for introducing the F-box-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, *Methods of Enzymology*, Vol. 153, 1987, Wu and Grossman, Eds., Academic Press, incorporated herein by reference). As used herein, the term "transformation" means alteration of the genotype of a host plant by the introduction of an F-box gene or a mutant F-box nucleic acid sequence.

For example, an EBR1 and/or an EBF2 nucleic acid sequence can be introduced into a plant cell utilizing *Agrobacterium tumefaciens* containing the Ti plasmid, as mentioned briefly above. In using an *A. tumefaciens* culture as a transformation vehicle, it is most advantageous to use a non-oncogenic strain of *Agrobacterium* as the vector carrier so that normal non-oncogenic differentiation of the transformed tissues is possible. It is also preferred that the *Agrobacterium* harbor a binary Ti plasmid system. Such a binary system includes 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, *Biotechnology,* 1, 262, 1983; Hoekema, et al., *Nature,* 303, 179, 1983). Such a binary system is preferred because it does not require integration into the Ti plasmid of *Agrobacterium*.

Methods involving the use of *Agrobacterium* in transformation according to the present invention include, but are not limited to: 1) co-cultivation of *Agrobacterium* with cultured isolated protoplasts; 2) transformation of plant cells or tissues with *Agrobacterium*; or 3) transformation of seeds, apices or meristems with *Agrobacterium*.

In addition, gene transfer can be accomplished by in planta transformation by *Agrobacterium*, as described by Bechtold, et al., (C. R. Acad. Sci. Paris, 316:1194, 1993). This approach is based on the vacuum infiltration of a suspension of *Agrobacterium* cells.

One method of introducing F-box-encoding nucleic acid (e.g., EBF1 and/or EBF2) into plant cells is to infect such plant cells, an explant, a meristem or a seed, with transformed *Agrobacterium tumefaciens* as described above. Under appropriate conditions known in the art, the transformed plant cells are grown to form shoots, roots, and develop further into plants.

Alternatively, nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

Nucleic acid sequences can also be introduced into plant cells by electroporation (Fromm, et al., Proc. Natl. Acad. Sci., U.S.A., 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing nucleic acid into a plant cell is high velocity ballistic penetration by small particles with the nucleic acid to be introduced contained either within the matrix of such particles, or on the surface thereof (Klein, et al., Nature 327:70, 1987). Bombardment transformation methods are also described in Sanford, et al. (Techniques 3:3-16, 1991) and Klein, et al. (Bio/Techniques 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing nucleic acid material into the plant cell, including chemical and physical means as described above. Preferably, contacting refers to introducing the nucleic acid or vector into plant cells (including an explant, a meristem or a seed), via *Agrobacterium tumefaciens* transformed with the encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see Methods in Enzymology, Vol. 118 and Klee, et al., Annual Review of Plant Physiology, 38:467, 1987). Utilizing the leaf disk-transformation-regeneration method of Horsch, et al., Science, 227:1229, 1985, disks are cultured on selective media, followed by shoot formation in about 2-4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g. altered time to flowering.

Parts obtained from regenerated plant, such as flowers, seeds, leaves, branches, roots, fruit, and the like are included in the invention, provided that these parts include cells that have been transformed as described. Progeny and variants, and mutants of the regenerated plants are also included within the scope of the invention, provided that these parts include the introduced nucleic acid sequences.

Plants exhibiting a modulated ethylene response such (e.g., the "triple response" of etiolated dicotyledoneous seedlings) as compared with wild-type plants can be selected by visual observation. The invention includes plants produced by the method of the invention, as well as plant tissue and seeds. Stem shape and size may be observed visually or preferably may be determined quantitatively by measuring with a ruler or with a video-imaging system. Fruit drop can be measured before and after treatment. Sugar content of ripening fruit. Enzymes levels can be moderated.

In yet another embodiment, the invention provides a method for producing a genetically modified plant cell such that a plant produced from the cell has a modulated ethylene sensitivity compared with a wild-type plant. The method includes contacting the plant cell with an nucleic acid sequence that alters the expression of an F-box gene, wherein the F-box gene encodes a first protein that interacts with a second protein involved in the ethylene response of the plant, to obtain a transformed plant cell. The method may also include growing the transformed plant cell under plant forming conditions to obtain a plant having a modulated ethylene response. Conditions such as environmental and promoter inducing conditions vary from species to species, but should be the same within a species.

F-Box Proteins and the Ubiquitin/Proteosome Pathway

The ubiquitin/proteasome pathway of protein degradation is typically controlled by the ubiquitin-ligating SCF (SKP1/

Cullin/F-box protein) complex. The F-box proteins confer substrate specificity to the SCF complex and the ubiquitin/proteasome pathway. F-box proteins mediate substrate selectivity by binding to the target protein that will later be degraded by the proteasome.

In *Arabidopsis*, over 1000 F-box motif-containing proteins have been identified. Members of the F-box protein family typically contain a conserved 40-50 amino acid F-box motif. The lack of a strict consensus may make identification by eye difficult, therefore it may be necessary to use search algorithms to detect F-boxes. F-box proteins may also include motifs capable of protein-protein interaction, which may recruit specific substrates to the SCF complex.

The SCF complex was first identified in yeast and includes four subunits: Skp1, Cullin, Roc1/Rbx1/Hrt1 and an F-box protein. The first three proteins form a common scaffold onto which different F-box proteins can be assembled. The F-box protein may confer specificity to the SCF complex. SCF complexes may be designated by their associated F-box protein, for example, $SCF^{EBF1}$ and $SCF^{EBF2}$. The F-box motif may interact with the Skp1 component. ASK1 is the *Arabidopsis* ortholog of the SKP protein.

As described herein, F-box proteins may interact (e.g., by targeting for degredation) with proteins involved in the ethylene response. In particular, a subset of F-box proteins, called EBF ("EIN3 binding F-box") proteins, may interact with the transcription factor EIN3, and related proteins (e.g., homologs, orthologs, etc.). Although two particular F-box proteins, ERB1 and ERB2 are characterized here, additional F-box proteins, including additional EBF proteins, are intended to be within the scope of this invention.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

EXAMPLES

Example 1

The Level of EIN3 Protein is Controlled by Ethylene

EIN3 is a key transcription factor positively regulating gene expression in response to ethylene. We sought to investigate how EIN3 is regulated by ethylene. Overexpression of EIN3 (EIN3ox) in transgenic plants results in constitutive ethylene responses, implying that EIN3 abundance is important for its function. However, previous studies revealed that the level of EIN3 RNA is not altered either by ethylene treatment, or in the ein2 or ctr1 mutant, suggesting a post-transcriptional mechanism on EIN3 regulation by ethylene. To determine whether the level of EIN3 protein is subject to ethylene regulation, we first monitored the levels of EIN3 protein in wild-type plants grown in growth medium supplemented with various concentrations of ACC, an ethylene biosynthetic precursor. As shown in FIG. 1A, we observed a positive correlation between the levels of EIN3 protein and the severity of the seedling triple response phenotype. In the absence of ACC treatment, EIN3 protein was barely detectable. By comparison, the levels of EIN3 protein in plants treated with high concentrations of ACC (e.g. 10 and 50 µM) were dramatically elevated. To gain further insight into the kinetics of EIN3 induction by ethylene, we monitored the levels of EIN3 protein in plants treated with ethylene gas for different periods of time. In wild-type plants, the level of EIN3 markedly increased after 1 hr of hormone treatment (FIG. 1B). No EIN3 protein was observed in the ein3-1 mutant, confirming that our antibody specifically recognized EIN3 protein. The levels of transgenically overexpressed EIN3 protein in EIN3ox plants were also up-regulated by ethylene treatment (FIG. 1B). In agreement with this observation, EIN3ox seedlings displayed an extremely exaggerated triple response (with a very short root and hypocotyl) in the presence of ethylene (see FIGS. 5C and 5D). Taken together, we conclude that the levels of both endogenous and transgenically overexpressed EIN3 protein are increased by ethylene.

Example 2

Components of the Ethylene Signaling Pathway Are Required for EIN3 Accumulation

Genetic studies have identified several components of the ethylene signaling pathway, including the ETR/ERS family of receptors, CTR1, EIN2, EIN5, and EIN6 (Stepanova and Ecker, 2000). We asked whether any of these signaling components are required for ethylene-induced EIN3 accumulation. Silver ion is a potent inhibitor of ethylene action that acts by interfering with ethylene perception (Abeles et al., *Ethylene in Plant Biology, Second Edition*, 1992). We tested whether silver treatment perturbs EIN3 accumulation upon ethylene treatment. As shown in FIG. 1C, the level of EIN3 was no longer induced by ethylene in wild-type seedlings treated with silver ion. This result indicates that perception of ethylene is required for EIN3 accumulation. We next monitored the levels of EIN3 protein in several ethylene-insensitive mutants, including two dominant receptor mutants, etr1 and ein4, as well as three recessive mutants, ein5, ein6, and ein2. When compared with wild-type seedlings, ein4, ein5, or ein6 mutants showed a significant delay in EIN3 accumulation in response to ethylene and also a reduction in maximal accumulation (FIGS. 1D and 1E). In etr1, EIN3 did not accumulate until 12 hr of treatment and the protein level was only slightly elevated. However, in ein2, ethylene-induced EIN3 accumulation was completely blocked. We were unable to detect any EIN3 protein in ein2 seedlings treated with ethylene even after 3 days of continuous hormone treatment (data not shown). These results demonstrate that an intact ethylene signaling pathway consisting of the ETR/ERS receptors, EIN2, EIN5 and EIN6 is required for EIN3 accumulation, suggesting that these components function upstream of EIN3. Moreover, these results imply that the ethylene-insensitivity observed in these mutants (etr1, ein2, ein4, ein5, ein6) might be the consequence of reduced EIN3 abundance.

In contrast to the ethylene-insensitive mutants, the ctr1 and eto mutants display constitutively activated ethylene responses (Kieber et al., *Cell* 72, 427-441 1993). Consistent with its phenotype, ctr1 expressed a higher level of EIN3 in comparison with wild type when no exogenous ethylene was applied (FIG. 1F). Interestingly, the level of EIN3 in ctr1 remained inducible by ethylene. Given that ctr1-1 produces a non-functional CTR1 protein (Huang et al., 2003), this result suggests that a parallel pathway, bypassing CTR1, might exist. We also observed elevated EIN3 protein levels in eto1 and eto2 mutants in the absence of exogenous ethylene (data not shown). Thus, the constitutive triple response mutants result in elevated levels of EIN3 protein.

Example 3

EIN3 Protein is Rapidly Degraded by a Proteasome-Mediated Pathway

Figure 2:
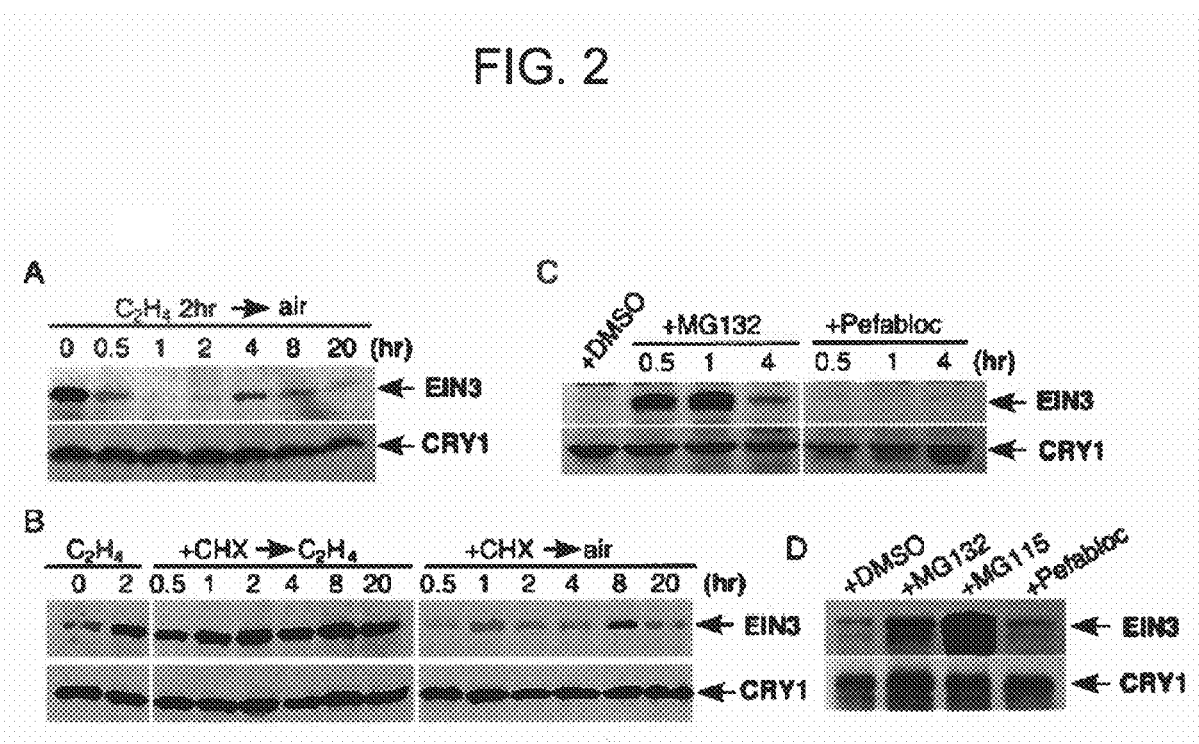
FIGS. 2A-2D show that the EIN3 protein is rapidly degraded through a proteasome-dependent pathway. (A) EIN3 protein is unstable in the absence of ethylene. Etiolated wild-type seedlings grown in the air were treated with ethylene for 2 hr (indicated by time point 0) and subsequently moved back to hydrocarbon-free air for the indicated amounts of time. Total protein extracts were subjected to immunoblot assays. (B) Ethylene treatment stabilizes EIN3 protein. Ethylene-pretreated wild-type seedlings were supplemented with 100 µM of cycloheximide (CHX) and then transferred into either ethylene or hydrocarbon-free air for the indicated amounts of time. (C) EIN3 protein is stabilized by specific proteasome inhibitors. Arabidopsis suspension cells were treated with mock (1% DMSO), MG132 (50 µM), or Pefabloc SC (100 µM) for the indicated amounts of time before cells were harvested for immunoblot assays. (D) Etiolated EIN3ox seedlings grown in the air were treated with mock (1% DMSO), MG132 (50 µM), MG115 (50 µM) or Pefabloc SC (100 µM) for 4 hr.

As the level of EIN3 is low in the absence of ethylene, we asked whether EIN3 protein is unstable in this condition. After boosting EIN3 levels in wild-type seedlings by ethylene treatment, seedlings were placed in a stream of hydrocarbon-free air and level of EIN3 protein was monitored. As shown in FIG. 2A, EIN3 levels dramatically decreased after 30 min and remained barely detectable for the subsequent 2 hr. Interestingly, after 4 hr in the air, EIN3 protein started to re-accumulate to a modest level. These results suggested that, in the absence of ethylene, EIN3 is a short-lived protein.

We next examined how ethylene evokes EIN3 protein accumulation. The rapid increase in EIN3 protein accumulation upon ethylene treatment could be attributed either to ethylene-induced de novo protein synthesis, or to ethylene-directed repression of constitutive EIN3 protein turnover, or to a combination of both processes. To address this issue, we blocked de novo translation initiation using cyclohexamide (CHX) and compared the levels of EIN3 protein in the presence or absence of ethylene. After 2 hr of hormone treatment, seedlings were incubated with CHX and kept in either ethylene or hydrocarbon-free air. As shown in FIG. 2B, the levels of EIN3 remained constitutively high in the presence of ethylene but decreased rapidly in the absence of ethylene, indicating that new protein synthesis is not required for ethylene-mediated EIN3 protein accumulation. Thus, we conclude that ethylene acts to repress constitutive degradation of EIN3 protein, although we cannot rule out the possibility that translational regulation may play a minor role in ethylene-mediated EIN3 accumulation.

The ubiquitin/proteasome pathway is involved in the rapid degradation of many short-lived proteins that regulates numerous cellular processes (Hochstrasser, *Annu Rev Genet.* 30, 405-439, 1996). Because EIN3 turnover is rapid, we speculated that a proteasome-mediated pathway might be responsible for its degradation. To test this possibility, we treated *Arabidopsis* suspension cell cultures with proteasome-specific inhibitors, MG132 and MG115 (Lee and Goldberg, *Trends Cell Biol* 8, 397-403, 1998). After 30 min of MG132 treatment, the levels of EIN3 protein markedly increased (FIG. 2C). Likewise, MG115 treatment also enhanced EIN3 abundance (data not shown). As a control, treatment with a general cysteine protease inhibitor, Pefabloc, had no effect on EIN3 abundance (FIG. 2C). We further demonstrated that the abundance of transgenically overexpressed EIN3 protein was similarly induced by treatment with MG132 or MG115, but not with Pefabloc (FIG. 2D). These results indicate that EIN3 proteolysis is proteasome-dependent.

Example 4

Ethylene or MG132 Treatment Promotes the Nuclear Accumulation of EIN3 Protein EIN3 is localized in the nucleus in transiently transformed protoplast cells (Chao et al., *Cell* 89, 1133-1144, 1997). To assess whether the nuclear localization of EIN3 is modulated by ethylene, we made transgenic *Arabidopsis* plants that express an EIN3-GFP fusion protein driven by the constitutive CaMV 35S promoter. Overexpression of EIN3-GFP was able to complement the ein3 mutant (data not shown), indicating that this fusion protein was functional in plants. Immunoblot analysis indicated that the level of EIN3-GFP fusion protein was dramatically increased by ethylene (FIG. 3A). We also observed that treatment with ACC substantially enhanced the abundance of EIN3-GFP in the nucleus (as visualized by DAPI staining; data not shown) (FIG. 3B). To gain a more dynamic view of how ethylene may trigger EIN3-GFP nuclear accumulation, we conducted a time-course study. As shown in FIG. 3C, while barely detected in the absence of ACC treatment, EIN3-GFP accumulated in the nucleus after 1 hr of ACC treatment (but not in mock treated cells, data not shown), and nuclear accumulation continued for at least 4 hr. We next asked whether inhibition of proteasome-mediated proteolysis by MG132 treatment is sufficient for EIN3-GFP to accumulate in the nucleus. Similar to ethylene, treatment of seedling with MG132 also led to rapid nuclear accumulation of EIN3-GFP in the absence of ethylene (FIG. 3D). Taken together, we conclude that accumulation of the transcriptional regulator EIN3 in the nucleus is promoted by ethylene or by inhibition of proteasome function.

Example 5

Two F-Box Proteins, EBF1 and EBF2, Interact with EIN3

Figure 4C:
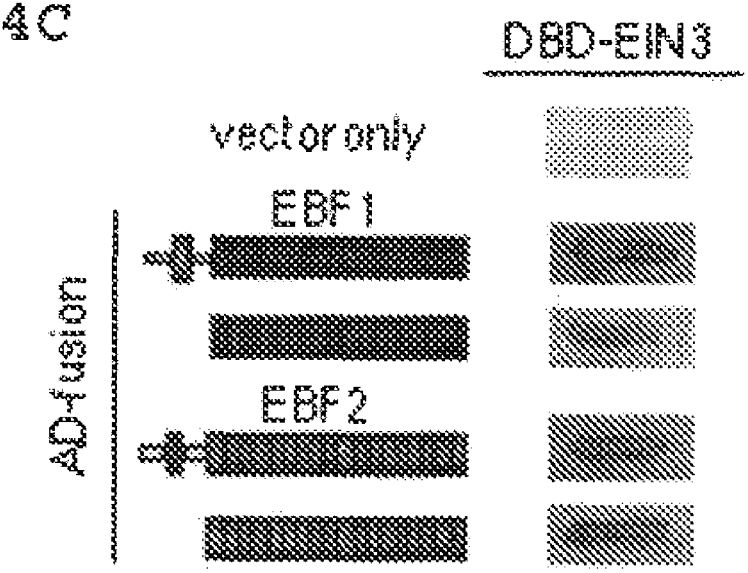
Figure 4D:
Figure 4E:
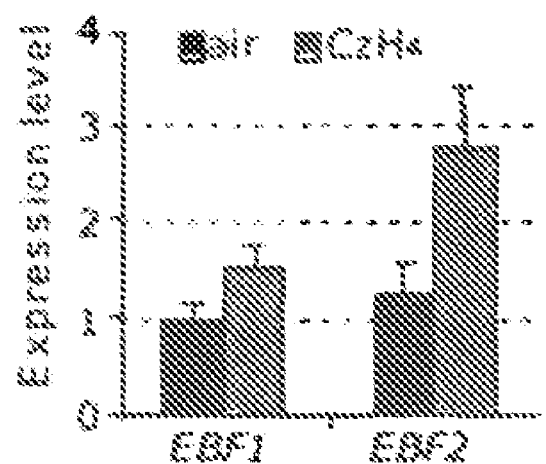

Several F-box proteins have recently been identified as key regulators of plant hormone signaling pathways (Frugis and Chua, *Trends Cell Biol* 12, 308-311, 2002; Vierstra, *Trends Plant Sci* 8, 135-142, 2003). Because EIN3 abundance is regulated by a proteasome-dependent pathway, we speculated that one or more specific F-box proteins would mediate the EIN3 degradation process. While there are approximately 700 putative F-box proteins in the *Arabidopsis* genome, only a few of them have been functionally characterized (Gagne et al., *Proc Natl Acad Sci* 99, 11519-11524, 2002). Using the EIN3 N-terminal domain as bait in yeast two-hybrid screen, we failed to identify any F-box protein that could interact with EIN3. We then directly tested the possible interaction between EIN3 full-length protein and individual F-box proteins. Using genome-wide microarray experiments, we narrowed the search for EIN3-interacting F-box proteins by first testing those genes whose RNA levels were regulated by ethylene (Alonso et al., *Science* 301, 653-657, 2003; H. G. and J. R. E., unpublished data). From this gene list, two closely related candidate F-box proteins were identified which were able to interact with EIN3 in yeast two-hybrid assays (FIGS. 4C and 4E). We designated these two F-box proteins as EBF1 and EBF2 (for EIN3-binding F-box protein 1 and 2). EBF1 was previously named as FBL6 with no function assigned (Xiao and Jang, 2000). These two proteins share 57% identity in amino acid sequence (FIG. 4A), and each contains a well-conserved F-box motif in the amino-terminus and 18 tandem leucine-rich repeats (LRRs) in the carboxyl terminus (FIGS. 4A and 4B). Because LRR domains in several F-box proteins contribute to the substrate binding (Gagne et al., *Proc Natl Acad Sci* 99, 11519-11524, 2002), we tested whether the C-terminal LRR domains in EBF1 and EBF2 were sufficient for EIN3 interaction. As shown in FIG. 4C, both LRR domains interacted with EIN3 protein in yeast two-hybrid assays. A truncated fragment including only the first or the last 9 LRRs of EBF1 failed to interact with EIN3 (data not shown), suggesting that the entire LRR domain might be required for EIN3 binding. We also found that EIN3 C-terminal domain is required for EBF1/EBF2 binding (data not shown), providing an explanation for the failure of identifying these two F-box proteins in the previous yeast two-hybrid screen. To examine whether EBF1 and EBF2 function as authentic F-box proteins, which characteristically associate with Skp1 proteins (Deshaies, *Annu Rev Cell Dev Biol* 15, 435-467, 1999), we tested the interaction between the two proteins and ASK1, an *Arabidopsis* Skp1 protein. Both F-box proteins were able to interact with ASK1 in yeast two-hybrid assays (FIG. 4D). Taken together, we identified two EIN3-interacting F-box proteins as candidates for SCF-mediated targeting of EIN3 protein turnover.

Figure 5:
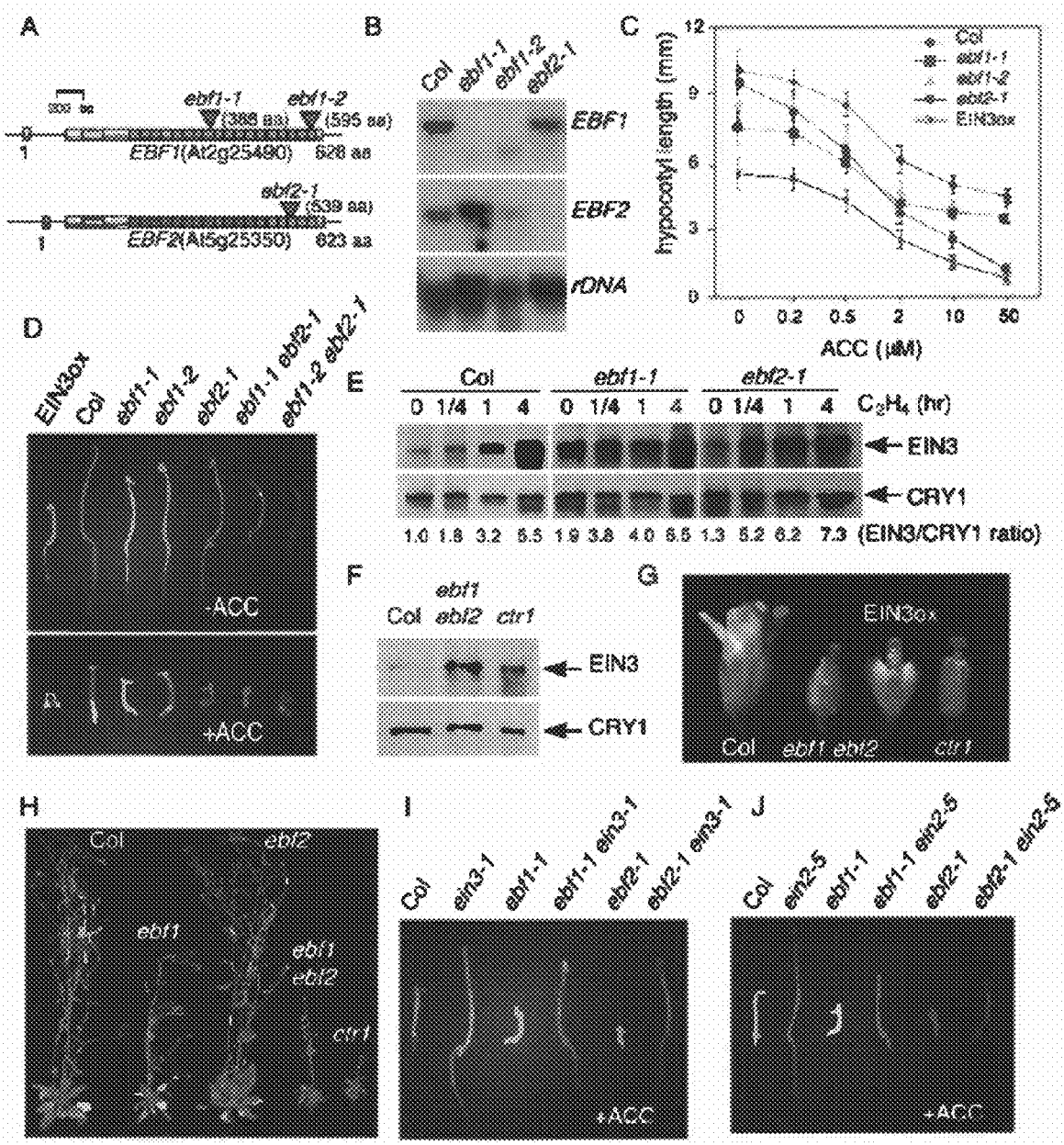
FIGS. 5A-5J show that mutations in the EBF1 and/or EBF2 F-box genes result in hypersensitivity to ethylene and elevated accumulation of EIN3 protein. (A) Schematic diagram of the EBF1 and EBF2 mutations. Coding regions are represented by boxes while non-coding regions are indicated by lines. F-box and LRR motifs are shaded light and dark, respectively. A triangle represents a T-DNA insertion event whose position is indicated. (B) Northern blot analysis of Col, ebf1-1, ebf1-2, and ebf2-1 seedlings. (C) Dosage response of EBF1 and EBF2 mutants. Etiolated seedlings were grown on MS medium supplemented with various concentrations of ACC for 3 days. The length of hypocotyls from 10 seedlings was measured, and the mean values and standard deviations were plotted. (D) Phenotype of 3-day-old etiolated seedlings grown on MS medium supplemented without or with 10 μM of ACC. (E) Immunoblot assays of EIN3 protein in the F-box mutants. The relative intensity of the EIN3 protein was calculated by normalization of the intensity of EIN3 bands with the intensity of the corresponding CRY1 bands. (F) Immunoblot assays of EIN3 protein in 2-week-old light-grown Col, ebf1 ebf2, and ctr1 plants. (G) Comparison of Col, ebf1 ebf2, EIN3ox, and ctr1 flowers from 7-week-old plants. (H) Phenotype of 7-week-old plants of the indicated genotypes. (I and J) Phenotype of 3-day-old etiolated seedlings grown on MS medium supplemented with 10 μM of ACC.

Example 6 ebf1 and ebf2 Mutants Confer Enhanced Ethylene Responses and Stabilization of EIN3 Protein To investigate the biological relevance of EBF 1 and EBF2 in EIN3 regulation, we isolated mutants that harbor T-DNA insertion mutations in the two F-box genes. Two homozygous ebf1 mutants (ebf1-1, ebf1-2) and one homozygous ebf2 mutant (ebf2-1) were obtained (see Example 9, below). Each of these mutants contained a T-DNA insertion located within the LRR-encoding region (FIG. 5A). Northern blot analysis showed that the ebf1 mutants contained reduced levels of truncated versions of EBF 1 mRNA while the ebf2 mutant contained no detectable EBF2 mRNA (FIG. 5B). We examined the dose response of these mutants when treated with different concentrations of ACC. Compared with wild type, both ebf1-1 and ebf1-2 mutant alleles were hypersensitive to ACC at all concentration conditions tested; although ebf1-2 was generally less severe than ebf1-1 (FIGS. 5C and 5D). ebf2-1 also displayed hypersensitivity to ACC treatment, and a severe EIN3ox-like phenotype at the higher concentrations of ACC (FIGS. 5C and 5D). Therefore, both ebf1 and ebf2 mutants were found to be hypersensitive to ethylene. We next examined whether ebf1 and ebf2 mutations affect EIN3 accumulation. As shown in FIG. 5E, the levels of EIN3 protein were higher in ebf1-1 than in wild type or ebf2-1 in the absence of ethylene. Upon ethylene treatment, the levels of EIN3 in either ebf1-1 or ebf2-1 were appreciably higher than those in wild type. These data indicate that defects in either EBF1 or EBF2 lead to increased EIN3 accumulation, and a correspondingly enhanced ethylene response.

To test the genetic interaction of ebf1 and ebf2 mutants, we generated ebf1 ebf2 double mutant plants. ebf1 ebf2 etiolated seedlings showed a pronounced triple response phenotypes in the absence of exogenous ethylene (FIG. 5D). Whereas ebf1 and ebf2 single mutant plants were normal except that ebf1 had modest dwarfism and reduced fertility (FIG. 5H), ebf1 ebf2 double mutants displayed phenotypes characteristic of ctr1 mutants or plants overexpressing EIN3 (FIGS. 5G and 5H). ebf1 ebf2 adult plants showed dwarfism, produced flowers with protruding gynoecium, and developed small size rosette leaves. Moreover, immunoblot analysis revealed that, in the absence of applied ethylene, the level of EIN3 protein was dramatically higher in ebf1 ebf1 plants than in wild-type plants and similar to the level found in ctr1 (FIG. 5F). Interestingly, ebf1 ebf2 plants also showed severely reduced fertility, a phenotype observed in EIN2-CENDox plants (Alonso et al., *Science* 284, 2148-2152, 1999). These results reveal that a synergistic interaction exists between ebf1 and ebf2 mutants, suggesting a functional redundancy between two EBF proteins and confirming a role for SCF function in the response to ethylene.

To test whether the ethylene hypersensitivity caused by ebf1 and ebf2 mutations is the consequence of enhanced EIN3 stability, we generated double mutants between ein3 and ebf1 or ebf2. As shown in FIG. 5I, ein3-1 suppressed the ethylene phenotypes of both ebf1-1 and ebf2-1 mutants, indicating that the ebf1 and ebf2 mutants result in enhanced ethylene responsiveness by stabilizing EIN3 protein. Genetic studies revealed that EIN2 is an upstream component activating EIN3 function (Stepanova and Ecker, *Curr Opin Plant Mal* 3, 353-360, 2000). To examine the positions of EBF1 and EBF2 relative to other ethylene signaling components, we generated double mutants between ein2 and ebf1 or ebf2. Phenotypic analysis revealed that ebf1-1 and ebf2-1 partially suppressed ein2-5 (FIG. 5J), suggesting that EBF1 and EBF2 might act downstream of EIN2, although we cannot exclude that these molecules could act in parallel pathways. Take together, we conclude that EBF1 and EBF2 function as negative regulators of the ethylene signaling pathway by destabilizing EIN3.

Example 7

Overexpression of EBF 1 or EBF2 Results in Reduced Sensitivity to Ethylene

Figure 6:
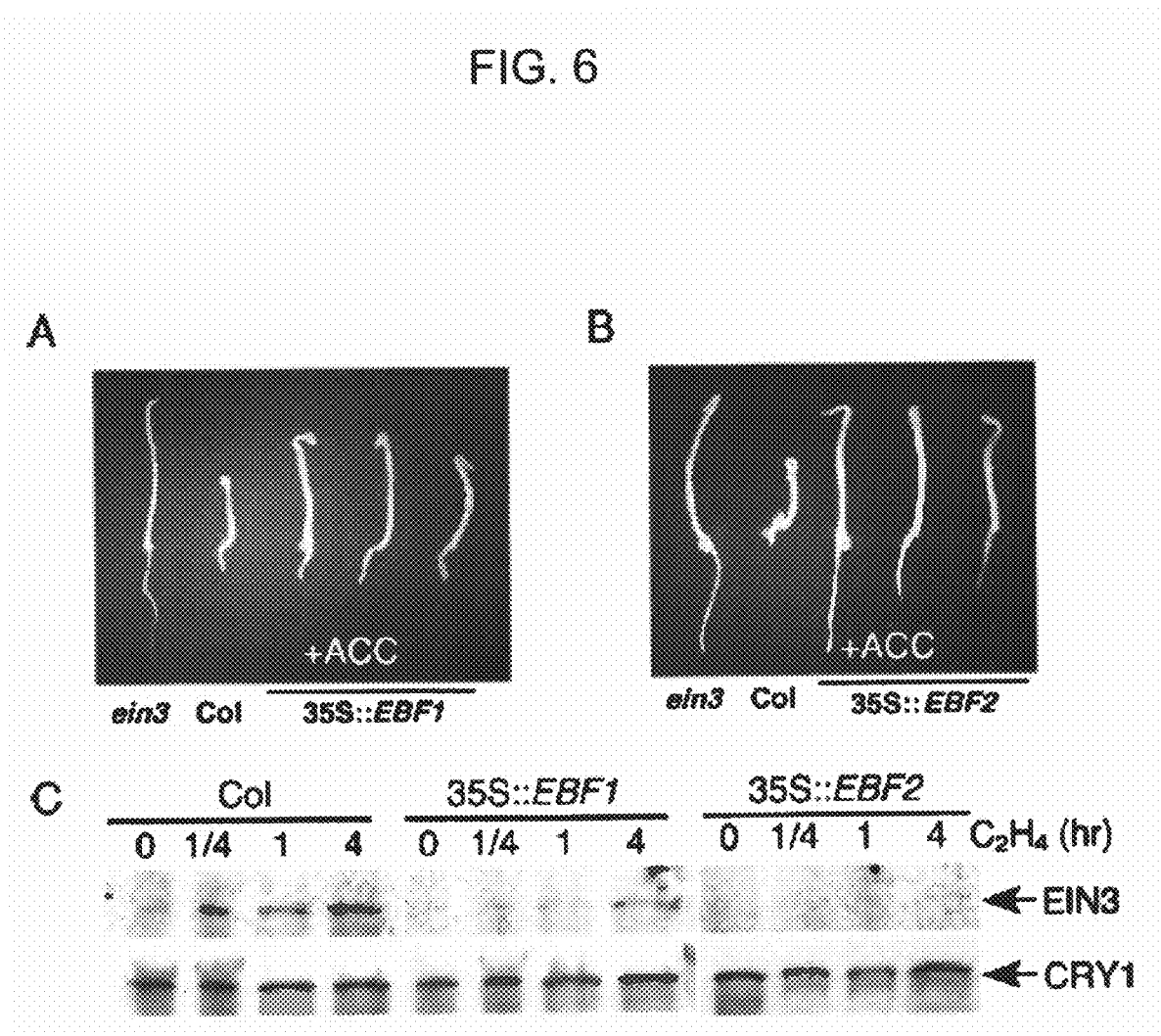
FIGS. 6A-6C show that overexpression of the F-box genes results in ethylene insensitivity and reduced accumulation of EIN3 protein. (A&B) Phenotype of 3-day-old etiolated seedlings grown on MS medium supplemented with 10 μM of ACC. Three independent transgenic lines that overexpress EBF1 (A) or EBF2 (B) in Col background were presented. (C) Immunoblot assays of EIN3 protein in overexpression transgenic lines.

To further define the function of EBF1 and EBF2 in the ethylene signaling pathway, we constructed transgenic plants containing either F-box gene under the control of the CaMV 35S promoter, allowing constitutive high-level (5- to 20-fold increase) expression of RNAs for each of these genes (data not shown). As exemplified by an elongated hypocotyl and opened hypocotyl hook, overexpression of EBF1 caused partial insensitivity to ethylene, especially in aerial tissues (FIG. 6A). Similarly, overexpression of EBF2 resulted in strong ethylene-insensitivity in both aerial and root tissues, comparable to the ein3 mutant (FIG. 6B). Furthermore, overexpression of EBF2 greatly suppressed the phenotype of the constitutive ethylene overproduction mutant eto2 (data not shown). To clarify whether the reduced ethylene-sensitivity caused by overexpression of EBF1 or EBF2 arose from a defect in EIN3 protein accumulation, we monitored the levels of EIN3 in the EBF1 and EBF2 overexpression plants. Ethylene-dependent accumulation of EIN3 protein was greatly impaired in transgenic plants overexpressing EBF1 or EBF2 compared with wild type (FIG. 6C). Taken together, these results reveal that EIN3-dependent ethylene responses are regulated by two previously uncharacterized F-box proteins, EBF1 and EBF2.

Example 8

Modulation of F-box proteins ERF1 and ERF2 Modulates the Ethylene Response through EIN3

EIN3 is a plant-specific DNA-binding protein that is both necessary and sufficient for the activation of all known ethylene responses. Here, we show that EIN3 accumulation is regulated by ethylene gas at the protein level, and identify two new genes (and their corresponding mutants) that function as negative regulators in the ethylene signaling pathway. Several lines of evidence indicate that the level of EIN3 protein directly reflects the strength of the ethylene signal, and regulation of EIN3 abundance is a rate-limiting step in the ethylene response pathway. First, the extent of ethylene response arising from different concentrations of ACC is positively correlated with the abundance of EIN3 protein. Second, the level of EIN3 protein is induced by ethylene, and the kinetics of EIN3 induction are comparable with those of the induction of ethylene-responsive genes (e.g. ERF1) (Solano et al., *Genes Dev* 12, 3703-3714, 1998). Third, elevated EIN3 levels in transgenic plants (EIN3ox) result in a constitutive triple response (Chao et al., Cell 89, 1133-1144, 1997). Moreover, the level of EIN3ox protein can be further escalated by ethylene treatment, which consequently leads to even greater ethylene response phenotypes. Fourth, all ethylene-insensitive mutants that we examined are impaired in the accumulation of EIN3 protein. Likewise, treatment with silver ion, a potent inhibitor of ethylene action, abolishes EIN3 accumulation. On the other hand, in the ctr1 and eto mutants, which display constitutive ethylene response (Guzman and Ecker, Plant Cell 2, 513-523, 1990; Kieber et al., Cell 72, 427-441, 1993), steady state EIN3 levels are greater than that of wild type in the absence of ethylene. Fifth, inhibition of EIN3 proteolysis by mutations in the EBF1/EBF2 genes increases EIN3 accumulation and consequently results in enhanced ethylene responses. Last, promotion of EIN3 degradation by overexpression of EBF1/EBF2 leads to reduced EIN3 abundance and thereby partial ethylene insensitivity.

Genetic and molecular studies have unraveled a linear ethylene signal transduction pathway, in which EIN3 acts downstream of the ETR/ERS receptors, CTR1 and EIN2. Consistent with this notion, our biochemical studies show that ETR1, EIN4, CTR1, and EIN2 are all required for the regulation of EIN3 accumulation. In addition, we show that EIN5 and EIN6, whose positions in the ethylene signaling pathway were previously obscure, are also required for EIN3 accumulation in response to ethylene. These results thus establish that both EIN5 and EIN6 act upstream of EIN3. With the notable exception of ein2 null mutants, EIN3 can accumulate to some extent after long exposure to ethylene in all other ethylene insensitive mutants examined (etr1, ein4, ein5, ein6), suggesting that the ethylene signaling is not completely blocked in these plants. Furthermore, the level of EIN3 remains weakly responsive to ethylene in ctr1-1 mutants, although an elevated basal level is observed in ctr1-1 in the absence of ethylene. As ctr1-1 was shown to be a null mutation (Huang et al., Plant J 33, 221-233, 2003), these results suggest the existence of a CTR1-independent response, which adds a new dimension to the linear ethylene pathway. This is consistent with the observation that ctr1 seedlings respond to ethylene treatment (Larsen and Chang, Plant Physiol 125, 1061-1073, 2001).

In the absence of ethylene, EIN3 is an unstable protein with a half-life shorter than 30 minutes. Several short-lived proteins are subject to proteasome-mediated protein degradation process in both animals and plants (Hellmann and Estelle, Science 297, 793-797, 2002; Hochstrasser, Annu Rev Genet. 30, 405-439, 1996). For instance, AUX/IAA proteins, a group of transcriptional repressors in auxin signaling, are degraded through an ubiquitin/proteasome pathway (Gray et al., Nature 414, 271-276, 2001). Similarly, RGA/GAI/SLN proteins, negative components of the GA signaling pathway, are destroyed by an ubiquitin/proteasome pathway (Sasaki et al., Science 299, 1896-1898, 2003; McGinnis et al., Plant Cell 15, 1120-1130, 2003). Here, we demonstrate that EIN3 transcription factor, a positive regulator in the ethylene signaling pathway, is targeted by the ubiquitin/proteasome pathway for degradation. Both endogenous and transgenically overexpressed EIN3 or an EIN3-GFP fusion protein can be stabilized by treatment with proteasome inhibitors (MG132 and MG115), as well as by ethylene treatment. In addition to increasing abundance, exposure to ethylene and MG132 treatment leads to nuclear localization of EIN3 protein. Thus, inhibition of proteasome function is reminiscent of the effects of exogenous ethylene treatment on EIN3 regulation, suggesting that ethylene induces EIN3 accumulation in the nucleus by interfering with the proteasome-mediated EIN3 degradation process. One possibility is that ethylene inhibits the function of proteolytic machinery that specifically targets EIN3 for destruction. Alternatively, ethylene might modulate EIN3 in a post-translational manner so that EIN3 becomes less accessible or more resistant to the degradation process. It is well known that ubiquitination of a target protein is often preceded by protein phosphorylation. As many ethylene signaling components are protein kinases (Gamble et al., Proc Natl Acad Sci 95, 7825-7829, 1998; Huang et al., Plant J 33, 221-233, 2003; Ouaked et al., Embo J 22, 1282-1288, 2003), it is conceivable that EIN3 may be phosphorylated, which could trigger EIN3 ubiquitination/degradation.

We have identified two F-box proteins (EBF1 and EBF2) that interact with EIN3, and demonstrated the involvement of these two proteins in EIN3 regulation as well as in the ethylene response pathway. Loss-of-function mutations in the two F-box genes (ebf1 and ebf2) resulted in increased EIN3 accumulation, and consequently, enhanced response to ethylene. ebf1 ebf2 double mutants showed a wide range of ctr1-like phenotypes including the constitutive triple response in etiolated seedlings, protruding gynoecium, small size rosette and dwarfism in adult plants. Genetic studies revealed that ein3 suppresses the monogenic ebf1 and ebf2 mutants (this study) as well as the ebf1 ebf2 double mutants (Potuschak et al., Cell, 115(6), 679-89, 2003), indicating that the function of these two F-box proteins is dependent upon the presence of EIN3. Moreover, transgenic overexpression of either F-box gene leads to reduced EIN3 abundance and a corresponding decrease in sensitivity to ethylene. While monogenic ebf1 and ebf2 mutants slightly suppress ein2 (this study), ebf1 ebf2 double mutant plants show strong suppression (or bypass) of ein2 (Potuschak et al., Cell, 115(6), 679-89, 2003), suggesting that EBF1/EBF2 acts downstream of or parallel with EIN2. Together, these results demonstrate that EBF1 and EBF2 play a negatively regulatory role in the ethylene signaling pathway by targeting EIN3 for degradation.

Figure 7:
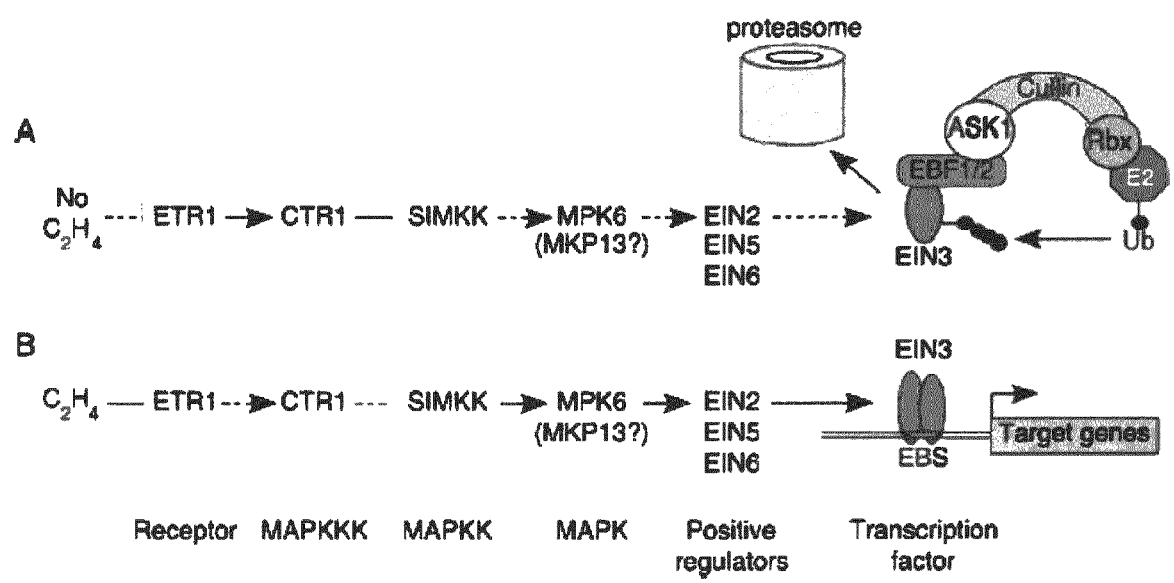
FIGS. 7A-7B show a model of how EIN3 may be regulated by ethylene. (A) In the absence of ethylene, the ETR/ERS receptors and CTR1 are active, thereby repress a MAPKK/MAPK cascade and inhibit the function of downstream components including EIN2, EIN5, and EIN6. As a result, EIN3 is targeted and ubiquitinated by a SCF complex containing one of the two F-box proteins, EBF1 and EBF2. The ubiquitinated form of EIN3 protein is thus recruited to the 26S proteasome for degradation. (B) In the presence of ethylene, the ETR/ERS receptors are bound with and inactivated by ethylene. CTR1 is inactive and the repression on the downstream pathway is released. Thus, the signal is transmitted through MAPKK/MAPK, EIN2, EIN5 and EIN6 to EIN3 transcription factor. As a result, EIN3 protein accumulates in the nucleus and binds to EIN3-binding site (EBS), which in turn activates gene expression. Arrows and bars represent positive and negative regulations, respectively. The solid and dotted lines indicate that the signal is on and off, respectively.

Based on these results, we propose a model for EIN3 regulation by ethylene (FIG. 7). In the absence of ethylene, the ER-associated ethylene receptors (e.g. ETR1) are active, and constitutively activate the Raf-like kinase CTR1. CTR1 then represses a MAPKK and MAPK cascade (Ouaked et al., Embo J 22, 1282-1288, 2003), and further inhibits the function of downstream components including EIN2, EIN5, and EIN6 (Wang et al., Plant Cell 14 Suppl, S131-151, 2002). As a result, EIN3 is targeted and ubiquitinated by the SCF complex containing one of the two F-box proteins, EBF1 and EBF2. The ubiquitinated form of EIN3 protein is thus recruited to the 26S proteasome for degradation (FIG. 7A). In the presence of ethylene, the ETR/ERS receptors are inactivated by ethylene binding. Without a positive regulatory signal from the receptors, CTR1 is inactive. Thus, the downstream positive regulators in the pathway are de-repressed, and the signal is transmitted through EIN2, EIN5 and EIN6 to EIN3 transcription factor. As a result, EIN3 protein becomes "resistant" to the SCF/proteasome-mediated proteolysis, accumulates in the nucleus, and binds to EIN3-binding site (EBS) and activates gene expression (FIG. 7B). Interestingly, the RNA levels of both EBF1 and EBF2 genes are induced by ethylene (FIG. 4E), suggesting that a negative feedback mechanism may exist to allow fine-tuning of EIN3 protein level.

This study reveals that the gaseous hormone ethylene exerts its effect on plant growth by controlling the abundance of EIN3 transcription factor. In addition, a link has been established between the ethylene signaling pathway and the ubiquitin/proteasome pathway, which has recently become the paradigm for plant hormone signaling. A ubiquitin/proteasome pathway has been demonstrated in auxin, GA, and JA signaling, and implicated in the ABA, SA, cytokinin, and brassinosteroid responses (reviewed by Frugis and Chua, *Trends Cell Biol* 12, 308-311, 2002; Vierstra, *Trends Plant Sci* 8, 135-142, 2003). It is worth noting that the ubiquitin/proteasome pathway positively regulates the auxin, GA, and JA signaling pathway by targeting negative regulators for degradation (Gray et al., *Genes Dev* 13, 1678-1691, 1999; Sasaki et al., *Science* 299, 1896-1898, 2003; Xie et al., 1998). The corresponding hormone acts to promote the repressors' degradation. In contrast, the ubiquitin/proteasome pathway mediated by EBF1/EBF2 negatively regulates the ethylene signaling pathway by targeting EIN3 transcription factor for degradation. Ethylene acts to stabilize EIN3 protein by preventing its degradation process. A similar regulatory mechanism might also occur in the ABA signaling pathway, mediated by the bZIP transcription factor ABI5 (Lopez-Molina et al., *Proc Natl Acad Sci* 98, 4782-4787, 2001), and in the brassinosteroid signaling pathway, mediated by two nuclear proteins BES1/BZR1 (He et al., *Proc Natl Acad Sci* 99, 10185-10190, 2002; Yin et al., *Cell* 109, 181-191, 2002). In both of these cases, the corresponding hormone has been shown to alter the stability of these positive regulators, although no F-box proteins or other SCF components have been identified that target these proteins for degradation. In this regard, ethylene is able to trigger an EIN3-mediated response rapidly by blocking protein turnover, rather than by initiating the more time-consuming route of de novo transcription/translation. This "jump-start" feature of the ethylene response pathway might be vital for the role of ethylene as an endogenous stress hormone, especially in the rapid response to wounding or various plant pathogens.

Example 9

Plant Growth Conditions, Drug Treatments and RNA Blot Analysis

With the exception of eto2 in Landsberg erecta (Ler) background, the ecotype Columbia (Col-0) was the parent strain for all mutant and transgenic lines described herein. *Arabidopsis* seeds were surface-sterilized and plated on the surface of MS medium (4.3 g MS salts, 10 g sucrose, pH 5.7, 8 g bactoagar per liter). After 3-4 days in the light at 4° C., the plates were wrapped in foil and kept in a 24° C. incubator before the phenotypes of seedlings were analyzed. For propagation, seedlings from plates were transferred to soil (Promix-HP) and grown to maturity at 22° C. under a 16 hr light/8 hr dark cycle.

Ethylene treatment of *Arabidopsis* seedlings grown on plates was performed in containers by flowing through hydrocarbon-free air supplemented with 10 ppm (parts per million) ethylene or were treated with hydrocarbon-free air alone (Kieber et al., *Cell* 72, 427-441, 1993). For drug treatments, *Arabidopsis* suspension cell cultures were treated with MG132 (50 µM), MG115 (50 µM), Pefabloc SC (100 µM) or DMSO (0.1%) for a time course study. Alternatively, etiolated seedlings were germinated for three days on a disc of Whatman paper resting on the surface of MS medium. MG132 (50 µM), MG115 (50 µM), Pefabloc SC (100 µM) or DMSO (0.1%) was added to the paper discs for 4 hr. Cycloheximide (100 µM) was added to the paper discs and ethylene or air was applied for different amounts of time.

Total RNA extractions and northern blot analysis were performed as described (Chao et al., *Cell* 89, 1133-1144, 1997).

Antibody Preparation and Immunoblot Assays

The coding region corresponding to residues 349 to 581 of EIN3 protein was PCR-amplified, expressed, purified from *E. coli*, and used to raise polyclonal antibodies in rabbits. Immunoblot assays were performed as described (Lin et al., *Proc Natl Acad Sci* 92, 8423-8427, 1995) with minor modifications. Protein samples were prepared by homogenizing the powdered tissues in 2×SDS-PAGE sample buffer and boiling the homogenate for 5 min. After centrifugation, the protein extracts were fractionated by 4-12% gradient Tris-Glycine Novex precast gels (Invitrogen), blotted onto a nitrocellulose filter. The blot was probed first with anti-EIN3 antibody, and was subsequently stripped with 0.2 N glycine (pH 2.5) for 3 times and re-probed with either anti-CRY1 antibody (Lin et al., *Proc Natl Acad Sci* 92, 8423-8427, 1995) or anti-SUB1 antibody (Guo et al., Science 291, 487-490, 2001)

Yeast Two-Hybrid Assays

The cDNA sequences of the EIN3, ASK1, F-box genes and their derivatives were cloned into pAS2 or pACT2 vector (Clontech). Yeast transformation, growth conditions, and filter-lift assays for β-galactosidase activity were performed according to the manufacturer's instructions (Clontech).

Isolation of T-DNA Insertion Lines and Genetic Analysis

To identify knockouts in the EBF1 and EBF2 genes, we first searched the database of Salk T-DNA collections (Alonso et al., *Science* 301, 653-657, 2003) and identified one mutant line, ebf1-1. We next screened a pooled genomic DNA collection containing approximately 80,000 T-DNA tagged lines by a PCR-based method (Alonso and Ecker, unpublished) and two additional mutants (ebf1-2 and ebf1-1) were identified. Plants homozygous for the insertions were identified by PCR-based genotyping. Co-segregation between phenotype of ebf1 or ebf1 mutant and the corresponding T-DNA insertion was established in the segregation population of backcross lines. Double mutants were constructed by genetic crosses and homozygous lines were identified by PCR-based genotyping.

Construction of Transgenic *Arabidopsis* Plants

EIN3 cDNA was cloned into the binary vector CHF3-GFP (Yin et al., *Cell* 109, 181-191, 2002). The resulting 35S::EIN3-GFP construct was introduced into *Agrobacterium* strain C58 and subsequently transformed into *Arabidopsis* wild-type (Col-0) and ein3-1 plants (Bechtold and Pelletier, Methods Mol. Biol. 82, 259-66, 1998). Kanamycin-resistant T1 plants were selected by plating seeds on MS medium supplemented with 1% sucrose and 50 µg/ml Kanamycin. The triple response phenotype was scored in T2 seedlings originated from individual Kanamycin-resistant T1 plants. Transgenic seedlings that expressed a functional EIN3-GFP fusion protein were mounted on glass slides using PBS as a mounting medium. All images were collected on a fluorescence microscope (Olympus BX60) and the color of the images was artificially added in Photoshop 5.0 (Adobe Systems). For the time course experiment, after the first cell image was taken, 50 µM of ACC or MG132 was applied to the slide and the same cell was followed for 4 hr.

The binary vector pKYLX7 was modified by inserting a loxP site in the MCS region (Li and Ecker, unpublished). The EBF1 and EBF2 full-length cDNA sequences were cloned into pUNI15 vector at Nde I/Bam HI site (a gift from Dr. Stephen Elledge). An in vitro plasmid fusion reaction, catalyzed by Cre recombinase, was carried out between pUNI15 (containing F-box cDNA sequence) and the modified pKYLX7. The resulting constructs that harbor the F-box coding regions driven by CaMV 35S promoter were introduced into *Agrobacterium* strain C58 and subsequently transformed into *Arabidopsis* plants. Transgenic T1 plants were identified by Kanamycin selection. The triple response phenotype was scored in T2 seedlings originated from individual transgenic T1 plants. Homozygous T3 seedlings were subjected to ethylene treatment and immunoblot assays.

REFERENCES

The following references are hereby incorporated by reference in their entirety.

Abeles, F. B., Morgan, P. W., and Saltveit, M. E. Jr. (1992). Ethylene in Plant Biology, Second Edition. (New York: Academic Press, Inc)

Alonso, J. M., Hirayama, T., Roman, G., Nourizadeh, S., and Ecker, J. R. (1999). EIN2, a bifunctional transducer of ethylene and stress responses in *Arabidopsis*. Science 284, 2148-2152.

Alonso, J. M., Stepanova, A. N., Leisse, T. J., Kim, C. J., Chen, H., Shinn, P., Stevenson, D. K., Zimmerman, J., Barajas, P., Cheuk, R., et al. (2003). Genome-wide insertional mutagenesis of *Arabidopsis thaliana*. Science 301, 653-657.

Bleecker, A. B., Estelle, M. A., Somerville, C., and Kende, H. (1988). Insensitivity to ethylene conferred by a dominant mutation in *Arabidopsis thaliana*. Science 241, 1086-1089.

Bleecker, A. B., and Kende, H. (2000). Ethylene: a gaseous signal molecule in plants. Annu Rev Cell Dev Biol 16, 1-18.

Chang, C., Kwok, S. F., Bleecker, A. B., and Meyerowitz, E. M. (1993). *Arabidopsis* ethylene-response gene ETR1: similarity of product to two-component regulators. Science 262, 539-544.

Chao, Q., Rothenberg, M., Solano, R., Roman, G., Terzaghi, W., and Ecker, J. R. (1997). Activation of the ethylene gas response pathway in *Arabidopsis* by the nuclear protein ETHYLENE-INSENSITIVE3 and related proteins. Cell 89, 1133-1144.

Chen, Y. F., Randlett, M. D., Findell, J. L., and Schaller, G. E. (2002). Localization of the ethylene receptor ETR1 to the endoplasmic reticulum of *Arabidopsis*. J Biol Chem 277, 19861-19866.

Deshaies, R. J. (1999). SCF and Cullin/Ring H2-based ubiquitin ligases. Annu Rev Cell Dev Biol 15, 435-467.

Ecker, J. R. (1995). The ethylene signal transduction pathway in plants. Science 268, 667-675.

Frugis, G., and Chua, N. H. (2002). Ubiquitin-mediated proteolysis in plant hormone signal transduction. Trends Cell Biol 12, 308-311.

Gagne, J. M., Downes, B. P., Shiu, S. H., Durski, A. M., and Vierstra, R. D. (2002). The F-box subunit of the SCF E3 complex is encoded by a diverse superfamily of genes in *Arabidopsis*. Proc Natl Acad Sci USA 99, 11519-11524.

Gamble, R. L., Coonfield, M. L., and Schaller, G. E. (1998). Histidine kinase activity of the ETR1 ethylene receptor from *Arabidopsis*. Proc Natl Acad Sci USA 95, 7825-7829.

Gray, W. M., del Pozo, J. C., Walker, L., Hobbie, L., Risseeuw, E., Banks, T., Crosby, W. L., Yang, M., Ma, H., and Estelle, M. (1999). Identification of an SCF ubiquitin-ligase complex required for auxin response in *Arabidopsis thaliana*. Genes Dev 13, 1678-1691.

Gray, W. M., Kepinski, S., Rouse, D., Leyser, O., and Estelle, M. (2001). Auxin regulates SCF(TIR1)-dependent degradation of AUX/IAA proteins. Nature 414, 271-276.

Guo, H., Mockler, T., Duong, H., and Lin, C. (2001). SUB 1, an *Arabidopsis* Ca2+-binding protein involved in cryptochrome and phytochrome coaction. Science 291, 487-490.

Guzman, P., and Ecker, J. R. (1990). Exploiting the triple response of *Arabidopsis* to identify ethylene-related mutants. Plant Cell 2, 513-523.

He, J. X., Gendron, J. M., Yang, Y., Li, J., and Wang, Z. Y. (2002). The GSK3-like kinase BIN2 phosphorylates and destabilizes BZR1, a positive regulator of the brassinosteroid signaling pathway in *Arabidopsis*. Proc Natl Acad Sci USA 99, 10185-10190.

Hellmann, H., and Estelle, M. (2002). Plant development: regulation by protein degradation. Science 297, 793-797.

Hochstrasser, M. (1996). Ubiquitin-dependent protein degradation. Annu Rev Genet. 30, 405-439.

Hua, J., and Meyerowitz, E. M. (1998). Ethylene responses are negatively regulated by a receptor gene family in *Arabidopsis thaliana*. Cell 94, 261-271.

Hua, J., Sakai, H., Nourizadeh, S., Chen, Q. G., Bleecker, A. B., Ecker, J. R., and Meyerowitz, E. M. (1998). EIN4 and ERS2 are members of the putative ethylene receptor gene family in *Arabidopsis*. Plant Cell 10, 1321-1332.

Huang, Y., Li, H., Hutchison, C. E., Laskey, J., and Kieber, J. J. (2003). Biochemical and functional analysis of CTR1, a protein kinase that negatively regulates ethylene signaling in *Arabidopsis*. Plant J 33, 221-233.

Kieber, J. J., Rothenberg, M., Roman, G., Feldmann, K. A., and Ecker, J. R. (1993). CTR1, a negative regulator of the ethylene response pathway in *Arabidopsis*, encodes a member of the raf family of protein kinases. Cell 72, 427-441.

Larsen, P. B., and Chang, C. (2001). The *Arabidopsis* eer1 Mutant Has Enhanced Ethylene Responses in the Hypocotyl and Stem. Plant Physiol 125, 1061-1073.

Lee, D. H., and Goldberg, A. L. (1998). Proteasome inhibitors: valuable new tools for cell biologists. Trends Cell Biol 8, 397-403.

Lin, C., Ahmad, M., Gordon, D., and Cashmore, A. R. (1995). Expression of an *Arabidopsis* cryptochrome gene in transgenic tobacco results in hypersensitivity to blue, UV-A, and green light. Proc Natl Acad Sci USA 92, 8423-8427.

Lopez-Molina, L., Mongrand, S., and Chua, N. H. (2001). A postgermination developmental arrest checkpoint is mediated by abscisic acid and requires the ABI5 transcription factor in *Arabidopsis*. Proc Natl Acad Sci USA 98, 4782-4787.

McGinnis, K. M., Thomas, S. G., Soule, J. D., Strader, L. C., Zale, J. M., Sun, T. P., and Steber, C. M. (2003). The *Arabidopsis* SLEEPY1 gene encodes a putative F-box subunit of an SCF E3 ubiquitin ligase. Plant Cell 15, 1120-1130.

Ouaked, F., Rozhon, W., Lecourieux, D., and Hirt, H. (2003). A MAPK pathway mediates ethylene signaling in plants. Embo J 22, 1282-1288.

Roman, G., Lubarsky, B., Kieber, J. J., Rothenberg, M., and Ecker, J. R. (1995). Genetic analysis of ethylene signal transduction in *Arabidopsis thaliana*: five novel mutant loci integrated into a stress response pathway. Genetics 139, 1393-1409.

Sakai, H., Hua, J., Chen, Q. G., Chang, C., Medrano, L. J., Bleecker, A. B., and Meyerowitz, E. M. (1998). ETR2 is an ETR1-like gene involved in ethylene signaling in *Arabidopsis*. Proc Natl Acad Sci USA 95, 5812-5817.

Sasaki, A., Itoh, H., Gomi, K., Ueguchi-Tanaka, M., Ishiyama, K., Kobayashi, M., Jeong, D. H., An, G., Kitano, H., Ashikari, M., and Matsuoka, M. (2003). Accumulation of phosphorylated repressor for gibberellin signaling in an F-box mutant. Science 299, 1896-1898.

Solano, R., Stepanova, A., Chao, Q., and Ecker, J. R. (1998). Nuclear events in ethylene signaling: a transcriptional cascade mediated by ETHYLENE-INSENSITIVE3 and ETHYLENE-RESPONSE-FACTOR1. Genes Dev 12, 3703-3714.

Stepanova, A. N., and Ecker, J. R. (2000). Ethylene signaling: from mutants to molecules. Curr Opin Plant Biol 3, 353-360.

Vierstra, R. D. (2003). The ubiquitin/26S proteasome pathway, the complex last chapter in the life of many plant proteins. Trends Plant Sci 8, 135-142.

Wang, K. L., Li, H., and Ecker, J. R. (2002). Ethylene biosynthesis and signaling networks. Plant Cell 14 Suppl, S131-151.

Xiao, W., and Jong, J. (2000). F-box proteins in *Arabidopsis*. Trends Plant Sci 5, 454-457.

Xie, D. X., Feys, B. F., James, S., Nieto-Rostro, M., and Turner, J. G. (1998). COI1: an *Arabidopsis* gene required for jasmonate-regulated defense and fertility. Science 280, 1091-1094.

Yin, Y., Wang, Z. Y., Mora-Garcia, S., Li, J., Yoshida, S., Asami, T., and Chory, J. (2002). BES1 accumulates in the nucleus in response to brassinosteroids to regulate gene expression and promote stem elongation. Cell 109, 181-191.

SEQUENCES

```
SEQ ID NO: 1 EBF1 Polynucleotide Sequence
AY 91333
1918 bp
mRNA
linear
PLN 18-SEP-2 2
DEFINITION  Arabidopsis thaliana unknown protein At2g2549 )
mRNA, complete cds
ACCESSION   AY 91333
VERSION     AY 91333 1 GI: 2 259112
KEYWORDS    FLI CDNA
SOURCE      Arabidopsis thaliana thale cress)
gene = "At2g2549 "
ORIGIN
    1 atgtctcaga tctttagttt tgccggtgaa aatgattttt accgtcgtgg cgcaatatac
   61 ccaaacccaa aggatgctag tcttttgtta tcgcttggta gtttcgctga tgtttatttc
  121 cctccaagca agagatcacg tgttgttgca cctacgatct tcagtgcttt cgagaaaaag
  181 ccagtttcca ttgatgtgct accagatgag tgtcttttg agatcttag gcgtttgtct
  241 ggaccacaag agaggagtgc ttgcgctttt gtctccaaac agtggcttac gcttgtaagt
  301 agcatccgtc aaaaggagat tgatgttcct tccaagataa ctgaagatgg tgatgattgt
  361 gaagggtgtt tgtctaggag cttagatggg aagaaggcaa cagatgttag attggcagca
  421 attgctgttg gaactgctgg tcgtggggga cttggaaaat tgtcgattcg aggtagcaac
  481 tctgctaaag tttcagatct tggtcttcgg tctattggtc gtagctgccc ttctctcggg
  541 tctctttcac tgtggaacgt ttctaccatt actgacaatg gactttgga gattgctgag
  601 ggttgtgctc aacttgagaa gcttgagctg aaccgctgct ctacaatcac tgacaagggt
  661 ttggtagcta ttgctaagag ctgccccaac ttgactgagc tgacattgga ggcttgttca
  721 agaattggag atgagggttt gctagccatt gcaagatcct gctccaagct gaagtcagtc
  781 tcgatcaaga actgtcctct tgtcagggat caaggaatcg cctctctact gtctaacacc
  841 acctgttcct tggcaaaact taagcttcag atgctgaatg tcactgatgt gtctcttgct
  901 gttgtgggtc attacggctt gtcgatcact gatcttgtgc tcgctggatt atcacacgtg
  961 agcgagaagg gattctgggt catgggaaat ggtgtcgggc tgcaaaaatt aaactctctg
 1021 accatcacag cctgccaagg agtgactgac atggggcttg aatctgttgg aaagggctgc
 1081 ccgaacatga aaaaggcgat catcagtaaa tccccttgt tatctgacaa cgggttggtc
 1141 tcttttgcaa aagcttcttt atcacttgag agtcttcagc ttgaagaatg ccacagggtt
 1201 acccaatttg ggttttttgg ttcccttttg aactgtgtg aaaagttgaa ggctttctct
 1261 ctggtgaact gtttgagtat tagagatctc accacaggat tgcctgcttc atctcattgc
 1321 agcgctctgc gctctttgtc tattcgtaac tgccctggct ttggtgatgc aaatcttgca
 1381 gccatcggga agttgtgccc tcagctcgag gatattgatc tgtgtgggct caagggata
 1441 acagagtctg gtttcctaca tctgattcag agctctcttg tgaagatcaa cttcagtggt
 1501 tgttccaatt tgactgatag agtgatctct gccatcactg ctcgtaacgg gtggactctt
 1561 gaagtcttaa acatcgatgg atgttccaat atcactgacg ccagcctggt ctccattgca
 1621 gcaaactgcc agattctcag tgatttggat atttcgaaat gcgcaatctc agattcaggg
 1681 attcaagcat tggcctcctc tgataagctc aaactgcaga tcctatcagt tgcaggttgc
 1741 tctatggtta cagacaagag cttgccagcc atcgtcgggt tgggttccac tctattggga
 1801 ttaaacctcc aacagtgtcg atccatttcc aattccactg tcgacttctt agtcgagcgt
 1861 ctttacaaat gtgacatcct ctcctgatca acaattccac tgtcgacctc tccactta SEQ ID NO: 2 EBF1 Protein Sequence
AY 91333
1918 bp
Translated mRNA
linear
PLN 18-SEP-2 2
DEFINITION  Arabidopsis thaliana unknown protein At2g2549 )
mRNA, complete
                     cds
ACCESSION   AY 91333
VERSION     AY 91333 1 GI: 2 259112
KEYWORDS    FLI CDNA
SOURCE      Arabidopsis thaliana thale cress)
MSQIFSFAGENDFYRRGAIYPNPKDASLLLSLGSFADVYFPPSKRSRVVAPTIFSAFEKKPVSIDVLPDE
CLFEIFRRLSGPQERSACAFVSKQWLTLVSSIRQKEIDVPSKITEDGDDCEGCLSRSLDGKKATDVRLAA
```

-continued

SEQUENCES

IAVGTAGRGGLGKLSIRGSNSAKVSDLGLRSIGRSCPSLGSLSLWNVSTITDNGLLEIAEGCAQLEKLEL
NRCSTITDKGLVAIAKSCPNLTELTLEACSRIGDEGLLAIARSCSKLKSVSIKNCPLVRDQGIASLLSNT
TCSLAKLKLQMLNVTDVSLAVVGHYGLSITDLVLAGLSHVSEKGFWVMGNGVGLQKLNSLTITACQGVTD
MGLESVGKGCPNMKKAIISKSPLLSDNGLVSFAKASLSLESLQLEECHRVTQFGFFGSLLNCGEKLKAFS
LVNCLSIRDLTTGLPASSHCSALRSLSIRNCPGFGDANLAAIGKLCPQLEDIDLCGLKGITESGFLHLIQ
SSLVKINFSGCSNLTDRVISAITARNGWTLEVLNIDGCSNITDASLVSIAANCQILSDLDISKCAISDSG
IQALASSDKLKLQILSVAGCSMVTDKSLPAIVGLGSTLLGLNLQQCRSISNSTVDFLVERLYKCDILS

SEQ ID NO: 3 EBF2 Polynucleotide Sequence
AY485830.
24 bp
mRNA
linear
PLN 3 -DEC-2 3
DEFINITION  *Arabidopsis thaliana* EIN3-binding F-box protein 2 EBF2)
            mRNA,
complete cds
ACCESSION   AY48583
VERSION     AY48583 1 GI: 387 5 8
KEYWORDS
SOURCE      *Arabidopsis thaliana* thale cress)
Protein degradation"
product = "EIN3-binding F-box protein 2"
protein id = "AAR27 72 1"
db xref = "GI: 387 5 81"
ORIGIN
    1 tcttcgatct cttcaaatct tcgtctttct tcttcaaatc ttcttcgaat tatgtctgga
   61 atcttcagat ttagtggtga tgaagattgt ttacttgggg gatcgatgta tctatcacca
  121 gggagctgtc ccggtgtata ttacccagcg cgtaagaggt tacgtgttgc tgcgacgtcg
  181 ttttacagcg gttttgagga gaagcaaact tcaatcgatg tattgcctga agagtgttta
  241 tttgagattc taagacgttt accttctgga caagagagga gtgcttgcgc ttgtgtttcc
  301 aagcattggc ttaatctttt gagtagtatc agtaggagtg aagtgaatga gtcatcagtt
  361 caagatgtgg aggagggtga agggtttttg tctaggagtt tggaggggaa gaaggcgacg
  421 gatttgaggt tggcggcgat tgcggttggg acgtcgagtc gtggtgggtt ggggaagctt
  481 cagattcgtg ggagtgggtt tgagagtaag gtgactgatg ttggtcttgg tgctgttgct
  541 catggttgtc catctcttag gattgtttct ttatgaaact tgcctgctgt tagtgatttg
  601 ggtttgtctg agatcgcacg gtcatgcccg atgattgaaa aacttgacct ttcacggtgt
  661 cctggaataa ctgacagtgg attggttgct attgctgaga actgtgtgaa tctgagtgat
  721 ctgacgattg attcttgctc tggtgttggg aatgagggtt taagggctat tgcaagacgt
  781 tgtgtcaatc tgagatctat ctctatcagg agctgcccac gtattggtga tcaaggtgtt
  841 gccttcctct tggctcaagc tggttcttac ttgacgaaag tgaaactcca gatgctgaac
  901 gtatctggtt tgtctcttgc tgttattggt cactacggag cagctgttac tgatcttgtg
  961 cttcatggac ttcaaggtgt gaatgagaaa ggcttctggg ttatgggaaa tgcaaagggg
 1021 ttgaagaaac tgaagtccct ctcagtaatg tcgtgcagag gtatgaccga tgttgggctc
 1081 gaagctgttg gaaatggttg ccctgatctg aagcatgtct ctctgaacaa atgcttgctt
 1141 gtttctggta aaggacttgt cgctttggcc aaatctgcat tgtcacttga agtttgaaa
 1201 cttgaagaat gccacaggat caaccagttt ggtcttatgg gttttctcat gaactgtggc
 1261 tcaaagttga aagctttctc tttggcaaac tgtctgagca tcagtgactt caactcagaa
 1321 tcctctctgc catcacccag ttgcagctct ttacgttctc tgtcaatccg atgctgccct
 1381 gggtttgggg atgcaagtct cgctttcttg gaaagttct gtcatcagct tcaggatgtt
 1441 gaactctgtg gactaaacgg agtgacagat gcaggtgtgc gcgagttgct acagagcaac
 1501 aatgttggtc tagtgaaggt gaacctgagc gaatgtatca atgtttcaga caacacagtc
 1561 tctgcaattt ctgttttgcca cggacgcaca ttggagtctc ttaaccttga cggctgcaag
 1621 aacatcacaa acgcaagcct tgtcgcagta gccaagaact gctactcagt caatgacctt
 1681 gacatctcaa atactttggt ctcagatcac ggaatcaagg ccttggcatc ttctcctaac
 1741 catctgaatc ttcaggttct ttccattggc ggctgctcct caattacaga caaaagcaag
 1801 gcatgcatac aaaaactcgg ccgcacgctt ttgggattaa acatccaacg ttgtggcaga
 1861 atcagcagca gcactgtgga tactcttctc gaaaatctat ggaggtgcga tatactctac
 1921 taaattccca cttttctac aaaaccttag tatcatcatc atcagtccaa gtcttttcc
 1981 taggttttgg tcgctaaaac ccatagattc cacctagaac ttagtttctt tctcaggaca
 2041 ctgcagttgt tttttaaaat ttttggcagg ttccttctaa acaaaggagc ctgtttctac
 2101 aactgttagt gttttgtga agcctgtcac tgagttctgg taatctagtt tagggtttag
 2162 tcttgaccgt cttttggag ttgttgtctc tctatgttca gtaaagttct tgtagaagtc
 2221 atttgttctt tggtttaggt tcgtgatagt gccttttatc ttcttccact gtagagcttt
 2281 tggcaatggc ggtgtaactt cttaatccgc cattacaact cttcggagtt gttttttgt
 2341 gtgttatgta tctgccaaaa gctctgtttt ttcccacttt tttgtttaag gcactatctt SEQ ID NO: 4 EBF2 Protein Sequence
AY485830.
24 bp
Translated mRNA
linear
PLN 3 -DEC-2 3
DEFINITION  *Arabidopsis thaliana* EIN3-binding F-box protein 2 EBF2)
            mRNA,
complete cds
ACCESSION   AY48583
VERSION     AY48583 1 GI: 387 5 8

SEQUENCES

```
KEYWORDS
SOURCE      Arabidopsis thaliana thale cress)
Protein degradation"
product = "EIN3-binding F-box protein 2"
protein id = "AAR27 72 1"
db xref = "GI: 387 5 81"
MSGIFRFSGDEDCLLGGSMYLSPGSCPGVYYPARKRLRVAATSFYSGFEEKQTSIDVLP
EECLFEILRRLPSGQERSACACVSKHWLNLLSSISRSEVNESSVQDVEEGEGFLSRSLE
GKKATDLRLAAIAVGTSSRGGLGKLQIRGSGFESKVTDVGLGAVAHGCPSLRIVSLWNL
PAVSDLGLSEIARSCPMIEKLDLSRCPGITDSGLVAIAENCVNLSDLTIDSCSGVGNEG
LRAIARRCVNLRSISIRSCPRIGDQGVAFLLAQAGSYLTKVKLQMLNVSGLSLAVIGHY
GAAVTDLVLHGLQGVNEKGFWVMGNAKGLKKLKSLSVMSCRGMTDVGLEAVGNGCPDLK
HVSLNKCLLVSGKGLVALAKSALSLESLKLEECHRINQFGLMGFLMNCGSKLKAFSLAN
CLGISDFNSESSLPSPSCSSLRSLSIRCCPGFGDASLAFLGKFCHQLQDVELCGLNGVT
DAGVRELLQSNNVGLVKVNLSECINVSDNTVSAISVCHGRTLESLNLDGCKNITNASLV
AVAKNCYSVNDLDISNTLVSDHGIKALASSPNHLNLQVLSIGGCSSITDKSKACIQKLG
RTLLGLNIQRCGRISSSTVDTLLENLWRCDILY SEQ ID NO: 5 EIN3 Polynucleotide Sequence
LOCUS       NM 112968
2413 bp
mRNA
linear
PLN 19-FEB-2 4
DEFINITION  Arabidopsis thaliana ethylene-insensitive 3 EIN3) At3g2
            77 ) mRNA, complete cds
ACCESSION   NM 112968
VERSION     NM 112968 3 GI: 3 685926
SOURCE      Arabidopsis thaliana thale cress)
ORIGIN
     1 acagagagac tccacaaaga aacgcaaata aacaaaagtc gctttctagc cacgtgatct
    61 ttcgtcgact tttcttcttc ttcttcttct tcctcttcct catctcgtat ctctaacttt
   121 tgtcgaagtt ctttttgatga aactagggt tattatcttc tccttctttt tcccatcacc
   181 atagaaaagg cagagacctt tttcttcatc atttttattc tccttcttct tctgctgttc
   241 atttctccag gttacaatga tgtttaatga gatgggaatg tgtggaaaca tggatttctt
   301 ctcttctgga tcacttggtg aagttgattt ctgtcctgtt ccacaagctg agcctgattc
   361 cattgttgaa gatgactata ctgatgatga gattgatgtt gatgaattgg agaggaggat
   421 gtggagagac aaaatgcggc ttaaacgtct caaggagcag gataagggta aagaaggtgt
   481 tgatgctgct aaacagaggc agtctcaaga gcaagctagg aggaagaaaa tgtctagagc
   541 tcaagatggg atcttgaagt atatgttgaa gatgatggaa gtttgtaaag ctcaaggctt
   601 tgtttatggg attattccgg agaatggaaa gcctgtgact ggtgcttctg ataatttaag
   661 ggagtggtgg aaagataagg ttaggtttga tcgtaatggt cctgcggcta ttaccaagta
   721 tcaagcggag aataatatcc cggggattca tgaaggtaat aacccgattg gaccgactcc
   781 tcataccttg caagagcttc aagacacgac tcttggatcg ttttgtctg cgttgatgca
   841 acactgtgat cctcctcaga gacgttttcc tttggagaaa ggagttcctc ctccgtggtg
   901 gcctaatggg aaagaggatt ggtggcctca acttggtttg cctaaagatc aaggtcctgc
   961 accttacaag aagcctcatg atttgaagaa ggcgtgaaa gtcggcgttt tgactgcggt
  1021 tatcaagcat atgtttcctg atattgctaa gatccgtaag ctcgtgaggc actctaaatg
  1081 tttgcaggat aagatgactg ctaaagagag tgctacctgg cttgctatta ttaaccaaga
  1141 agagtccttg gctagagagc tttatcccga gtcatgtcca cctctttctc tgtctggtgg
  1201 aagttgctcg cttctgatga atgattgcag tcaatacgat gttgaaggtt cgagaaggga
  1261 gtctcactat gaagtggaag agctcaagcc agaaaaagtt atgaattctt caaactttgg
  1321 gatggttgct aaaatgcatg acttcctgt caaagaagaa gtcccagcag gaaactcgga
  1381 attcatgaga aagagaaagc caaacagaga tctgaacact attatggaca gaaccgtttt
  1441 cacctgcgag aatcttgggt gtgcgcacag cgaaatcagc cggggatttc tggataggaa
  1501 ttcgagagac aaccatcaac tggcatgtcc acatcgagac agtcgcttac cgtatggagc
  1561 agcaccatcc aggtttcatg tcaatgaagt taagcctgta gttggatttc ctcagccaag
  1621 gccagtgaac tcagtagccc aaccaattga cttaacgggt atagttcctg aagatggaca
  1681 gaagatgatc tcagagctca tgtccatgta cgacagaaat gtccagagca accaaacctc
  1741 tatggtcatg gaaaatcaaa gcgtgtcact gcttcaaccc acagtccata accatcaaga
  1801 acatctccag ttcccaggaa acatggtgga aggaagtttc tttgaagact tgaacatccc
  1861 aaacagagca aacaacaaca acagcagcaa caatcaaacg ttttttcaag ggaacaacaa
  1921 caacaacaat gtgtttaagt tcgacactgc agatcacaac aactttgaag ctgcacataa
  1981 caacaacaat aacagtagcg gcaacaggtt ccagcttgtg tttgattcca caccgttcga
  2041 catggcgtca ttcgattaca gagatgatat gtcgatgcca ggagtagtag gaacgatgga
  2101 tggaatgcag cagaagcagc aagatgtatc catatggttc taaagtcttg gtagtagatt
  2161 tcatcttctc ttattttat ctttgtgtt cttacattca ctcaaccatg taatattttt
  2221 tcctgggtct ctctgtctct atcgcttgtt atgatgtgtc tgtaagagtc tctaaaaact
  2281 ctctgttact gtgtgtcttt gtctcggctt ggtgaatctc tctgtcatca tcagcttta
  2341 gttacacacc cgacttgggg atgaacgaac actaaatgta agttttcata atataaatat
  2401 atttgcaagc tct SEQ ID NO: 6 EIN3 Protein Sequence
LOCUS       NM 112968
2413 bp
translated mRNA
linear
PLN 19-FEB-2 4
```

-continued

SEQUENCES

DEFINITION  *Arabidopsis thaliana* ethylene-insensitive 3 EIN3) At3g2
77 ) mRNA, complete cds
ACCESSION   NM_112968
VERSION     NM_112968 3 GI: 3 685926
SOURCE      *Arabidopsis thaliana* thale cress)
MMFNEMGMCGNMDFFSSGSLGEVDFCPVPQAEPDSIVEDDYTDDEIDVDELERRMWRDK
MRLKRLKEQDKGKEGVDAAKQRQSQEQARRKKMSRAQDGILKYMLKMMEVCKAQGFVYG
IIPENGKPVTGASDNLREWWKDKVRFDRNGPAAITKYQAENNIPGIHEGNNPIGPTPHT
LQELQDTTLGSLLSALMQHCDPPQRRFPLEKGVPPPWWPNGKEDWWPQLGLPKDQGPAP
YKKPHDLKKAWKVGVLTAVIKHMFPDIAKIRKLVRQSKCLQDKMTAKESATWLAIINQE
ESLARELYPESCPPLSLSGGSCSLLMNDCSQYDVEGFEKESHYEVEELKPEKVMNSSNF
GMVAKMHDFPVKEEVPAGNSEFMRKRKPNRDLNTIMDRTVFTCENLGCAHSEISRGFLD
RNSRDNHQLACPHRDSRLPYGAAPSRFHVNEVKPVVGFPQPRPVNSVAQPIDLTGIVPE
DGQKMISELMSMYDRNVQSNQTSMVMENQSVSLLQPTVHNHQEHLQFPGNMVEGSFFED
LNIPNRANNNSSNNQTFFQGNNNNNNVFKFDTADHNNFEAAHNNNNNSSGNRFQLVFD
STPFDMASFDYRDDMSMPGVVGTMDGMQQKQQDVSIWF

What is claimed is:

1. A transgenic plant comprising a recombinant nucleic acid sequence that alters expression of an F-box gene, wherein the F-box gene encodes a protein comprising at least 90% sequence identity to the amino acid sequence shown in SEQ ID NO: 4 and that interacts with a EIN3, wherein EIN3 is involved in an ethylene response of the plant, wherein the recombinant nucleic acid sequence is operably linked to a promoter, and wherein said plant has altered sensitivity to ethylene.

2. The transgenic plant of claim 1, wherein said recombinant nucleic acid sequence increases the expression of the F-box gene reducing the plant's sensitivity to ethylene.

3. The transgenic plant of claim 1, wherein said protein comprises an F-box protein comprising at least 95% sequence identity to the amino acid sequence shown in SEQ ID NO: 4.

4. The transgenic plant of claim 1, wherein said protein comprises an F-box domain shown in SEQ ID NO: 7.

5. The transgenic plant of claim 1, wherein said recombinant nucleic acid sequence encodes the F-box protein expressed by said F-box gene.

6. The transgenic plant of claim 1, wherein said F-box gene comprises a polynucleotide sequence comprising at least 90% sequence identity to the nucleic acid sequence shown in SEQ ID NO: 3.

7. The transgenic plant of claim 1, wherein the EIN3 has at least 90% identity to the amino acid sequence shown in SEQ ID NO: 6.

8. The transgenic plant of claim 1, wherein the plant is selected from the group consisting of: rice, maize, wheat, barley, sorghum, millet, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussels sprouts, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, cranberries, grapefruit, lemons, limes, nectarines, oranges, peaches, pears, tangelos, tangerines, lily, carnation, chrysanthemum, petunia, rose, geranium, violet, gladioli, orchid, lilac, crabapple, sweetgum, maple, poinsettia, locust, ash, linden tree and *Arabidopsis thaliana*.

9. A method of regulating at least one aspect of ethylene response of a plant comprising modulating F-box protein activity or expression, wherein the F-box protein comprises at least 90% sequence identity to the amino acid sequence shown in SEQ ID NO: 4 and interacts with an EIN3 protein.

10. The method of claim 9, wherein expression of the F-box protein is increased, thereby reducing the plant's sensitivity to ethylene.

11. The method of claim 9, wherein the F-box protein comprises at least 95% sequence identity to the amino acid sequence shown in SEQ ID NO: 4.

12. The method of claim 9, wherein the F-box protein comprises and F-box domain shown in SEQ ID NO: 7.

13. The method of claim 9, wherein said F-box protein is encoded by a polynucleotide sequence comprising at least 90% sequence identity to the nucleic acid sequence shown in SEQ ID NO: 3.

14. The method of claim 9, wherein modulating F-box protein activity or expression comprises enhancing or inhibiting binding of the F-box protein to a protein encoded by a gene involved in the ethylene response of the plant.

15. The method of claim 14, wherein enhancing or inhibiting the binding of an F-box protein to a protein encoded by a gene involved in the ethylene response comprises enhancing or inhibiting the binding of an F-box protein to a transcription factor involved in the ethylene response.

16. The method of claim 15, wherein enhancing or inhibiting the binding of an F-box protein to a transcription factor involved in the ethylene response comprises enhancing or inhibiting the binding of an F-box protein to an EIN3 protein having at least 90% identity to the amino acid sequence shown in SEQ ID NO: 6.

17. The method of claim 9, wherein the aspect of the ethylene response that is regulated is senescence, fruit ripening, stress response, germination, pathogen resistance, leaf abscission, or stability of an EIN3 protein.

18. The method of claim 9, wherein the plant is selected from the group consisting of: rice, maize, wheat, barley, sorghum, millet, grass, oats, tomato, potato, banana, kiwi fruit, avocado, melon, mango, cane, sugar beet, tobacco, papaya, peach, strawberry, raspberry, blackberry, blueberry, lettuce, cabbage, cauliflower, onion, broccoli, brussels sprouts, cotton, canola, grape, soybean, oil seed rape, asparagus, beans, carrots, cucumbers, eggplant, melons, okra, parsnips, peanuts, peppers, pineapples, squash, sweet potatoes, rye, cantaloupes, peas, pumpkins, sunflowers, spinach, apples, cherries, cranberries, grapefruit, lemons, limes, nectarines, oranges, peaches, pears, tangelos, tangerines, lily, carnation, chrysanthemum, petunia, rose, geranium, violet, gladioli, orchid, lilac, crabapple, sweetgum, maple, poinsettia, locust, ash, linden tree and *Arabidopsis thaliana*.

19. A transgenic plant comprising a recombinant nucleic acid sequence that alters expression of an F-box gene, wherein the F-box gene encodes a first protein comprising at least 90% sequence identity to the amino acid sequence shown in SEQ ID NO: 4 and comprising an F-box domain shown in SEQ ID NO: 7, wherein the first protein interacts with a second protein involved in an ethylene response of the plant, wherein the recombinant nucleic acid sequence is operably linked to a promoter, and wherein said plant has altered sensitivity to ethylene.

* * * * *

UNITED STATES PATENT AND TRADEMARK OFFICE
CERTIFICATE OF CORRECTION

PATENT NO.         : 7,902,422 B2
APPLICATION NO.    : 12/643033
DATED              : March 8, 2011
INVENTOR(S)        : Guo et al.

It is certified that error appears in the above-identified patent and that said Letters Patent is hereby corrected as shown below:

In the Specification:

Column 1 line 42, "dicotyledoneous" should be --dicotyledonous--.

Column 4, line 13, "may includes" should be --may include--.

Column 5, line 19, "may includes" should be --may include--.

Column 5, line 33, "includes" should be --include--.

Column 7, line 12, both occurrences of "ebf1 ebf2," should be --ebf1, ebf2--.

Column 8, line 59, "portion or a plant" should be --portion of a plant--.

Column 9 line 3, "dicotyledoneous" should be --dicotyledonous--.

Column 9, line 37, "connection" should be --connections--.

Column 10, line 49, "that the others" should be --than the others--.

Column 11, line 38, "dicotyledoneous" should be --dicotyledonous--.

Column 12, lines 52-53, "dicotyledoneous" should be --dicotyledonous--.

Column 13, line 67, "dicotyledoneous" should be --dicotyledonous--.

Column 14, line 49, "tangerines, carnation" should be --tangerines, lily, carnation--.

Column 15, line 44, "lamda" should be --lambda--.

Column 17, line 39, "or derived" should be --or be derived--.

Column 22, line 16, "both" should be --all--.

Column 24, line 41, "response such (e.g.," should be --response (e.g.,--.

Column 24, line 42, "dicotyledoneous" should be --dicotyledonous--.

Column 24, line 65, "Proteosome" should be --Proteasome--.

Column 25, line 24, "degredation" should be --degradation--.

Column 29, line 56, "ebf1 ebf1" should be --ebf1 ebf2--.

Signed and Sealed this
Twentieth Day of September, 2011

David J. Kappos
*Director of the United States Patent and Trademark Office*

CERTIFICATE OF CORRECTION (continued)
U.S. Pat. No. 7,902,422 B2

Column 30, line 7, "*Mal*" should be --*Biol*--.

Column 34, line 29, "ebf1-1" should be --ebf2-1--.

Column 34, line 32, "ebf1" should be --ebf2--.

In SEQ ID NO: 3, "2162" should be --2161--.

In the Claims:

Column 65, line 23, claim 1, "with a EIN3" should be --with EIN3--.

Column 65, line 52, claim 8, "peach," should be deleted.

Column 66, line 26, claim 12, "and F-box" should be --an F-box--.

Column 66, line 57, claim 18, "peach," should be deleted.

SEQUENCE LISTING

<160> NUMBER OF SEQ ID NOS: 20

<210> SEQ ID NO 1
<211> LENGTH: 1918
<212> TYPE: DNA
<213> ORGANISM: Arabidopsis thaliana

<400> SEQUENCE: 1

| | | | | | |
|---|---|---|---|---|---|
| atgtctcaga | tctttagttt | tgccggtgaa | aatgatttt | accgtcgtgg | cgcaatatac | 60 |
| ccaaacccaa | aggatgctag | tcttttgtta | tcgcttggta | gtttcgctga | tgtttatttc | 120 |
| cctccaagca | agagatcacg | tgttgttgca | cctacgatct | tcagtgcttt | cgagaaaaag | 180 |
| ccagtttcca | ttgatgtgct | accagatgag | tgtcttttg | agatctttag | gcgtttgtct | 240 |
| ggaccacaag | agaggagtgc | ttgcgctttt | gtctccaaac | agtggcttac | gcttgtaagt | 300 |
| agcatccgtc | aaaaggagat | tgatgttcct | tccaagataa | ctgaagatgg | tgatgattgt | 360 |
| gaagggtgtt | tgtctaggag | cttagatggg | aagaaggcaa | cagatgttag | attggcagca | 420 |
| attgctgttg | gaactgctgg | tcgtggggga | cttggaaaat | tgtcgattcg | aggtagcaac | 480 |
| tctgctaaag | tttcagatct | tggtcttcgg | tctattggtc | gtagctgccc | ttctctcggg | 540 |
| tctctttcac | tgtggaacgt | ttctaccatt | actgacaatg | acttttgga | gattgctgag | 600 |
| ggttgtgctc | aacttgagaa | gcttgagctg | aaccgctgct | ctacaatcac | tgacaagggt | 660 |
| ttggtagcta | ttgctaagag | ctgccccaac | ttgactgagc | tgacattgga | ggcttgttca | 720 |
| agaattggag | atgagggttt | gctagccatt | gcaagatcct | gctccaagct | gaagtcagtc | 780 |
| tcgatcaaga | actgtcctct | tgtcagggat | caaggaatcg | cctctctact | gtctaacacc | 840 |
| acctgttcct | tggcaaaact | taagcttcag | atgctgaatg | tcactgatgt | gtctcttgct | 900 |
| gttgtgggtc | attacggctt | gtcgatcact | gatcttgtgc | tcgctggatt | atcacacgtg | 960 |
| agcgagaagg | gattctgggt | catgggaaat | ggtgtcgggc | tgcaaaaatt | aaactctctg | 1020 |
| accatcacag | cctgccaagg | agtgactgac | atggggcttg | aatctgttgg | aaagggctgc | 1080 |
| ccgaacatga | aaaaggcgat | catcagtaaa | tccccttgt | tatctgacaa | cgggttggtc | 1140 |
| tcttttgcaa | aagcttcttt | atcacttgag | agtcttcagc | ttgaagaatg | ccacagggtt | 1200 |
| acccaatttg | ggtttttgg | ttcccttttg | aactgtggtg | aaaagttgaa | ggctttctct | 1260 |
| ctggtgaact | gtttgagtat | tagagatctc | accacaggat | tgcctgcttc | atctcattgc | 1320 |

-continued

```
agcgctctgc gctctttgtc tattcgtaac tgccctggct ttggtgatgc aaatcttgca    1380
gccatcggga agttgtgccc tcagctcgag gatattgatc tgtgtgggct caagggata     1440
acagagtctg gtttcctaca tctgattcag agctctcttg tgaagatcaa cttcagtggt    1500
tgttccaatt tgactgatag agtgatctct gccatcactg ctcgtaacgg gtggactctt    1560
gaagtcttaa acatcgatgg atgttccaat atcactgacg ccagcctggt ctccattgca    1620
gcaaactgcc agattctcag tgatttggat atttcgaaat gcgcaatctc agattcaggg    1680
attcaagcat tggcctcctc tgataagctc aaactgcaga tcctatcagt tgcaggttgc    1740
tctatggtta cagacaagag cttgccagcc atcgtcgggt tgggttccac tctattggga    1800
ttaaacctcc aacagtgtcg atccatttcc aattccactg tcgacttctt agtcgagcgt    1860
ctttacaaat gtgacatcct ctcctgatca acaattccac tgtcgacctc tccactta     1918
```

<210> SEQ ID NO 2
<211> LENGTH: 628
<212> TYPE: PRT
<213> ORGANISM: Arabidopsis thaliana

<400> SEQUENCE: 2

```
Met Ser Gln Ile Phe Ser Phe Ala Gly Glu Asn Asp Phe Tyr Arg Arg
 1               5                  10                  15

Gly Ala Ile Tyr Pro Asn Pro Lys Asp Ala Ser Leu Leu Leu Ser Leu
            20                  25                  30

Gly Ser Phe Ala Asp Val Tyr Phe Pro Pro Ser Lys Arg Ser Arg Val
        35                  40                  45

Val Ala Pro Thr Ile Phe Ser Ala Phe Glu Lys Lys Pro Val Ser Ile
 50                  55                  60

Asp Val Leu Pro Asp Glu Cys Leu Phe Glu Ile Phe Arg Arg Leu Ser
 65                  70                  75                  80

Gly Pro Gln Glu Arg Ser Ala Cys Ala Phe Val Ser Lys Gln Trp Leu
                85                  90                  95

Thr Leu Val Ser Ser Ile Arg Gln Lys Glu Ile Asp Val Pro Ser Lys
            100                 105                 110

Ile Thr Glu Asp Gly Asp Cys Glu Gly Cys Leu Ser Arg Ser Leu
        115                 120                 125

Asp Gly Lys Lys Ala Thr Asp Val Arg Leu Ala Ala Ile Ala Val Gly
    130                 135                 140

Thr Ala Gly Arg Gly Gly Leu Gly Lys Leu Ser Ile Arg Gly Ser Asn
145                 150                 155                 160

Ser Ala Lys Val Ser Asp Leu Gly Leu Arg Ser Ile Gly Arg Ser Cys
                165                 170                 175

Pro Ser Leu Gly Ser Leu Ser Leu Trp Asn Val Ser Thr Ile Thr Asp
            180                 185                 190

Asn Gly Leu Leu Glu Ile Ala Glu Gly Cys Ala Gln Leu Glu Lys Leu
        195                 200                 205

Glu Leu Asn Arg Cys Ser Thr Ile Thr Asp Lys Gly Leu Val Ala Ile
    210                 215                 220

Ala Lys Ser Cys Pro Asn Leu Thr Glu Leu Thr Leu Glu Ala Cys Ser
225                 230                 235                 240

Arg Ile Gly Asp Glu Gly Leu Leu Ala Ile Ala Arg Ser Cys Ser Lys
                245                 250                 255

Leu Lys Ser Val Ser Ile Lys Asn Cys Pro Leu Val Arg Asp Gln Gly
            260                 265                 270

Ile Ala Ser Leu Leu Ser Asn Thr Thr Cys Ser Leu Ala Lys Leu Lys
```

```
                    275                 280                 285
Leu Gln Met Leu Asn Val Thr Asp Val Ser Leu Ala Val Val Gly His
            290                 295                 300
Tyr Gly Leu Ser Ile Thr Asp Leu Val Leu Ala Gly Leu Ser His Val
305                 310                 315                 320
Ser Glu Lys Gly Phe Trp Val Met Gly Asn Val Gly Leu Gln Lys
            325                 330                 335
Leu Asn Ser Leu Thr Ile Thr Ala Cys Gln Gly Val Thr Asp Met Gly
            340                 345                 350
Leu Glu Ser Val Gly Lys Gly Cys Pro Asn Met Lys Lys Ala Ile Ile
            355                 360                 365
Ser Lys Ser Pro Leu Leu Ser Asp Asn Gly Leu Val Ser Phe Ala Lys
        370                 375                 380
Ala Ser Leu Ser Leu Glu Ser Leu Gln Leu Glu Glu Cys His Arg Val
385                 390                 395                 400
Thr Gln Phe Gly Phe Gly Ser Leu Leu Asn Cys Gly Glu Lys Leu
                405                 410                 415
Lys Ala Phe Ser Leu Val Asn Cys Leu Ser Ile Arg Asp Leu Thr Thr
            420                 425                 430
Gly Leu Pro Ala Ser Ser His Cys Ser Ala Leu Arg Ser Leu Ser Ile
            435                 440                 445
Arg Asn Cys Pro Gly Phe Gly Asp Ala Asn Leu Ala Ala Ile Gly Lys
        450                 455                 460
Leu Cys Pro Gln Leu Glu Asp Ile Asp Leu Cys Gly Leu Lys Gly Ile
465                 470                 475                 480
Thr Glu Ser Gly Phe Leu His Leu Ile Gln Ser Ser Leu Val Lys Ile
                485                 490                 495
Asn Phe Ser Gly Cys Ser Asn Leu Thr Asp Arg Val Ile Ser Ala Ile
            500                 505                 510
Thr Ala Arg Asn Gly Trp Thr Leu Glu Val Leu Asn Ile Asp Gly Cys
            515                 520                 525
Ser Asn Ile Thr Asp Ala Ser Leu Val Ser Ile Ala Ala Asn Cys Gln
        530                 535                 540
Ile Leu Ser Asp Leu Asp Ile Ser Lys Cys Ala Ile Ser Asp Ser Gly
545                 550                 555                 560
Ile Gln Ala Leu Ala Ser Ser Asp Lys Leu Lys Leu Gln Ile Leu Ser
                565                 570                 575
Val Ala Gly Cys Ser Met Val Thr Asp Lys Ser Leu Pro Ala Ile Val
            580                 585                 590
Gly Leu Gly Ser Thr Leu Leu Gly Leu Asn Leu Gln Gln Cys Arg Ser
            595                 600                 605
Ile Ser Asn Ser Thr Val Asp Phe Leu Val Glu Arg Leu Tyr Lys Cys
        610                 615                 620
Asp Ile Leu Ser
625

<210> SEQ ID NO 3
<211> LENGTH: 2400
<212> TYPE: DNA
<213> ORGANISM: Arabidopsis thaliana

<400> SEQUENCE: 3
tcttcgatct cttcaaatct tcgtctttct tcttcaaatc ttcttcgaat tatgtctgga      60
atcttcagat ttagtggtga tgaagattgt ttacttgggg gatcgatgta tctatcacca     120
```

```
gggagctgtc ccggtgtata ttacccagcg cgtaagaggt tacgtgttgc tgcgacgtcg      180 tttttacagcg gttttgagga gaagcaaact tcaatcgatg tattgcctga agagtgttta      240
tttgagattc taagacgttt accttctgga caagagagga gtgcttgcgc ttgtgtttcc      300
aagcattggc ttaatctttt gagtagtatc agtaggagtg aagtgaatga gtcatcagtt      360
caagatgtgg aggagggtga agggtttttg tctaggagtt tggaggggaa gaaggcgacg      420
gatttgaggt tggcggcgat tgcggttggg acgtcgagtc gtggtgggtt ggggaagctt      480
cagattcgtg ggagtgggtt tgagagtaag gtgactgatg ttggtcttgg tgctgttgct      540 catgttgtc catctcttag gattgtttct ttatggaact tgcctgctgt tagtgatttg      600
ggtttgtctg agatcgcacg gtcatgcccg atgattgaaa aacttgacct ttcacggtgt      660
cctggaataa ctgacagtgg attggttgct attgctgaga actgtgtgaa tctgagtgat      720
ctgacgattg attcttgctc tggtgttggg aatgagggtt taagggctat tgcaagacgt      780
tgtgtcaatc tgagatctat ctctatcagg agctgcccac gtattggtga tcaaggtgtt      840
gccttcctct tggctcaagc tggttcttac ttgacgaaag tgaaactcca gatgctgaac      900
gtatctggtt tgtctcttgc tgttattggt cactacggag cagctgttac tgatcttgtg      960
cttcatggac ttcaaggtgt gaatgagaaa ggcttctggg ttatgggaaa tgcaaaaggg     1020
ttgaagaaac tgaagtccct ctcagtaatg tcgtgcagag gtatgaccga tgttgggctc     1080
gaagctgttg gaaatggttg ccctgatctg aagcatgtct ctctgaacaa atgcttgctt     1140
gtttctggta aaggacttgt cgcttttggcc aaatctgcat tgtcacttga agtttgaaa     1200 cttgaagaat gccacaggat caaccagttt ggtcttatgg gttttctcat gaactgtggc     1260
tcaaagttga aagcttttctc tttggcaaac tgtctgggca tcagtgactt caactcagaa     1320
tcctctctgc catcacccag ttgcagctct ttacgttctc tgtcaatccg atgctgccct     1380
gggtttgggg atgcaagtct cgctttcttg ggaaagttct gtcatcagct tcaggatgtt     1440
gaactctgtg gactaaacgg agtgacagat gcaggtgtgc gcgagttgct acagagcaac     1500
aatgttggtc tagtgaaggt gaacctgagc gaatgtatca atgtttcaga caacacagtc     1560
tctgcaattt ctgtttgcca cggacgcaca ttggagtctc ttaaccttga cggctgcaag     1620
aacatcacaa acgcaagcct tgtcgcagta gccaagaact gctactcagt caatgacctt     1680
gacatctcaa atactttggt ctcagatcac ggaatcaagg ccttggcatc ttctcctaac     1740
catctgaatc ttcaggttct ttccattggc ggctgctcct caattacaga caaaagcaag     1800
gcatgcatac aaaaactcgg ccgcacgctt ttgggattaa acatccaacg ttgtggcaga     1860
atcagcagca gcactgtgga tactcttctc gaaaatctat ggaggtgcga tatactctac     1920
taaattccca cttttttctac aaaaccttag tatcatcatc atcagtccaa gtcttttttcc     1980 taggttttgg tcgctaaaac ccatagattc cacctagaac ttagtttctt tctcaggaca     2040
ctgcagttgt tttttaaaat ttttggcagg ttccttctaa acaaaggagc tgtttctac      2100 aactgttagt gttttttgtga agcctgtcac tgagttctgg taatctagtt tagggtttag     2160
tcttgaccgt ctttttggag ttgttgtctc tctatgttca gtaaagttct tgtagaagtc     2220
atttgttctt tggtttaggt tcgtgatagt gccttttatc ttcttccact gtagagcttt     2280 tgcaatggc ggtgtaactt cttaatccgc cattacaact cttcggagtt gttttttttgt     2340 gtgttatgta tctgccaaaa gctctgtttt ttcccacttt tttgtttaag gcactatctt     2400
```

<210> SEQ ID NO 4
<211> LENGTH: 623
<212> TYPE: PRT

<213> ORGANISM: Arabidopsis thaliana

<400> SEQUENCE: 4

Met Ser Gly Ile Phe Arg Phe Ser Gly Asp Glu Asp Cys Leu Leu Gly
1               5                   10                  15

Gly Ser Met Tyr Leu Ser Pro Gly Ser Cys Pro Gly Val Tyr Tyr Pro
            20                  25                  30

Ala Arg Lys Arg Leu Arg Val Ala Ala Thr Ser Phe Tyr Ser Gly Phe
        35                  40                  45

Glu Glu Lys Gln Thr Ser Ile Asp Val Leu Pro Glu Glu Cys Leu Phe
50                  55                  60

Glu Ile Leu Arg Arg Leu Pro Ser Gly Gln Glu Arg Ser Ala Cys Ala
65                  70                  75                  80

Cys Val Ser Lys His Trp Leu Asn Leu Ser Ser Ile Ser Arg Ser
                85                  90                  95

Glu Val Asn Glu Ser Ser Val Gln Asp Val Glu Glu Gly Gly Phe
            100                 105                 110

Leu Ser Arg Ser Leu Glu Gly Lys Lys Ala Thr Asp Leu Arg Leu Ala
        115                 120                 125

Ala Ile Ala Val Gly Thr Ser Arg Gly Gly Leu Gly Lys Leu Gln
130                 135                 140

Ile Arg Gly Ser Gly Phe Glu Ser Lys Val Thr Asp Val Gly Leu Gly
145                 150                 155                 160

Ala Val Ala His Gly Cys Pro Ser Leu Arg Ile Val Ser Leu Trp Asn
                165                 170                 175

Leu Pro Ala Val Ser Asp Leu Gly Leu Ser Glu Ile Ala Arg Ser Cys
            180                 185                 190

Pro Met Ile Glu Lys Leu Asp Leu Ser Arg Cys Pro Gly Ile Thr Asp
        195                 200                 205

Ser Gly Leu Val Ala Ile Ala Glu Asn Cys Val Asn Leu Ser Asp Leu
210                 215                 220

Thr Ile Asp Ser Cys Ser Gly Val Gly Asn Glu Gly Leu Arg Ala Ile
225                 230                 235                 240

Ala Arg Arg Cys Val Asn Leu Arg Ser Ile Ser Arg Ser Cys Pro
                245                 250                 255

Arg Ile Gly Asp Gln Gly Val Ala Phe Leu Leu Ala Gln Ala Gly Ser
            260                 265                 270

Tyr Leu Thr Lys Val Lys Leu Gln Met Leu Asn Val Ser Gly Leu Ser
        275                 280                 285

Leu Ala Val Ile Gly His Tyr Gly Ala Ala Val Thr Asp Leu Val Leu
290                 295                 300

His Gly Leu Gln Gly Val Asn Glu Lys Gly Phe Trp Val Met Gly Asn
305                 310                 315                 320

Ala Lys Gly Leu Lys Lys Leu Lys Ser Leu Ser Val Met Ser Cys Arg
                325                 330                 335

Gly Met Thr Asp Val Gly Leu Glu Ala Val Gly Asn Gly Cys Pro Asp
            340                 345                 350

Leu Lys His Val Ser Leu Asn Lys Cys Leu Val Ser Gly Lys Gly
        355                 360                 365

Leu Val Ala Leu Ala Lys Ser Ala Leu Ser Leu Glu Ser Leu Lys Leu
370                 375                 380

Glu Glu Cys His Arg Ile Asn Gln Phe Gly Leu Met Gly Phe Leu Met
385                 390                 395                 400

Asn Cys Gly Ser Lys Leu Lys Ala Phe Ser Leu Ala Asn Cys Leu Gly

```
                      405                 410                 415
Ile Ser Asp Phe Asn Ser Glu Ser Ser Leu Pro Ser Pro Ser Cys Ser
            420                 425                 430

Ser Leu Arg Ser Leu Ser Ile Arg Cys Cys Pro Gly Phe Gly Asp Ala
            435                 440                 445

Ser Leu Ala Phe Leu Gly Lys Phe Cys His Gln Leu Gln Asp Val Glu
            450                 455                 460

Leu Cys Gly Leu Asn Gly Val Thr Asp Ala Gly Val Arg Glu Leu Leu
465                 470                 475                 480

Gln Ser Asn Asn Val Gly Leu Val Lys Val Asn Leu Ser Glu Cys Ile
                485                 490                 495

Asn Val Ser Asp Asn Thr Val Ser Ala Ile Ser Val Cys His Gly Arg
            500                 505                 510

Thr Leu Glu Ser Leu Asn Leu Asp Gly Cys Lys Asn Ile Thr Asn Ala
            515                 520                 525

Ser Leu Val Ala Val Ala Lys Asn Cys Tyr Ser Val Asn Asp Leu Asp
            530                 535                 540

Ile Ser Asn Thr Leu Val Ser Asp His Gly Ile Lys Ala Leu Ala Ser
545                 550                 555                 560

Ser Pro Asn His Leu Asn Leu Gln Val Leu Ser Ile Gly Gly Cys Ser
                565                 570                 575

Ser Ile Thr Asp Lys Ser Lys Ala Cys Ile Gln Lys Leu Gly Arg Thr
            580                 585                 590

Leu Leu Gly Leu Asn Ile Gln Arg Cys Gly Arg Ile Ser Ser Ser Thr
            595                 600                 605

Val Asp Thr Leu Leu Glu Asn Leu Trp Arg Cys Asp Ile Leu Tyr
    610                 615                 620

<210> SEQ ID NO 5
<211> LENGTH: 2413
<212> TYPE: DNA
<213> ORGANISM: Arabidopsis thaliana

<400> SEQUENCE: 5
acagagagac tccacaaaga aacgcaaata aacaaaagtc gctttctagc cacgtgatct      60
ttcgtcgact tttcttcttc ttcttcttct tcctcttcct catctcgtat ctctaacttt     120
tgtcgaagtt cttttgatga aactagggtt tattatcttc tccttctttt tcccatcacc     180
atagaaaagg cagagacctt tttcttcatc atttttattc tccttcttct tctgctgttc     240
atttctccag gttacaatga tgtttaatga gatgggaatg tgtggaaaca tggatttctt     300
ctcttctgga tcacttggtg aagttgattt ctgtcctgtt ccacaagctg agcctgattc     360
cattgttgaa gatgactata ctgatgatga gattgatgtt gatgaattgg agaggaggat     420
gtggagagac aaaatgcggc ttaaacgtct caaggagcag ataagggta aagaaggtgt      480 tgatgctgct aaacagaggc agtctcaaga gcaagctagg aggaagaaaa tgtctagagc     540
tcaagatggg atcttgaagt atatgttgaa gatgatggaa gtttgtaaag ctcaaggctt     600
tgtttatggg attattccgg agaatgggaa gcctgtgact ggtgcttctg ataatttaag     660
ggagtggtgg aaagataagg ttaggtttga tcgtaatggt cctgcggcta ttaccaagta     720
tcaagcggag aataatatcc cggggattca tgaaggtaat aacccgattg gaccgactcc     780
tcataccttg caagagcttc aagacacgac tcttggatcg cttttgtctg cgttgatgca     840
acactgtgat cctcctcaga gacgtttccc tttggagaaa ggagttcctc ctccgtggtg     900
gcctaatggg aaagaggatt ggtggcctca acttggtttg cctaaagatc aaggtcctgc     960
```

-continued

```
accttacaag aagcctcatg atttgaagaa ggcgtggaaa gtcggcgttt tgactgcggt    1020
tatcaagcat atgttttcctg atattgctaa gatccgtaag ctcgtgaggc aatctaaatg   1080
tttgcaggat aagatgactg ctaaagagag tgctacctgg cttgctatta ttaaccaaga   1140
agagtccttg gctagagagc tttatcccga gtcatgtcca cctcttttctc tgtctggtgg   1200
aagttgctcg cttctgatga atgattgcag tcaatacgat gttgaaggtt tcgagaagga   1260
gtctcactat gaagtggaag agctcaagcc agaaaaagtt atgaattctt caaactttgg   1320
gatggttgct aaaatgcatg actttcctgt caaagaagaa gtcccagcag gaaactcgga   1380
attcatgaga aagagaaagc caaacagaga tctgaacact attatggaca gaaccgtttt   1440
cacctgcgag aatcttgggt gtgcgcacag cgaaatcagc cggggatttc tggataggaa   1500
ttcgagagac aaccatcaac tggcatgtcc acatcgagac agtcgcttac cgtatggagc   1560
agcaccatcc aggtttcatg tcaatgaagt taagcctgta gttggatttc ctcagccaag   1620
gccagtgaac tcagtagccc aaccaattga cttaacgggt atagttcctg aagatggaca   1680
gaagatgatc tcagagctca tgtccatgta cgacagaaat gtccagagca ccaaacctc    1740
tatggtcatg gaaaatcaaa gcgtgtcact gcttcaaccc acagtccata accatcaaga   1800
acatctccag ttcccaggaa acatggtgga aggaagtttc tttgaagact tgaacatccc   1860
aaacagagca acaacaaca acagcagcaa caatcaaacg ttttttcaag ggaacaacaa   1920
caacaacaat gtgtttaagt tcgacactgc agatcacaac aactttgaag ctgcacataa   1980
caacaacaat aacagtagcg gcaacaggtt ccagcttgtg tttgattcca caccgttcga   2040
catggcgtca ttcgattaca gagatgatat gtcgatgcca ggagtagtag gaacgatgga   2100
tggaatgcag cagaagcagc aagatgtatc catatggttc taaagtcttg gtagtagatt   2160
tcatcttctc ttatttttat cttttgtgtt cttacattca ctcaaccatg taatatttttt   2220
tcctgggtct ctctgtctct atcgcttgtt atgatgtgtc tgtaagagtc tctaaaaact   2280
ctctgttact gtgtgtcttt gtctcggctt ggtgaatctc tctgtcatca tcagcttta   2340
gttacacacc cgacttgggg atgaacgaac actaaatgta agttttcata atataaatat    2400
atttgcaagc tct                                                        2413
```

<210> SEQ ID NO 6
<211> LENGTH: 628
<212> TYPE: PRT
<213> ORGANISM: Arabidopsis thaliana

<400> SEQUENCE: 6

```
Met Met Phe Asn Glu Met Gly Met Cys Gly Asn Met Asp Phe Phe Ser
  1               5                  10                  15

Ser Gly Ser Leu Gly Glu Val Asp Phe Cys Pro Val Pro Gln Ala Glu
             20                  25                  30

Pro Asp Ser Ile Val Glu Asp Tyr Thr Asp Glu Ile Asp Val
         35                  40                  45

Asp Glu Leu Glu Arg Arg Met Trp Arg Asp Lys Met Arg Leu Lys Arg
 50                  55                  60

Leu Lys Glu Gln Asp Lys Gly Lys Glu Gly Val Asp Ala Ala Lys Gln
 65                  70                  75                  80

Arg Gln Ser Gln Glu Gln Ala Arg Arg Lys Met Ser Arg Ala Gln
             85                  90                  95

Asp Gly Ile Leu Lys Tyr Met Lys Met Met Glu Val Cys Lys Ala
            100                 105                 110
```

-continued

```
Gln Gly Phe Val Tyr Gly Ile Ile Pro Glu Asn Gly Lys Pro Val Thr
        115                 120                 125
Gly Ala Ser Asp Asn Leu Arg Glu Trp Trp Lys Asp Lys Val Arg Phe
130                 135                 140
Asp Arg Asn Gly Pro Ala Ala Ile Thr Lys Tyr Gln Ala Glu Asn Asn
145                 150                 155                 160
Ile Pro Gly Ile His Glu Gly Asn Asn Pro Ile Gly Pro Thr Pro His
                165                 170                 175
Thr Leu Gln Glu Leu Gln Asp Thr Thr Leu Gly Ser Leu Leu Ser Ala
                180                 185                 190
Leu Met Gln His Cys Asp Pro Pro Gln Arg Arg Phe Pro Leu Glu Lys
                195                 200                 205
Gly Val Pro Pro Pro Trp Trp Pro Asn Gly Lys Glu Asp Trp Trp Pro
210                 215                 220
Gln Leu Gly Leu Pro Lys Asp Gln Gly Pro Ala Pro Tyr Lys Lys Pro
225                 230                 235                 240
His Asp Leu Lys Lys Ala Trp Lys Val Gly Val Leu Thr Ala Val Ile
                245                 250                 255
Lys His Met Phe Pro Asp Ile Ala Lys Ile Arg Lys Leu Val Arg Gln
                260                 265                 270
Ser Lys Cys Leu Gln Asp Lys Met Thr Ala Lys Glu Ser Ala Thr Trp
                275                 280                 285
Leu Ala Ile Ile Asn Gln Glu Glu Ser Leu Ala Arg Glu Leu Tyr Pro
290                 295                 300
Glu Ser Cys Pro Pro Leu Ser Leu Ser Gly Gly Ser Cys Ser Leu Leu
305                 310                 315                 320
Met Asn Asp Cys Ser Gln Tyr Asp Val Glu Gly Phe Glu Lys Glu Ser
                325                 330                 335
His Tyr Glu Val Glu Glu Leu Lys Pro Glu Lys Val Met Asn Ser Ser
                340                 345                 350
Asn Phe Gly Met Val Ala Lys Met His Asp Phe Pro Val Lys Glu Glu
                355                 360                 365
Val Pro Ala Gly Asn Ser Glu Phe Met Arg Lys Arg Lys Pro Asn Arg
                370                 375                 380
Asp Leu Asn Thr Ile Met Asp Arg Thr Val Phe Thr Cys Glu Asn Leu
385                 390                 395                 400
Gly Cys Ala His Ser Glu Ile Ser Arg Gly Phe Leu Asp Arg Asn Ser
                405                 410                 415
Arg Asp Asn His Gln Leu Ala Cys Pro His Arg Asp Ser Arg Leu Pro
                420                 425                 430
Tyr Gly Ala Ala Pro Ser Arg Phe His Val Asn Glu Val Lys Pro Val
                435                 440                 445
Val Gly Phe Pro Gln Pro Arg Pro Val Asn Ser Val Ala Gln Pro Ile
450                 455                 460
Asp Leu Thr Gly Ile Val Pro Glu Asp Gly Gln Lys Met Ile Ser Glu
465                 470                 475                 480
Leu Met Ser Met Tyr Asp Arg Asn Val Gln Ser Asn Gln Thr Ser Met
                485                 490                 495
Val Met Glu Asn Gln Ser Val Ser Leu Leu Gln Pro Thr Val His Asn
                500                 505                 510
His Gln Glu His Leu Gln Phe Pro Gly Asn Met Val Glu Gly Ser Phe
                515                 520                 525
Phe Glu Asp Leu Asn Ile Pro Asn Arg Ala Asn Asn Asn Asn Ser Ser
530                 535                 540
```

```
Asn Asn Gln Thr Phe Phe Gln Gly Asn Asn Asn Asn Asn Val Phe
545                 550                 555                 560

Lys Phe Asp Thr Ala Asp His Asn Asn Phe Glu Ala Ala His Asn Asn
            565                 570                 575

Asn Asn Asn Ser Ser Gly Asn Arg Phe Gln Leu Val Phe Asp Ser Thr
            580                 585                 590

Pro Phe Asp Met Ala Ser Phe Asp Tyr Arg Asp Asp Met Ser Met Pro
            595                 600                 605

Gly Val Val Gly Thr Met Asp Gly Met Gln Gln Lys Gln Gln Asp Val
            610                 615                 620

Ser Ile Trp Phe
625

<210> SEQ ID NO 7
<211> LENGTH: 44
<212> TYPE: PRT
<213> ORGANISM: Arabidopsis thaliana

<400> SEQUENCE: 7

Val Ser Ile Asp Val Leu Pro Asp Glu Cys Leu Phe Glu Ile Phe Arg
1               5                   10                  15

Arg Leu Ser Gly Pro Gln Glu Arg Ser Ala Cys Ala Phe Val Ser Lys
            20                  25                  30

Gln Trp Leu Thr Leu Val Ser Ser Ile Arg Gln Lys
        35                  40

<210> SEQ ID NO 8
<211> LENGTH: 44
<212> TYPE: PRT
<213> ORGANISM: Arabidopsis thaliana

<400> SEQUENCE: 8

Thr Ser Ile Asp Val Leu Pro Glu Glu Cys Leu Phe Glu Ile Leu Arg
1               5                   10                  15

Arg Leu Pro Ser Gly Gln Glu Arg Ser Ala Cys Ala Cys Val Ser Lys
            20                  25                  30

His Trp Leu Met Leu Leu Ser Ser Ile Ser Arg Ser
        35                  40

<210> SEQ ID NO 9
<211> LENGTH: 44
<212> TYPE: PRT
<213> ORGANISM: Arabidopsis thaliana

<400> SEQUENCE: 9

Arg Ile Ala Leu Ser Phe Pro Glu Glu Val Leu Glu His Val Phe Ser
1               5                   10                  15

Phe Ile Gln Leu Asp Lys Asp Arg Asn Ser Val Ser Leu Val Cys Lys
            20                  25                  30

Ser Trp Tyr Glu Ile Glu Arg Trp Cys Arg Arg Lys
        35                  40

<210> SEQ ID NO 10
<211> LENGTH: 44
<212> TYPE: PRT
<213> ORGANISM: Arabidopsis thaliana

<400> SEQUENCE: 10

Leu Ser Cys Val Ala Thr Val Asp Asp Val Ile Glu Gln Val Met Thr
1               5                   10                  15
```

Tyr Ile Thr Asp Pro Lys Asp Arg Asp Ser Ala Ser Leu Val Cys Arg
20                  25                  30

Arg Trp Phe Lys Ile Asp Ser Glu Thr Arg Glu His
        35                  40

<210> SEQ ID NO 11
<211> LENGTH: 43
<212> TYPE: PRT
<213> ORGANISM: Arabidopsis thaliana

<400> SEQUENCE: 11

Ile Gly Phe Ser Asn Leu Asp Glu Asn Leu Val Tyr Glu Val Leu Lys
1               5                   10                  15

His Val Asp Ala Lys Thr Leu Ala Met Ser Ser Cys Val Ser Lys Ile
            20                  25                  30

Trp His Lys Thr Ala Gln Asp Glu Arg Leu Trp
        35                  40

<210> SEQ ID NO 12
<211> LENGTH: 44
<212> TYPE: PRT
<213> ORGANISM: Arabidopsis thaliana

<400> SEQUENCE: 12

Thr Thr Leu Ser Asp Leu Pro Asp Val Ile Leu Ser Thr Ile Ser Ser
1               5                   10                  15

Leu Val Ser Asp Ser Arg Ala Arg Asn Ser Leu Ser Leu Val Ser His
            20                  25                  30

Lys Pro Leu Ala Leu Glu Arg Ser Thr Arg Ser His
        35                  40

<210> SEQ ID NO 13
<211> LENGTH: 43
<212> TYPE: PRT
<213> ORGANISM: Arabidopsis thaliana

<400> SEQUENCE: 13

Arg Ile Trp Ser Lys Leu Pro Pro Leu Leu Asp Arg Val Ile Ala
1               5                   10                  15

Phe Leu Pro Pro Pro Ala Phe Arg Thr Cys Val Cys Lys Arg
            20                  25                  30

Phe Tyr Ser Leu Leu Phe Ser Asn Thr Phe Leu
        35                  40

<210> SEQ ID NO 14
<211> LENGTH: 44
<212> TYPE: PRT
<213> ORGANISM: Arabidopsis thaliana

<400> SEQUENCE: 14

Cys Gly Ile Leu Gln Leu Ser Asp Glu Val Leu Ala His Asn Ile Leu
1               5                   10                  15

Ser Arg Leu Thr Pro Arg Asp Val Ala Ser Ile Gly Ser Ala Cys Arg
            20                  25                  30

Arg Leu Arg Gln Leu Thr Lys Asn Glu Ser Val Arg
        35                  40

<210> SEQ ID NO 15
<211> LENGTH: 44
<212> TYPE: PRT
<213> ORGANISM: Arabidopsis thaliana

```
<400> SEQUENCE: 15

Cys Gly Leu Phe Gln Leu Ser Asp Glu Val Val Ser His Lys Ile Leu
 1               5                  10                  15

Ser Arg Leu Thr Pro Arg Asp Val Ala Ser Val Ser Val Cys Arg
            20                  25                  30

Arg Leu Tyr Val Leu Thr Lys Asn Glu Asp Leu Trp
        35                  40

<210> SEQ ID NO 16
<211> LENGTH: 40
<212> TYPE: PRT
<213> ORGANISM: Arabidopsis thaliana

<400> SEQUENCE: 16

Met Ala Leu Pro Trp Glu Leu Glu Glu Asp Ile Leu Ser Arg Leu Pro
 1               5                  10                  15

Pro Ile Ser Leu Val Arg Phe Arg Thr Val Ser Lys His Trp Asn Ser
            20                  25                  30

Leu Phe Asn Asp Lys Thr Phe Ile
        35                  40

<210> SEQ ID NO 17
<211> LENGTH: 45
<212> TYPE: PRT
<213> ORGANISM: Arabidopsis thaliana

<400> SEQUENCE: 17

Val Ser Phe Ser Cys Ile Pro Glu Asp Val Val Phe His Ile Phe Phe
 1               5                  10                  15

Lys Leu Gln Asp Asp Pro Arg Asn Trp Ala Arg Leu Ala Cys Val Cys
            20                  25                  30

Thr Lys Phe Ser Ser Ile Val Arg Asn Val Cys Cys Lys
        35                  40                  45

<210> SEQ ID NO 18
<211> LENGTH: 43
<212> TYPE: PRT
<213> ORGANISM: Homo sapiens

<400> SEQUENCE: 18

Leu Thr Ile Leu Ser Leu Pro Glu Asp Val Leu Phe His Ile Leu Lys
 1               5                  10                  15

Trp Leu Ser Val Glu Asp Ile Leu Ala Val Arg Ala Val His Ser Gln
            20                  25                  30

Leu Lys Asp Leu Val Asp Asn His Ala Ser Val
        35                  40

<210> SEQ ID NO 19
<211> LENGTH: 43
<212> TYPE: PRT
<213> ORGANISM: Homo sapiens

<400> SEQUENCE: 19

Val Ser Trp Asp Ser Leu Pro Asp Glu Leu Leu Leu Gly Ile Phe Ser
 1               5                  10                  15

Cys Leu Cys Leu Pro Glu Leu Leu Lys Val Ser Gly Val Cys Lys Arg
            20                  25                  30

Trp Tyr Arg Leu Ala Ser Asp Glu Ser Leu Trp
        35                  40
```

```
<210> SEQ ID NO 20
<211> LENGTH: 42
<212> TYPE: PRT
<213> ORGANISM: Saccharomyces cerevisiae

<400> SEQUENCE: 20

Asp Leu Ile Thr Ser Leu Pro Phe Glu Ile Ser Leu Lys Ile Phe Asn
 1               5                  10                  15

Tyr Leu Gln Phe Glu Asp Ile Asn Ser Leu Gly Val Ser Gln Asn Trp
            20                  25                  30

Asn Lys Ile Ile Arg Lys Ser Thr Ser Leu
            35                  40
```